(12) United States Patent
Kataoka

(10) Patent No.: US 10,644,617 B2
(45) Date of Patent: May 5, 2020

(54) VIBRATION TYPE ACTUATOR APPARATUS INCREASED IN POSITION DETECTION ACCURACY, CONTROLLER, AND MEDICAL SYSTEM

(71) Applicant: CANON KABUSHIKI KAISHA, Tokyo (JP)

(72) Inventor: Kenichi Kataoka, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 860 days.

(21) Appl. No.: 15/142,148

(22) Filed: Apr. 29, 2016

(65) Prior Publication Data

US 2016/0329837 A1 Nov. 10, 2016

(30) Foreign Application Priority Data

May 8, 2015 (JP) .................................. 2015-095595

(51) Int. Cl.
*H02N 2/14* (2006.01)
*G05B 1/01* (2006.01)
(Continued)

(52) U.S. Cl.
CPC ........... *H02N 2/142* (2013.01); *A61B 5/0051* (2013.01); *A61B 5/0263* (2013.01); *A61B 5/055* (2013.01);
(Continued)

(58) Field of Classification Search
CPC . B60K 31/00; B60Y 2200/11; B60Y 2200/12; B60Y 2200/126; B60Y 2200/13;
(Continued)

(56) References Cited

U.S. PATENT DOCUMENTS

| 5,004,964 A | 4/1991 | Kataoka et al. |
| 5,768,229 A * | 6/1998 | Ikeda ................. G11B 7/08529 |
| | | 369/44.28 |

(Continued)

FOREIGN PATENT DOCUMENTS

| JP | 11-252962 A | 9/1999 |
| JP | 2000-060164 A | 2/2000 |

(Continued)

OTHER PUBLICATIONS

Office Action dated Feb. 5, 2019, in Japanese Patent Application No. 2015-095595.

*Primary Examiner* — Elvin G Enad
*Assistant Examiner* — Zoheb S Imtiaz
(74) *Attorney, Agent, or Firm* — Venable LLP

(57) ABSTRACT

A controller is capable of improving position detection accuracy during the stopping of an actuator, and controlling the actuator with high stability and quick responsiveness during driving. A first position signal corresponding to an amount of relative movement between the actuator and a driven element is output to a filter, and the filter outputs a second position signal generated by attenuating signal components having frequencies except a specific frequency band. Driving and stopping of the actuator are controlled according to the second position signal. As the specific frequency band, a first frequency band is set in the filter during the driving of the actuator, and a second frequency band is set in the filter during the stopping of the actuator. The first frequency band and the second frequency band both include 0 Hz, and the second frequency band is narrower than the first frequency band.

31 Claims, 30 Drawing Sheets

(51) Int. Cl.
*A61H 23/02* (2006.01)
*A61B 5/00* (2006.01)
*A61B 5/055* (2006.01)
*A61B 5/026* (2006.01)
*H02N 2/10* (2006.01)
*H02N 2/16* (2006.01)

(52) U.S. Cl.
CPC ............... *A61H 23/02* (2013.01); *G05B 1/01* (2013.01); *H02N 2/106* (2013.01); *H02N 2/163* (2013.01); *A61H 2201/1659* (2013.01); *A61H 2201/5007* (2013.01); *A61H 2201/5061* (2013.01); *A61H 2201/5064* (2013.01); *A61H 2201/5069* (2013.01); *A61H 2201/5092* (2013.01)

(58) Field of Classification Search
CPC ............ B60Y 2200/30; B60Y 2200/40; B60Y 2200/50; B60Y 2200/90; G01C 21/00
See application file for complete search history.

(56) References Cited

U.S. PATENT DOCUMENTS

| | | |
|---|---|---|
| 5,939,851 A | 8/1999 | Kataoka et al. |
| 6,031,316 A | 2/2000 | Kataoka |
| 6,313,564 B1 | 11/2001 | Kataoka et al. |
| 6,559,616 B2 | 5/2003 | Aoki et al. |
| 6,570,294 B1 | 5/2003 | Iino et al. |
| 2009/0049463 A1* | 2/2009 | Ueda ..................... G11B 19/28 720/695 |
| 2011/0273127 A1* | 11/2011 | Imamura ............. F02D 41/1497 318/650 |
| 2014/0239864 A1* | 8/2014 | Hansen .................... H02P 7/06 318/400.35 |
| 2017/0212497 A1* | 7/2017 | Kumazawa ............ G05B 19/05 |

FOREIGN PATENT DOCUMENTS

| | | |
|---|---|---|
| JP | 2000-270575 A | 9/2000 |
| JP | 2001-241971 A | 9/2001 |
| JP | 2005-266902 A | 9/2005 |
| JP | 2012-186897 A | 9/2012 |

\* cited by examiner

FIG. 18

| PATTERN | DURING DRIVING | | | DURING STOPPING | | |
|---|---|---|---|---|---|---|
| | FREQUENCY BAND 1 | FREQUENCY BAND 2 | TOTAL | FREQUENCY BAND 1 | FREQUENCY BAND 2 | TOTAL |
| 1 | Fr1 | — | Fr1 | Fr1 | Fr4 | Fr4 |
| 2 | Fr1 | — | Fr1 | Fr3<f<Fr1 | Fr4 | Fr4 |
| 3 | Fr1 | Fr2 | Fr2 | Fr1 | Fr4 | Fr4 |
| 4 | — | Fr2 | Fr2 | Fr2 | Fr4 | Fr4 |

VIBRATION TYPE ACTUATOR APPARATUS INCREASED IN POSITION DETECTION ACCURACY, CONTROLLER, AND MEDICAL SYSTEM

BACKGROUND OF THE INVENTION

Field of the Invention

The present invention relates to a vibration type actuator apparatus that is increased in position detection accuracy, a controller that controls the driving of an actuator of the vibration type actuator apparatus, and a medical system equipped with the vibration type actuator apparatus.

Description of the Related Art

As an example of an actuator that generates a driving force, there has been known a vibration actuator that brings a vibration element and a driven element into pressure contact with each other, and excites a vibration in the vibration element by applying an AC signal to thereby move the vibration element and the driven element relative to each other. The position control technique using the vibration actuator is used in various fields, such as an auto focus mechanism of an image pickup apparatus, a robot, a conveying equipment, a printing apparatus, and various manufacturing apparatuses. Of these various uses, the use in a field requiring particularly precise position control makes it necessary to increase the position accuracy during the driving and stopping of the vibration actuator. To meet this requirement, a measure is taken against electromagnetic noise, mechanical vibration, etc., which lowers the position accuracy.

The technique for coping with electromagnetic noise and mechanical vibration is roughly classified into one for preventing electromagnetic noise and mechanical vibration from entering the apparatus, and one for minimizing the influence of electromagnetic noise or mechanical vibration having entered the apparatus. Examples of the former technique include a technique related to e.g. an electromagnetic shield and a mechanical damper. This technique makes it possible to prevent electromagnetic noise and mechanical vibration from entering the apparatus, and hence provides a very large advantageous effect. However, the installation of an electromagnetic shield or a mechanical damper in the apparatus has a demerit in that the volume and weight of the apparatus are increased. On the other hand, examples of the latter technique include one related to a filter circuit inserted in an electric circuit, which can provide a certain effect while suppressing an increase in the volume and weight of the apparatus. However, a filter circuit having high noise elimination performance has a demerit in that delay in the temporal phase of the signal is increased, which degrades the stability and quick responsiveness in position control characteristics. In view of these problems, as a matter of fact, the former technique and the latter technique are often carried out in combination.

The latter technique also includes an example which suppresses noise superimposed on a position detection signal used in the actuator apparatus using an actuator. For example, Japanese Patent Laid-Open Publication No. 2012-186897 discloses a technique used in a controller for a pulse motor, for eliminating noise superimposed on a detection signal output from a position sensor connected to the pulse motor, using a filter. Further, Japanese Patent Laid-Open Publication No. 2001-241971 discloses a controller using a high pass filter for changing a cut-off frequency according to a rotational speed so as to extract a position detection signal from a ripple current of a DC motor. Furthermore, Japanese Patent Laid-Open Publication No. 2000-270575 discloses a low-pass filter used in a controller for a vibration actuator, which is capable of changing a cut-off frequency according to an amount of chattering of an encoder signal (position detection signal).

However, the technique described in Japanese Patent Laid-Open Publication No. 2012-186897 uses the filter that is capable of changing a cut-off frequency based on a speed command, and sets the cut-off frequency of the filter in proportion to the speed command. This cause a problem that the cut-off frequency of the filter during the stop of the pulse motor is mathematically equal to 0 (zero) Hz, and as a result, it is impossible to sufficiently detect changes in a position signal during the stop of the pulse motor. Further, since the cut-off frequency is set in proportion to the driving speed of the pulse motor, a phase delay in the position signal detected when the pulse motor is controlled to a low speed is relatively larger than a phase delay in the position signal detected when the pulse motor is controlled to a high speed, which lowers the stability and quick responsiveness when the pulse motor is controlled to a low speed.

In the technique disclosed in Japanese Patent Laid-Open Publication No. 2001-241971, since the high pass filter is used, as the rotational speed of the DC motor becomes lower, the amplitude of the position signal after being subjected to filtering is reduced, and when the motor is stopped, the signal ceases to be output. This causes a problem that the position detection accuracy is lowered when the motor is stopped.

The technique disclosed in Japanese Patent Laid-Open Publication No. 2000-270575 has a problem that the cut-off frequency of the low-pass filter is adjusted after noise is detected, and hence it is impossible to cope with sudden noise. Further, the cut-off frequency is not changed according to the driving speed of the vibration actuator, and hence it is impossible to perform control in quick adaptation to differences in vibration characteristics and control characteristics of the vibration actuator between when stopping the vibration actuator and when driving the vibration actuator.

SUMMARY OF THE INVENTION

The present invention relates to a controller that is capable of improving position detection accuracy during the stopping of an actuator of a vibration type actuator apparatus, and controlling the actuator with high stability and quick responsiveness during the driving of the actuator, the vibration type actuator apparatus, and a medical system equipped with the vibration type actuator apparatus.

In a first aspect of the invention, there is provided a controller that controls driving of an actuator, wherein a driven element and the actuator are relatively moved by a driving force of the actuator, and a relative positional relationship between the actuator and the driven element is held in a state in which driving of the actuator is stopped, comprising a position detection unit configured to output a first position signal corresponding to an amount of relative movement between the actuator and the driven element, a filter configured to have the first position signal input thereto, and output a second position signal generated by attenuating signal components having frequencies except a specific frequency band, a control unit configured to control driving and stopping of the actuator according to the second position signal, and a setting unit configured to set in the filter, as the specific frequency band, a first frequency band in a case where the control unit drives the actuator, and a second frequency band in a case where the control unit stops the actuator, wherein the first frequency band and the second frequency band both include 0 Hz, and the second frequency band is narrower than the first frequency band.

In a second aspect of the invention, there is provided a vibration type actuator apparatus including a vibration actuator, and a controller configured to control driving of the vibration actuator, the vibration actuator comprising a vibration element including an electromechanical energy conversion element, and an elastic body that is bonded to the electromechanical energy conversion element, and a driven element in pressure contact with the vibration element, wherein the vibration element and the driven element are moved relative to each other by vibration excited in the elastic body by applying a driving voltage to the electromechanical energy conversion element by the controller, the controller comprising a position detection unit configured to output a first position signal corresponding to an amount of relative movement between the vibration element and the driven element, a filter configured to have the first position signal input thereto, and output a second position signal generated by attenuating signal components having frequencies except a specific frequency band, a control unit configured to control driving and stopping of the vibration element according to the second position signal, and a setting unit configured to set in the filter, as the specific frequency band, a first frequency band in a case where the vibration element and the driven element are moved relative to each other, and a second frequency band in a case where a relative positional relationship between the vibration element and the driven element is held, wherein the first frequency band and the second frequency band both include 0 Hz, and the second frequency band is narrower than the first frequency band.

In a third aspect of the invention, there is provided a medical system including a vibration type actuator apparatus, and a driven mechanism for assisting predetermined medical inspection or treatment performed on a subject, wherein the vibration type actuator apparatus includes at least one vibration actuator, and a controller configured to control driving of each vibration actuator, each vibration actuator comprising a vibration element including an electromechanical energy conversion element, and an elastic body bonded to the electromechanical energy conversion element, and a driven element in pressure contact with the vibration element, wherein the vibration element and the driven element are moved relative to each other by vibration excited in the elastic body by applying a driving voltage to the electromechanical energy conversion element by the controller, the controller comprising a position detection unit configured to output a first position signal corresponding to an amount of relative movement between the vibration element and the driven element, a filter configured to have the first position signal input thereto, and output a second position signal generated by attenuating signal components having frequencies except a specific frequency band, a control unit configured to control driving and stopping of the vibration element according to the second position signal, and a setting unit configured to set in the filter, as the specific frequency band, a first frequency band in a case where the vibration element and the driven element are moved relative to each other, and a second frequency band in a case where a relative positional relationship between the vibration element and the driven element is held, wherein the first frequency band and the second frequency band both include 0 Hz, and the second frequency band is narrower than the first frequency band, wherein the driven mechanism includes a plurality of movable portions, and wherein the vibration actuator is integrated in each movable portion of the driven mechanism, and the vibration actuator performs motion of the movable portion.

According to the present invention, when the actuator is stopped, the first position signal output from the position detection unit is switched to the second position signal that is limited to the frequency band narrower than the frequency band for during the driving of the actuator and includes 0 Hz, whereby the control during the stopping of the actuator is performed based on the second position signal. This makes it possible to reduce noise superimposed on the position signal over a wide frequency range, and hence it is possible to increase the position detection accuracy during the stopping of the actuator. Further, the first position signal output from the position detection unit is switched to the second position signal which passes the filter over a wider frequency band during the driving of the actuator than during the stopping of the same, and the control during the driving of the actuator is performed based on the second position signal. This makes it possible to perform the control in quick adaptation according to differences in vibration characteristics and control characteristics of the actuator between when stopping the actuator and when driving the actuator, and further, it is possible to stably perform the position control with high accuracy.

Further features of the present invention will become apparent from the following description of exemplary embodiments (with reference to the attached drawings).

BRIEF DESCRIPTION OF THE DRAWINGS

FIG. 18 is a diagram showing an example of setting patterns of the frequency band, which are used by the controller shown in FIG. 15.

DESCRIPTION OF THE EMBODIMENTS

The present invention will now be described in detail below with reference to the accompanying drawings showing embodiments thereof. Note that in the following description, an actuator refers to a device that converts energy into a mechanical motion. Further, a vibration type actuator apparatus includes an actuator and a controller which controls the driving of the actuator.

Figure 1:
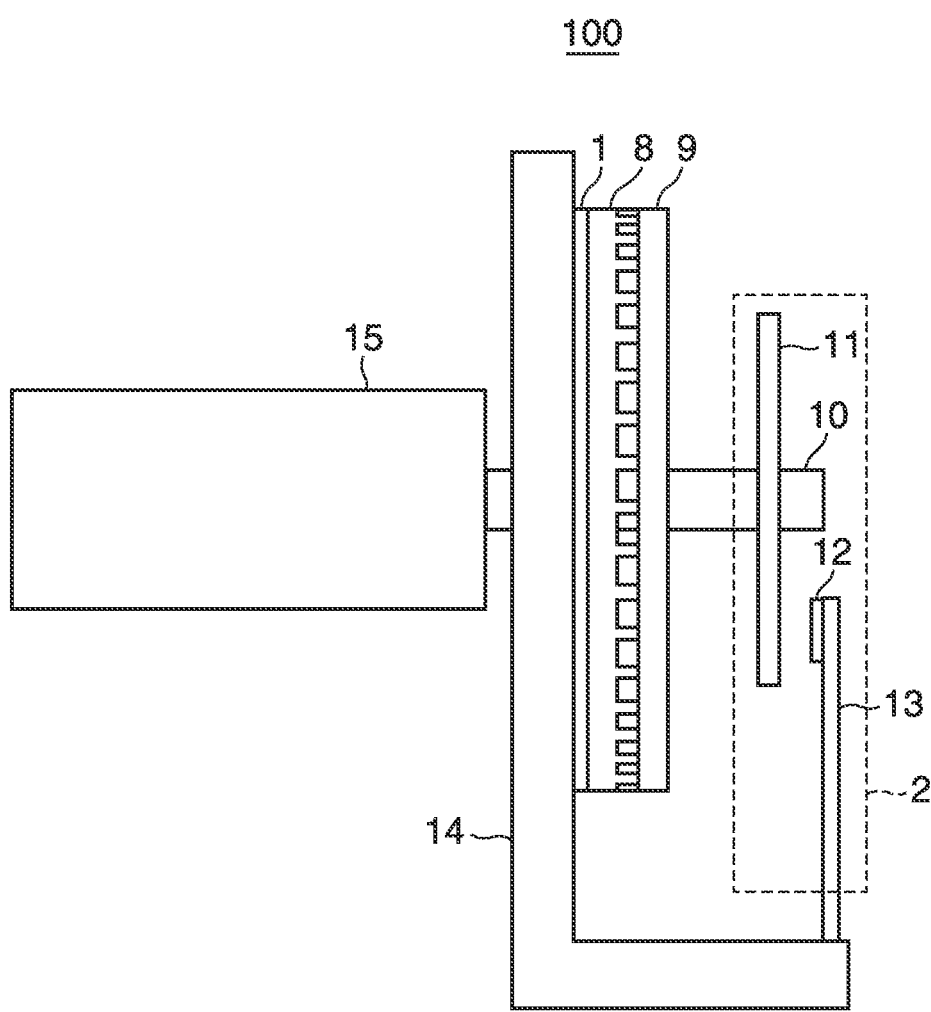
FIG. 1 is a schematic side view of a vibration actuator as a target of driving control of a controller according to embodiments of the present invention.
Figure 2:
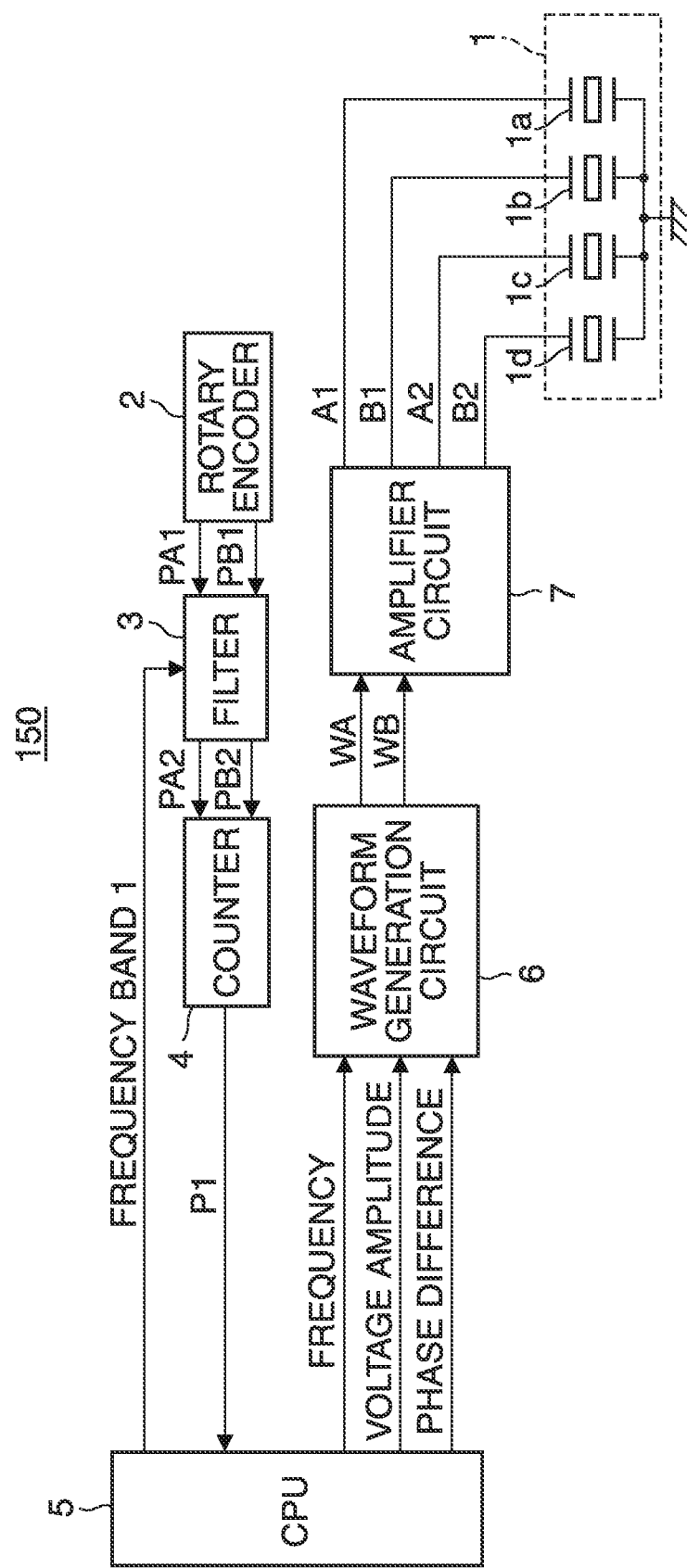
FIG. 2 is a schematic block diagram of the controller according to a first embodiment of the present invention, which controls the driving of the vibration actuator shown in FIG. 1.

FIG. 1 is a schematic side view of a vibration actuator 100 as a target of driving control of a controller according to embodiments of the present invention. FIG. 2 is a schematic block diagram of a controller 150 according to a first embodiment of the present invention, which controls the driving of the vibration actuator 100 shown in FIG. 1. The vibration actuator 100 shown in FIG. 1 and the controller 150 shown in FIG. 2 are components of the vibration type actuator apparatus according to the present invention.

The vibration actuator 100 includes an annular piezoelectric element 1, an annular elastic body 8, an annular driven element 9, an output shaft 10, and a support base 14. A rotary encoder 2 as a component of the controller 150 is mounted on the vibration actuator 100, and the rotary encoder 2 includes a disk-shaped optical scale 11, an optical sensor 12, and a circuit board 13.

The piezoelectric element 1 which is an electromechanical energy conversion element is bonded to the elastic body 8 which is made of metal, and the piezoelectric element 1 and the elastic body 8 form a vibration element. The piezoelectric element 1 includes electrodes 1a, 1b, 1c, and 1d (see FIGS. 1 and 4), and is capable of exciting a predetermined vibration in the elastic body 8 by applying driving voltages A1, B1, A2, and B2, referred to hereinafter, to the electrodes 1a, 1b, 1c, and 1d, respectively. The vibration excited in the elastic body 8 will be described hereinafter. The piezoelectric element 1 is fixed to the support base 14 using fixing means, not shown, so as to prevent the excited vibration from being impaired.

Although in the first embodiment, the piezoelectric element 1 is used to excite the predetermined vibration in the elastic body 8, this is not limitative, but an electrostrictive element, a magnetostrictive element, or the like may be used in place of the piezoelectric element 1. Further, although in the first embodiment, the vibration element is formed by the piezoelectric element 1 and the elastic body 8, a vibration element formed by the piezoelectric element alone can be used as well.

The driven element 9 is pressed against the elastic body 8 with a fixed pressure force by pressure means, not shown, and also is fitted on and fixed to the output shaft 10, such that it is held in a state rotatable about the rotational axis of the output shaft 10 in unison with the output shaft 10. The driven element 9 is frictionally driven by the vibration excited in the elastic body 8, and the output shaft 10 rotates in unison with the driven element 9 to thereby output a rotary driving force of the driven element 9 to the outside. One end of the output shaft 10 is attached to a roller 15. The roller 15 is a member which is driven for rotation in any of various apparatuses each equipped with the vibration actuator 100.

Note that the vibration actuator 100 can be configured such that the driven element 9 is fixed to the support base 14, the vibration element is fitted on and fixed to the output shaft 10 and is rotationally moved relative to the driven element 9. However, even when the vibration actuator 100 is configured such that the driven element 9 is fixed to the support base 14 and the vibration element is rotationally moved, there is no difference in that a rotary driving force is output via the output shaft 10. The following description is given assuming that the vibration actuator 100 is configured such that the vibration element is fixed on the support base 14, and the driven element 9 is driven for rotation, as described above.

The rotary encoder 2 is a position detection unit configured to detect a rotation angle and a rotation position which correspond to an amount of movement of the driven element 9 with respect to the vibration element. The optical scale 11 for detecting rotation is fixed on the output shaft 10 which rotates in unison with the driven element 9, and therefore, the optical scale 11 is rotated in unison with the driven element 9 and the output shaft 10. The optical sensor 12 irradiates a reflection pattern, not shown, formed on the optical scale 11 with light, and receives light reflected from the reflection pattern. The controller 150 detects a rotation angle and a rotation position of the driven element 9 based on the pattern of the reflected light received by the optical sensor 12. The optical sensor 12 is mounted on the circuit board 13, and the circuit board 13 is fixed to the support base 14.

As shown in FIG. 2, the controller 150 which controls the driving of the vibration actuator 100 includes the rotary encoder 2, a filter 3, a counter 4, a CPU 5, a waveform generation circuit 6, and an amplifier circuit 7.

The optical sensor 12 included in the rotary encoder 2 outputs two-phase position signals corresponding to light reflected from the optical scale 11 according to the rotation angle of the driven element 9, to the filter 3. Note that examples of the position detection unit, such as the rotary encoder 2, include one configured to detect a relative position and one configured to detect an absolute position. Whichever of these detection methods, position detection units may based, they can be classified into ones which directly output position data and ones which output a signal having a frequency corresponding to a speed. Further, the position detection units can be classified into ones that output a digital signal (pulse signal) and ones that output an analog signal (sine wave signal). Here, it is assumed that the rotary encoder 2 used in the first embodiment detects a relative position of the driven element 9, and outputs position signals PA1 and PB1 (first position signal) which are two-phase pulse signals having a frequency corresponding to a rotational speed and are shifted in phase by 90 degrees.

The filter 3 attenuates signal components outside a frequency range corresponding to a frequency band 1 set by the CPU 5 to thereby substantially cut off the signal components from the position signals PA1 and PB1, and outputs position signals PA2 and PB2 (second position signals) after the cutoff to the counter 4. The counter 4 detects a rotation angle and a rotation position of the driven element 9 based on the position signals PA2 and PB2 input from the filter 3, and outputs a position signal P1 to the CPU 5. Although in the first embodiment, the filter 3 and the counter 4 are explicitly described as the separate members, the functions of the filter 3 and the counter 4 may be consolidated into one counter.

The CPU 5 controls driving of the vibration actuator 100 based on the position signal P1 output from the counter 4, and a position command from command means, not shown. Driving control parameters are a frequency, a voltage amplitude, and a phase difference, and these parameters are used in combination according to a situation. The waveform generation circuit 6 generates pulse signals WA and WB, which are two-phase AC signals formed by combining the parameters supplied from the CPU 5, i.e. the frequency, the voltage amplitude, and the phase difference, and outputs the generated pulse signals WA and WB to the amplifier circuit 7. The amplifier circuit 7 converts the pulse signals WA and WB input from the waveform generation circuit 6 to differential signals by amplifying the same to predetermined amplitudes to thereby generate the four-phase driving voltages A1, B1, A2, and B2, and outputs the generated driving voltages A1, B1, A2, and B2 to the piezoelectric element 1. The four-phase driving voltages A1, B1, A2, and B2 are applied to the electrodes 1a, 1b, 1c, and 1d of the piezoelectric element 1, respectively.

Figure 3:
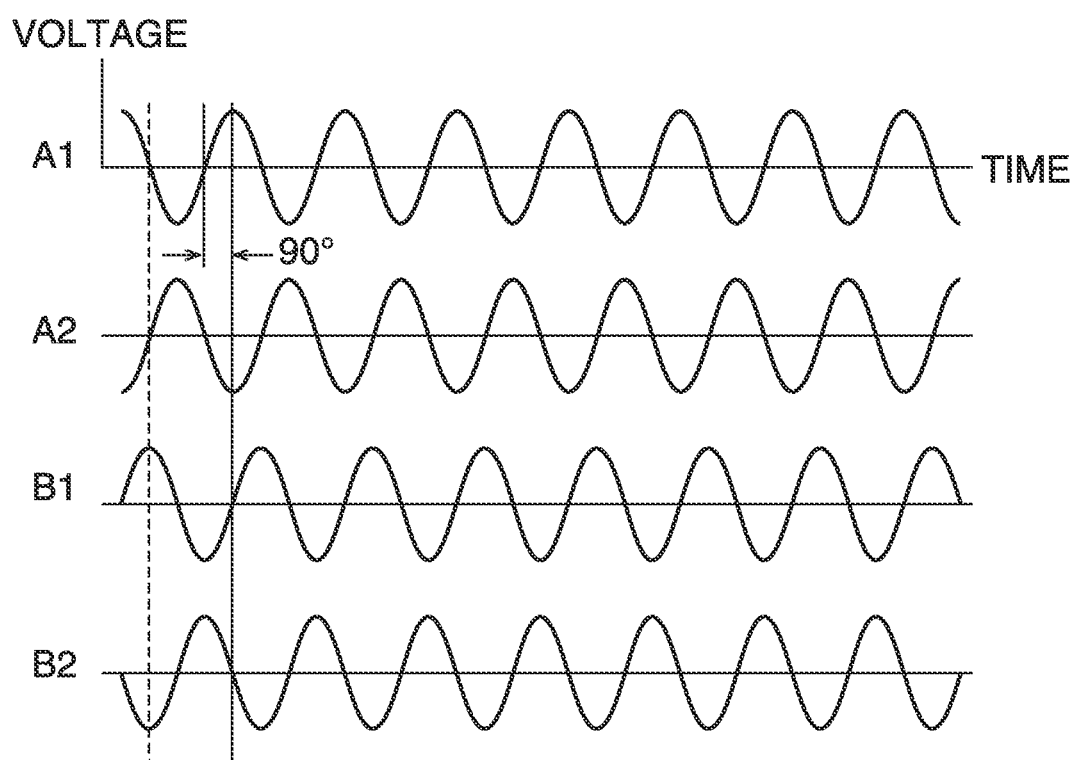
FIG. 3 is a diagram showing waveforms of driving voltages applied to a piezoelectric element of the vibration actuator shown in FIG. 1.

FIG. 3 is a diagram showing waveforms of the driving voltages A1, B1, A2, and B2. In the first embodiment, sine waveform voltages which are each shifted in phase by 90 degrees from one another are used as the driving voltages A1, B1, A2, and B2.

Figure 4:
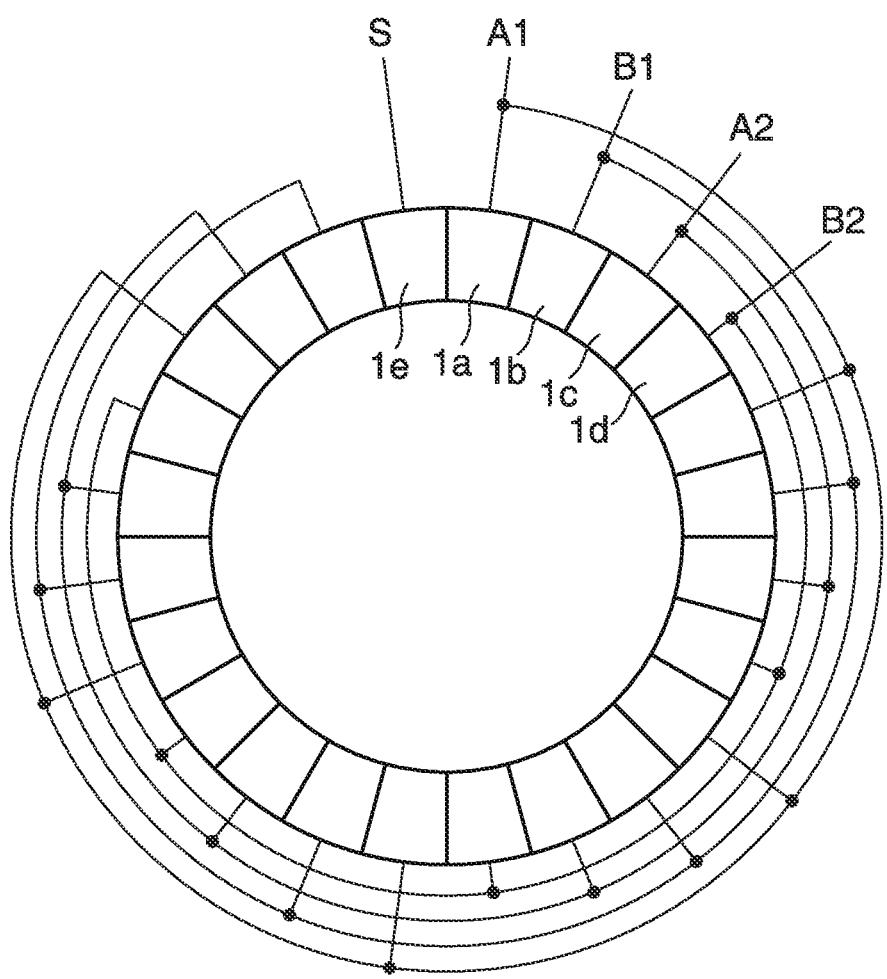
FIG. 4 is a diagram useful in explaining a relationship between electrode configuration of the piezoelectric element included in the vibration actuator shown in FIG. 1 and driving voltages applied to respective electrodes.

FIG. 4 is a diagram useful in explaining a relationship between the electrode configuration of the piezoelectric element 1 and the driving voltages applied to respective associated one of the electrodes. The piezoelectric element 1 has a structure in which one of surfaces of one annular piezoelectric ceramic plate is equally partitioned into 24 sections each formed with an electrode, and the other surface is formed with one full-surface electrode, not shown. The piezoelectric ceramic is polarized in a direction of a thickness, and by applying voltages between the electrodes of the 24 sections and the full-surface electrode on the reverse side, strain is generated in the piezoelectric element 1.

The electrodes 1a, 1b, 1c, and 1d are assigned to the electrodes of the 24 sections in a circumferential direction repeatedly in the mentioned order, respectively, and a last section to which the electrode 1d is to be assigned is assigned to an electrode 1e for detecting strain of the piezoelectric element 1. Therefore, the piezoelectric element 1 has six electrodes 1a, six electrodes 1b, six electrodes 1c, five electrodes 1d, and one electrode 1e. The electrode 1e is used to detect a signal S having a voltage caused by strain occurring in the section to which the electrode 1e is assigned, and the detailed description thereof will be given hereinafter.

When the driving voltages A1, B1, A2, and B2, which are each shifted in phase by 90 degrees, are applied to the electrodes 1a, 1b, 1c, and 1d, respectively, a bending vibration formed by six waves which are circumferentially equally spaced and orthogonal to the annular surface (surface orthogonal to a thrust direction) is generated in the elastic body 8. Then, the bending vibration formed by six waves becomes a travelling vibration wave that moves along the circumference while maintaining its waveform. At this time, an elliptical vibration that generates a tangent force in a direction opposite to a moving direction of the travelling vibration wave is formed at contact portions between protrusions (see FIG. 1) provided on the elastic body 8 at predetermined intervals in the circumferential direction and the driven element 9, and a relative driving force is generated between the elastic body 8 and the driven element 9. By exchanging the driving voltages B1 and B2, the traveling direction of the travelling vibration wave is reversed, and a driving force in the opposite direction is generated.

Note that the elastic body 8 has a natural vibration mode, and the vibration mode in which a bending vibration formed by six waves is formed has a natural vibration frequency at which the vibration is easily generated. Therefore, by making the frequency of an AC voltage applied to the piezoelectric element 1 close to the natural vibration frequency, it is possible to efficiently excite the bending vibration formed by six waves.

Next, the influence of electromagnetic noise on the position signals PA1 and PB1 output from the rotary encoder 2 will be described. As described hereinabove, the position signals PA1 and PB1 output from the rotary encoder 2 are pulse signals having a binary state, which are shifted in positional phase by 90 degrees. Changes in the position signals PA1 and PB1 caused by noise are generated regardless of actual changes in the position of the driven element 9, and are observed as a change from one of two values to the other one. Further, there are a case where this change is generated simultaneously in both the position signals PA1 and PB1, and a case where the change is generated in only one of them. In general, this change tends to be generated in only one of the position signals PA1 and PB1 when the amplitude of noise is small, and in both of the same when the amplitude of noise is large.

FIGS. 5A to 5D are timing diagrams showing internal signals of the rotary encoder 2 (output analog signals AA1 and AB1 from the optical sensor 12) and output signals from the rotary encoder 2 (position signals PA1 and PB1). In the rotary encoder 2, the optical sensor 12 receives reflected light corresponding to the reflection pattern provided on the optical scale 11, and outputs the sine wave analog signals AA1 and AB1 each having an amplitude corresponding to an amount of the received light as the internal signals. The analog signals AA1 and AB1 are compared with a fixed value using respective comparators, not shown, and are output from the rotary encoder 2 to the filter 3 as the binary position signals PA1 and PB1.

Figure 5A:
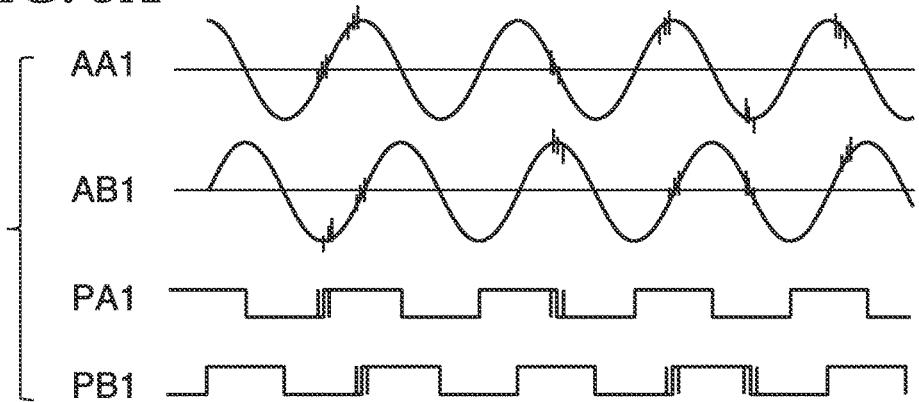
FIGS. 5A to 5D are timing diagrams of internal signals of a rotary encoder provided in the vibration actuator shown in FIG. 1, and output signals from the rotary encoder.

FIG. 5A shows an example of a case where small noise is superimposed on the analog signals AA1 and AB1. In this case, the noise is not simultaneously superimposed on both of the position signals PA1 and PB1, but is superimposed on one of the position signals PA1 and PB1. It is known from FIG. 5A that the noise is superimposed on the position signals PA1 and PB1 in the vicinity of a voltage level at which the analog signals AA1 and AB1 cross the threshold value of the comparator, not shown.

Figure 5B:
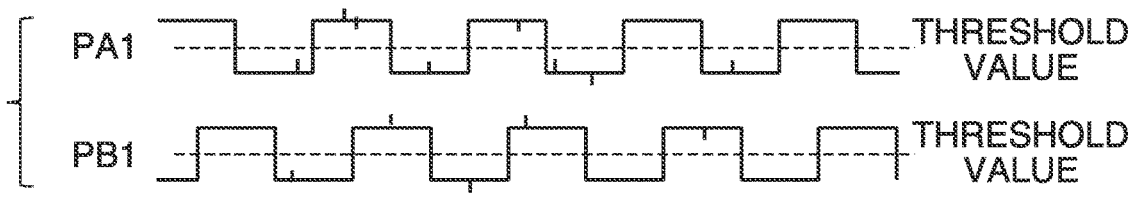

FIG. 5B shows an example of a case where small noise is directly superimposed on the position signals PA1 and PB1, together with a threshold value. The magnitude of noise superimposed on the position signals PA1 and PB1 does not exceed the threshold value of a circuit to which the position signals PA1 and PB1 are input, and hence in this case, the noise causes no adverse influence.

Figure 5C:
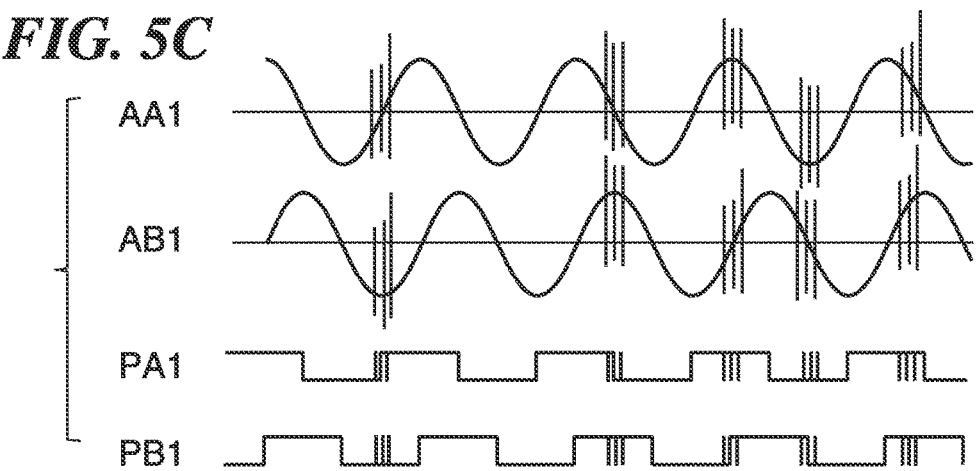
Figure 5D:
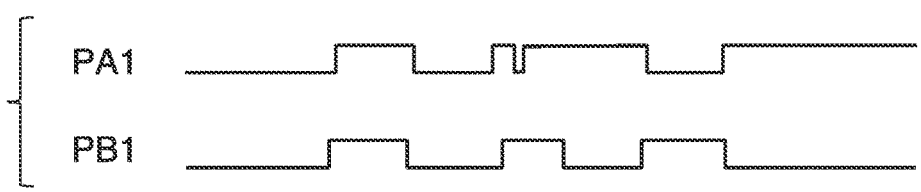

FIG. 5C shows an example of a case where large noise is superimposed on the analog signals AA1 and AB1. In this case, the noise is substantially simultaneously superimposed on both of the position signals PA1 and PB1. FIG. 5D is a diagram showing part of waveforms of the position signals PA1 and PB1 shown in FIG. 5C in a state expanded along the time axis. The position signals PA1 and PB1 are not detected exactly at respective phases shifted from each other by 90 degrees, but detected in a manner slightly displaced from those respective phases, and if such signals are counted by the counter 4, position errors may be accumulated.

Next, an influence of mechanical vibration (noise caused by mechanical vibration) on the position signals PA1 and PB1 output from the rotary encoder 2 will be described. The influence of vibration mechanically caused in the rotary encoder 2 on the position signals PA1 and PB1 is observed as a result of relative vibration between the optical scale 11 and the optical sensor 12. The vibration of the optical scale 11 includes vibrations in two directions: an in-plane direction and an out-of-plane direction with respect to the scale surface.

The vibration in the in-plane direction may be superimposed on the position signals PA1 and PB1 as a change in the rotation position of the optical scale 11 (a change in the rotation position of the driven element 9) depending on the vibration direction, but this phenomenon cannot be distinguished from a case where the rotation position of the driven element 9 is actually changed. On the other hand, the vibration in the out-of-plane direction causes a change in gap between the optical scale 11 and the optical sensor 12, and hence it is observed as a change in the amplitude of the analog signals AA1 and AB1, and hence has the same influence on the position signals PA1 and PB1 as the influence of small electromagnetic noise superimposed on the position signals PA1 and PB1. Most of vibrations of this type depend on the natural vibration mode due to a structure including a driving force transmission system in the vibration actuator 100, and are caused by resonation with a shock caused by the stop of driving of the vibration actuator 100 or some external vibration. Note that the natural vibration mode is classified into a plurality natural vibration modes, and each natural vibration mode has a specific frequency.

Figure 6A:
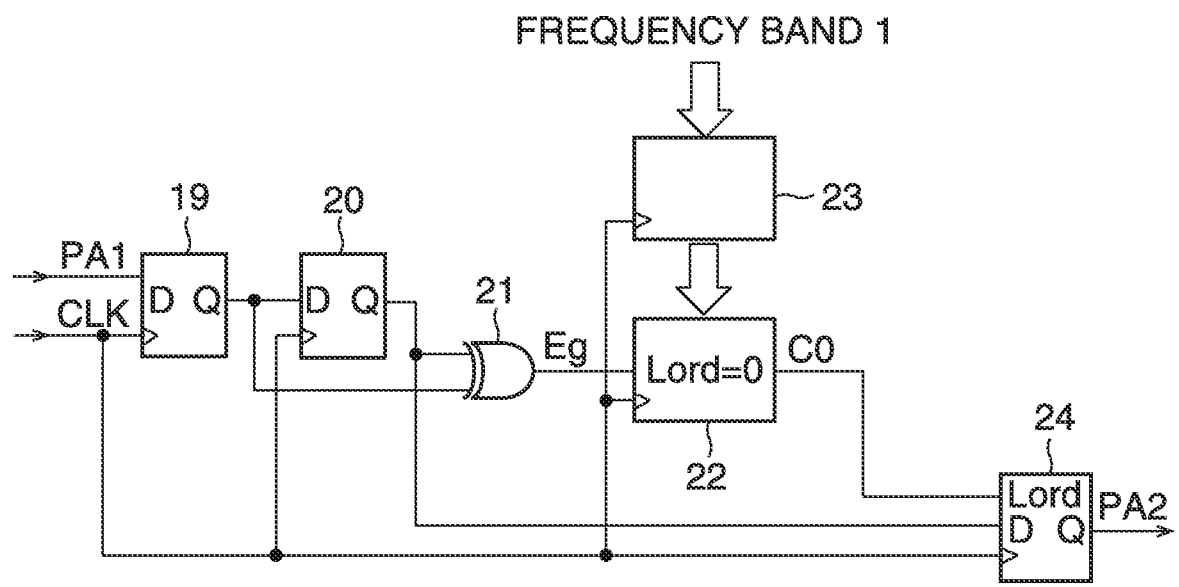
FIG. 6A is a circuit diagram of a filter as a component of the controller shown in FIG. 2.
Figure 6B:
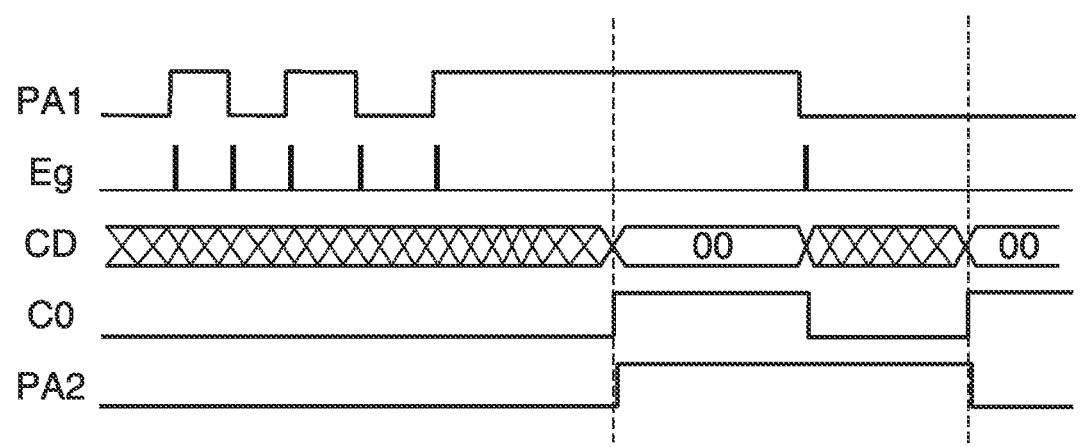
FIG. 6B is a timing diagram showing operation waveforms of the filter as the component of the controller shown in FIG. 2.

Next, a description will be given of the configuration and function of the filter 3 used as a countermeasure against a case where noise is superimposed on the position signals PA1 and PB1 for the above-described reason. FIG. 6A is a circuit diagram of the filter 3, and FIG. 6B is a timing diagram showing operation waveforms of the filter 3. FIGS. 6A and 6B show only a circuit that performs signal processing on the position signal PA1, and the operation waveforms in the filter 3. Note that the filter 3 also include a circuit equivalent to the circuit shown in FIG. 6A, as a circuit that performs signal processing on the position signal PB1.

The position signal PA1 is a signal that alternately outputs the binary state according to rotation of the driven element 9 (rotation of the optical scale 11 caused by the rotation of the driven element 9), as described with reference to FIGS. 5A to 5D. The filter 3 is a digital circuit, and various circuit components constituting the filter 3 operate in synchronism with a clock signal (CLK) of e.g. several MHz delivered from a crystal oscillator, not shown. Basically, only in a case where the position signal PA1 has the same value for a predetermined or longer time period, the filter 3 operates as a filter that passes the position signal PA1. In other words, the filter 3 operates as a filter that cuts off signals which vary in short time periods.

The filter 3 includes D-type flip flop circuits 19 and 20, an exclusive-OR element 21, a counter 22, a register 23, and a latch 24. The circuit part formed by the D-type flip flop circuits 19 and 20 and the exclusive-OR element 21 detects a change in the position signal PA1, and generates a narrow pulse-like signal Eg. The register 23 holds settings of the frequency band 1 set by the CPU 5.

The counter 22 reads the settings of the frequency band 1, held by the register 23, into a count CD whenever the signal Eg is input. Then, the counter 22 decrements the count CD by one whenever the CLK signal is input, and determines whether or not an interval (time interval) between two successive signal edges of the position signal PA1 is longer than the settings of the frequency band 1. Unless the pulse-like signal of the signal Eg is input, the counter 22 continues counting down, and when the count CD reaches 0, the counter 22 stops counting thereafter, judges that an interval between the signal edges is sufficiently long, and sets a signal C0 to a high level. On the other hand, if it is judged that an interval between the signal edges is short, the counter 22 sets the signal C0 to a low level.

When the signal C0 is at the high level, the latch 24 passes the position signal PA1 having passed the D-type flip flop circuits 19 and 20 which function as a 2-bit shift register in synchronism with the CLK signal. The signal thus output from the latch 24 is input to the counter 4 as a position signal PA2. The filter 3 operating as described above functions as a low-pass filter, and as a setting of the frequency band 1 (on a higher-frequency side) is set to a larger value, the filter 3 interferes passage of signals of a lower frequency.

In a case where the position signals PA1 and PB1 are changed by electromagnetic noise, since the driven element 9 is not actually moved, and hence the position of the driven element 9 may be erroneously detected. However, the filter 3 has the circuits independently provided for the position signals PA1 and PB1, respectively, and with respect to each of the position signals PA1 and PB1, when an interval between the two successive signal edges is shorter than a predetermined time period, the filter 3 operates to ignore this change. Therefore, as shown in FIG. 6B, if noise is spike-like noise having a narrow pulse width, with a short interval between two successive signal edges, and is within a frequency band sufficiently apart from the frequency of the position signals PA1 and PB1, this noise can be cut off. Thus, it is possible to suppress erroneous detection of the rotation position of the driven element 9.

On the other hand, the influences of mechanical vibration include, as already described above, one which cannot be distinguished from an actual change in the position of the driven element 9, and one which is not caused by a change in the position of the driven element 9. In the latter case, by using the filter 3, it is possible to obtain an advantageous effect equivalent to the above-described effect obtained with respect to the electromagnetic noise. On the other hand, in the former case, there is a possibility that the position of the driven element 9 is actually changed, and hence if all signals which change in short time periods are cut off by the filter 3, there is a possibility that an actual change in the position of the driven element 9 is overlooked. If the mechanical vibration is sporadic, and a change in the position of the driven element 9 before and after the stop of the mechanical vibration is small, even when signals which change in short time periods due to the mechanical vibration are eliminated by the filter 3, a detection error with respect to the actual position of the driven element 9 is not accumulated. In a case where the vibration amplitude is large, it is effective to combine the filter 3 with another countermeasure, such as a countermeasure of directly attenuating the mechanical vibration e.g. by using a mechanical damper.

As described above, the filter 3 cuts off electromagnetic noise or spike-like noise having a narrow pulse width, which is caused by mechanical vibration, and has an advantageous effect of reducing the influence of the noise. Further, when the vibration actuator 100 is stopped, the change in the position of the driven element 9 is slow, and hence after the vibration actuator 100 is stopped, the effect of reducing the influence of noise can also be obtained with respect to noise having a large pulse width and noise sporadically caused by mechanical vibration.

Figure 7:
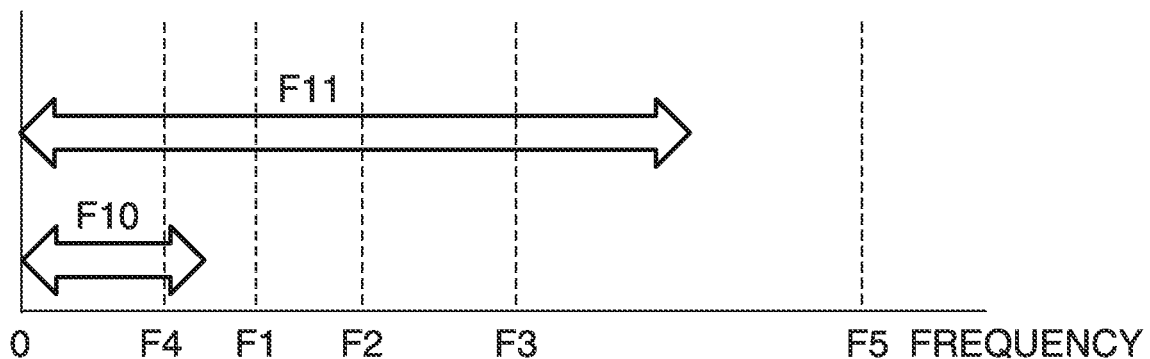
FIG. 7 is a diagram showing frequency bands of the filter set for during the stopping of the vibration actuator shown in FIG. 1 and for during the driving of the same.

Next, a description will be given of the settings of the frequency band 1 set in the filter 3 for during the driving of the vibration actuator 100 and for during the stopping of the same, respectively. FIG. 7 is a diagram showing the frequency bands set in the filter 3 for during the stopping of the vibration actuator 100 and for during the driving of the same. A value F1 and a value F2 on the horizontal axis represent frequencies of the natural vibration mode of the vibration actuator 100, respectively, and the value F1 represents the natural frequency of the lowest-order natural vibration mode of the vibration actuator 100. Further, a value F3 on the horizontal axis represents a frequency of the position signal PA1 occurring when the rotational speed of the driven element 9 is the maximum speed Vmax, and a value F4 represents a frequency of the position signal PA1 occurring when the rotational speed of the driven element 9 is the minimum speed Vmin. Further, a value F5 on the horizontal axis represents a frequency of a spike-like pulse of electromagnetic noise, i.e. a frequency represented e.g. by the reciprocal of a pulse width of the spike-like pulse.

A frequency band F11 (first frequency band) is defined by (includes) an upper limit which is a frequency higher than F3 and lower than F5, and a lower limit which is 0 Hz. Further, a frequency band F10 (second frequency band) is defined by (includes) an upper limit which is a frequency lower than F1 and also higher than F4, and a lower limit which is 0 Hz.

The frequency band 1 for during the stopping of the vibration actuator 100 is set to the frequency band F10, and the frequency band 1 for during the driving of the same is set to the frequency band F11. This makes it possible to cut off at least spike-like electromagnetic noise during the driving of the vibration actuator 100, and suppress the influence of noise during the stopping of the same, which is caused by mechanical vibration due to the above-mentioned lowest-order natural vibration mode. That is, it is possible to increase stability during stopping without lowering the quick responsiveness during driving, which makes it possible to perform stable position control irrespective of whether the vibration actuator 100 is being driven or stopped.

Note that at least one of notch filters each for cutting off noise having a specific frequency and comb filters each having a suppression effect on a plurality of specific equally-spaced frequencies may be used in combination with the filter 3. Further, even when the characteristics of the filter 3 are changed according to a rotational speed of the driven element 9 (relative moving speed between the vibration element and the driven element 9) during the driving of the vibration actuator 100, a problem is not caused insofar as the frequency band after the change is wider than the frequency band during stopping. Further, the configuration may be such that in a case where there is no influence of electromagnetic noise or the like, or occurrence of electrical chattering or the like, the settings of the frequency band 1 for during driving are cancelled, and there is substantially no limit to the frequency band.

Figure 8:
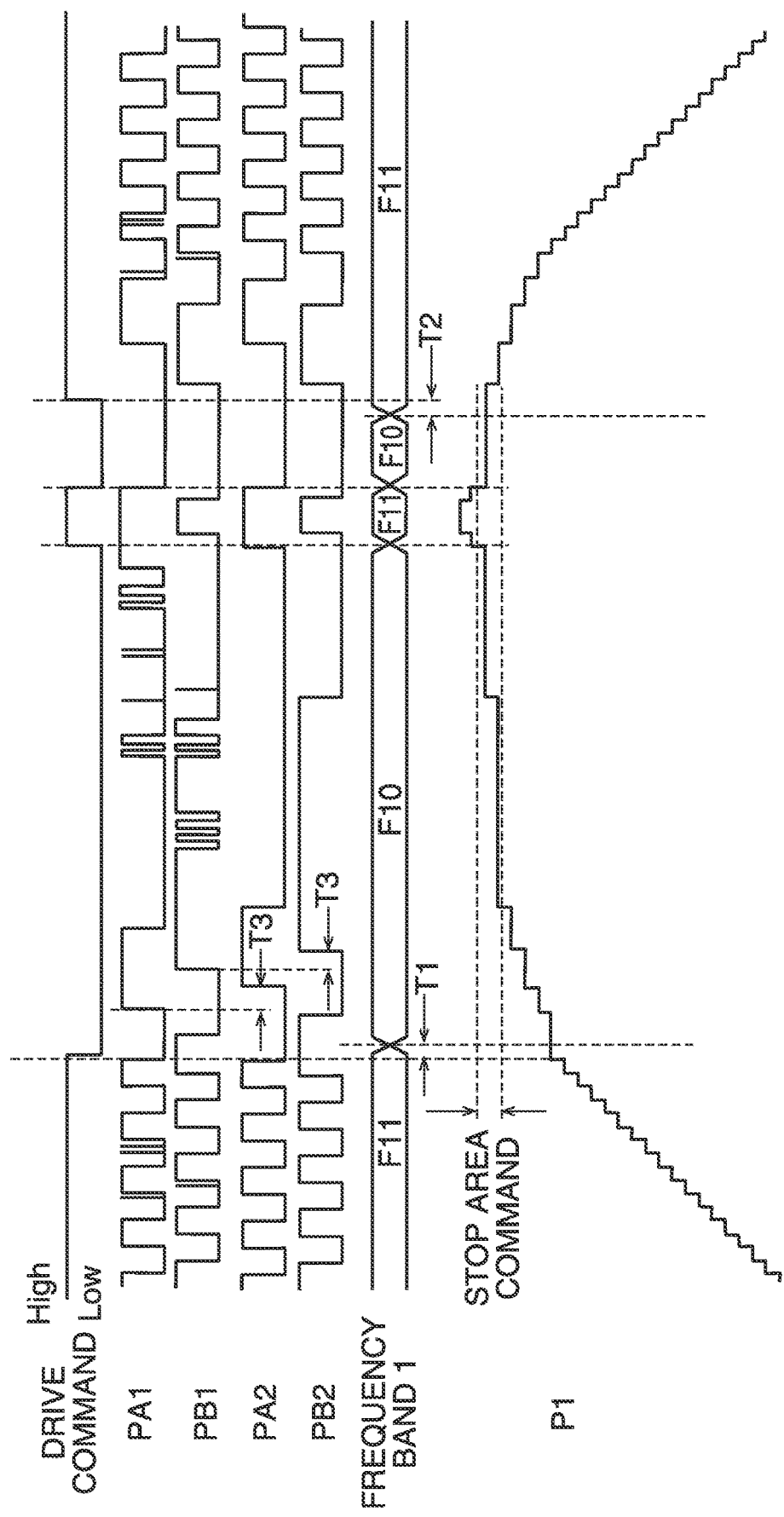
FIG. 8 is a timing diagram useful in explaining the control of driving of the vibration actuator, which is performed by the controller shown in FIG. 2.

Next, the overall operation of the controller 150 will be described. FIG. 8 is a timing diagram useful in explaining the control of driving of the vibration actuator 100, which is performed by the controller 150. FIG. 8 shows various signal waveforms observed from when the vibration actuator 100 is being driven, via a drive stop time period, until after the vibration actuator 100 is restarted. As described with reference to FIG. 7, the frequency band for during the driving of the vibration actuator 100 is set to the frequency band F11, and the frequency band for during stopping is set to the frequency band F10.

A "drive command" in FIG. 8 represents a signal generated by the CPU 5 based on a position command from the command means, not shown. A high level of the drive command indicates "during driving", and a low level indicates "during stopping". In a time period of "during stop", energization of the vibration actuator 100 is stopped. An area between broken lines in FIG. 8, indicated as a "stop area command", represents a range of a stopping target position instructed by the command means, not shown.

Here, the stop of energization of the vibration actuator 100 will be described. The stop of energization of the vibration actuator 100 refers to the stop of power supply to the piezoelectric element 1. In the first embodiment, the voltage amplitude of the waveform generation circuit 6 is set to zero (0), whereby the voltage amplitude of the driving voltages A1, B1, A2, and B2 is set to 0 [V]. However, this is not limitative, but energization of the vibration actuator 100 may be stopped by using a method of disconnecting between the amplifier circuit 7 and the piezoelectric element 1 by using a switch, not shown, or a method of stopping power supply to the amplifier circuit 7.

The method of stopping energization is different depending on the type of the actuator. For example, in the case of an actuator using an electromagnetic force, a method of setting excitation current to 0 [A] can be used, and further, the method of disconnecting a driving voltage by using a switch can be employed, similarly to the vibration actuator 100.

Figure 9A:
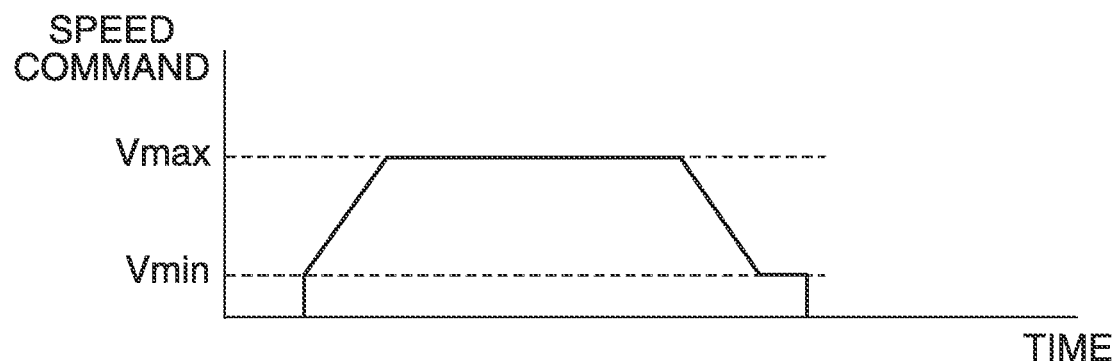
FIGS. 9A to 9C are diagrams each showing an example of a speed command pattern set to the vibration actuator shown in FIG. 1.
Figure 9B:
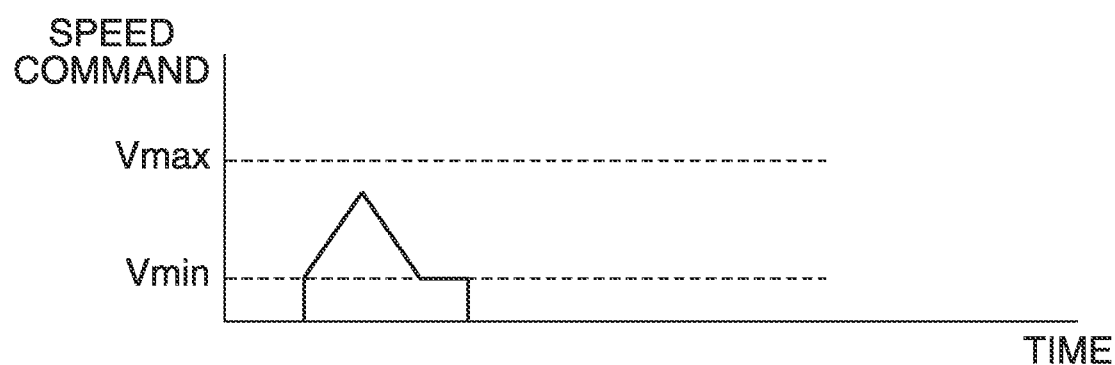
Figure 9C:
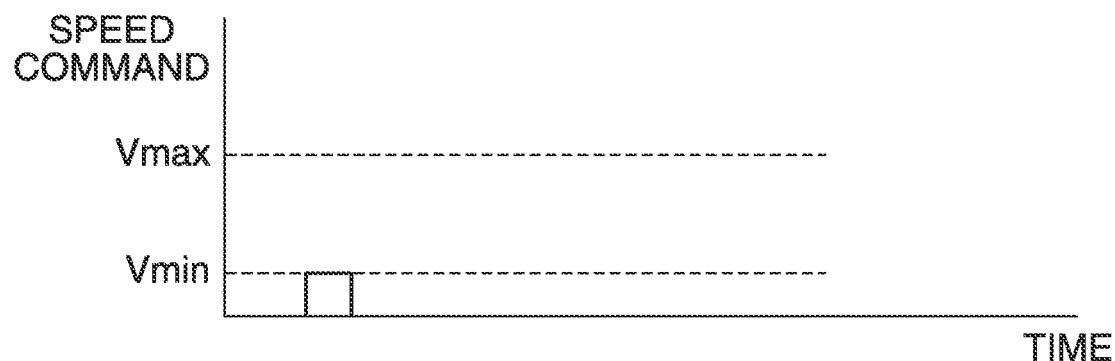

In the first embodiment, for rotational movement of the driven element 9 immediately before the stop of driving of the vibration actuator 100 or rotational movement of the driven element 9 through a minute rotation angle, constant speed control at the minimum speed (Vmin) is performed. FIGS. 9A to 9C are diagrams each showing an example of a speed command pattern used for the vibration actuator 100. FIG. 9A shows a basic speed pattern, and FIGS. 9B and 9C each show an example of the speed pattern in a case where a moving angle is smaller. Part in the timing diagram shown in FIG. 8, in which the vibration actuator 100 is driven to move the driven element 9 by a minute angle to finely adjust the stop position, shows an example of the operation performed in a case where the vibration actuator 100 is driven at the speed pattern shown in FIG. 9C.

When the vibration actuator 100 is being driven before stopping, spike-like noise caused by electromagnetic noise is superimposed on the position signals PA1 and PB1. Since the driven element 9 is being rotationally moved, even if small noise caused by mechanical vibration is superimposed on the position signals PA1 and PB1, a temporal change in phase is only slightly caused in the position signals PA1 and PB1, and no large influence of noise is observed.

Further, since the vibration actuator 100 is before stopping, i.e. during driving, the frequency band F11 is set in the filter 3 as the frequency band 1. Therefore, the filter 3 cuts off only spike-like noise superimposed on the position signals PA1 and PB1. As a result, the position signals PA2 and PB2 have a slight time delay with respect to the position signals PA1 and PB1, and the pulse signals which are shifted in phase by 90 degrees are output at a substantially constant frequency without spike-like noise. Therefore, signal processing performed by the filter 3 does not have a large influence on the control performance for the vibration actuator 100, and the position signal P1 increases at a stable constant rate in a stepped manner.

When the position signal P1 comes closer to a predetermined distance from the range of the stop area command, the CPU 5 decides to stop driving of the vibration actuator 100, and sets the drive command to the low level. Further, the CPU 5 outputs to the waveform generation circuit 6 a command for setting the amplitude of the driving voltage to 0 [V]. Upon receipt of this command, the waveform generation circuit 6 stops outputting of the pulse signals WA and WB. As a result, the amplitudes of the driving voltages A1, B1, A2, and B2 are changed to 0 [V], and the driving of the vibration actuator 100 is stopped. Note that the driven element 9 which is being rotationally moved cannot be immediately stopped even when the amplitudes of the driving voltages A1, B1, A2, and B2 are changed to 0 [V], and hence the driven element 9 is stopped within a target stop area after overrunning a certain distance.

To start the operation for stopping the vibration actuator 100 during driving, the CPU 5 changes the drive command from the high level to the low level. Then, the CPU 5 changes the frequency band 1 from the frequency band F11 to the frequency band F10 after a predetermined time period elapses (after a time period T1 elapses) after the change of the drive command from the high level to the low level. The frequency band F10 is a frequency band including the frequency of the position signals PA1 and PB1 immediately before the stop of driving of the vibration actuator 100, and hence the position signals PA1 and PB1 can be detected even in an area in which the speed is being reduced after changing the voltage amplitude to 0 [V].

When the vibration actuator 100 is being stopped, there is a possibility that the position signals PA1 and PB1 are changed by a mechanical vibration even though it is a minute one. FIG. 8 shows a state in which spike-like noise caused by electromagnetic noise and wider pulses caused by mechanical vibration are superimposed on the position signals PA1 and PB1. The frequency band F10 has the upper limit frequency which is lower than the upper limit frequency the frequency band F11 so as to cut off noise caused by mechanical vibration, whereby not only spike-like noise but also noise somewhat large in pulse width which is caused by mechanical vibration is suppressed. On the other hand, since the frequency band F10 is set as a narrower frequency band, a time delay (T3) of the position signals PA2 and PB2 with respect to the position signals PA1 and PB1 is caused.

When the position signal P1 deviates from the range of the stop area command during the stopping of the vibration actuator 100, the CPU 5 changes the drive command to the high level to thereby start the vibration actuator 100 so as to finely adjust the stop position of the driven element 9. More specifically, the CPU 5 sets the frequency, the voltage amplitude, and the phase difference of the waveform generation circuit 6 to predetermined values according to a distance and a direction of movement of the driven element 9. Further, the CPU 5 changes the frequency band 1 to the frequency band F11 simultaneously with the start of the vibration actuator 100 to thereby control the position signal P1 to return into the range of the stop area command. Here, since the frequency band 1 is set back to the frequency band F11 during the driving of the vibration actuator 100, a time delay of the position signals PA2 and PB2 with respect to the position signals PA1 and PB1 is hardly caused.

When the position signal P1 enters the range of the stop area command again, the CPU 5 sets the drive command to the low level, and the voltage amplitude to 0 [V], and changes the frequency band 1 from the frequency band F11 to the frequency band F10. At this time, although the CPU 5 switches the frequency band 1 almost simultaneously with switching of the drive command, this is because in the case where the vibration actuator 100 is driven to move the driven element 9 by a minute angle, a shock caused by stopping the driving is small, and further, the rotational speed does not exceed the minimum speed Vmin. As described above, the timing of setting the frequency band 1 of the filter 3 may be changed according to a situation.

After the lapse of a predetermined stop time period, the CPU 5 restarts the vibration actuator 100 based on a position command from the command means, not shown. Upon deciding to restart the vibration actuator 100, the CPU 5 changes the frequency band 1 from the frequency band F10 to the frequency band F11 a predetermined time period before (only a time period T2 before) switching of the drive command from the low level to the high level. This is to prevent the timing of switching of the frequency band 1 from becoming coincident with a shock caused by the start (mechanical vibration). After changing the frequency band 1, the CPU 5 sets the frequency, the voltage amplitude, and the phase difference of the waveform generation circuit 6 to the predetermined values, and restarts the vibration actuator 100.

After restarting the vibration actuator 100, the CPU 5 accelerates the vibration actuator 100 to the minimum speed (Vmin) as shown in FIG. 9C, and then controls the vibration actuator 100 to operate at a constant speed. At this time, similarly to the driving of the vibration actuator 100 before stopping, spike-like noise caused by the influence of electromagnetic noise is superimposed on the position signals PA1 and PB1. However, the pulse signals having a substantially fixed frequency without spike-like noise are output from the filter 3 as the position signals PA2 and PB2, and as a result, the position signal P1 decreases at a fixed rate in a stepped manner.

As described above, the frequency band 1 set in the filter 3 is switched when the driving of the vibration actuator 100 is switched to the stopping of the vibration actuator 100, and the frequency band during stopping is narrowed at this time, whereby it is possible to effectively suppress noise, and thereby perform stable control.

Next, as a variation of the first embodiment, a description will be given of a variation of the method of determining the timing of setting the frequency band 1 in the filter 3. Although in the above-described embodiment, the frequency band 1 set in the filter 3 is switched based on a condition that a predetermined time period elapses after a time point at which the drive command is changed, the frequency band 1 may be switched using a condition other than the time, and an example of this will be described with reference to FIGS. 10 and 11.

Figure 10:
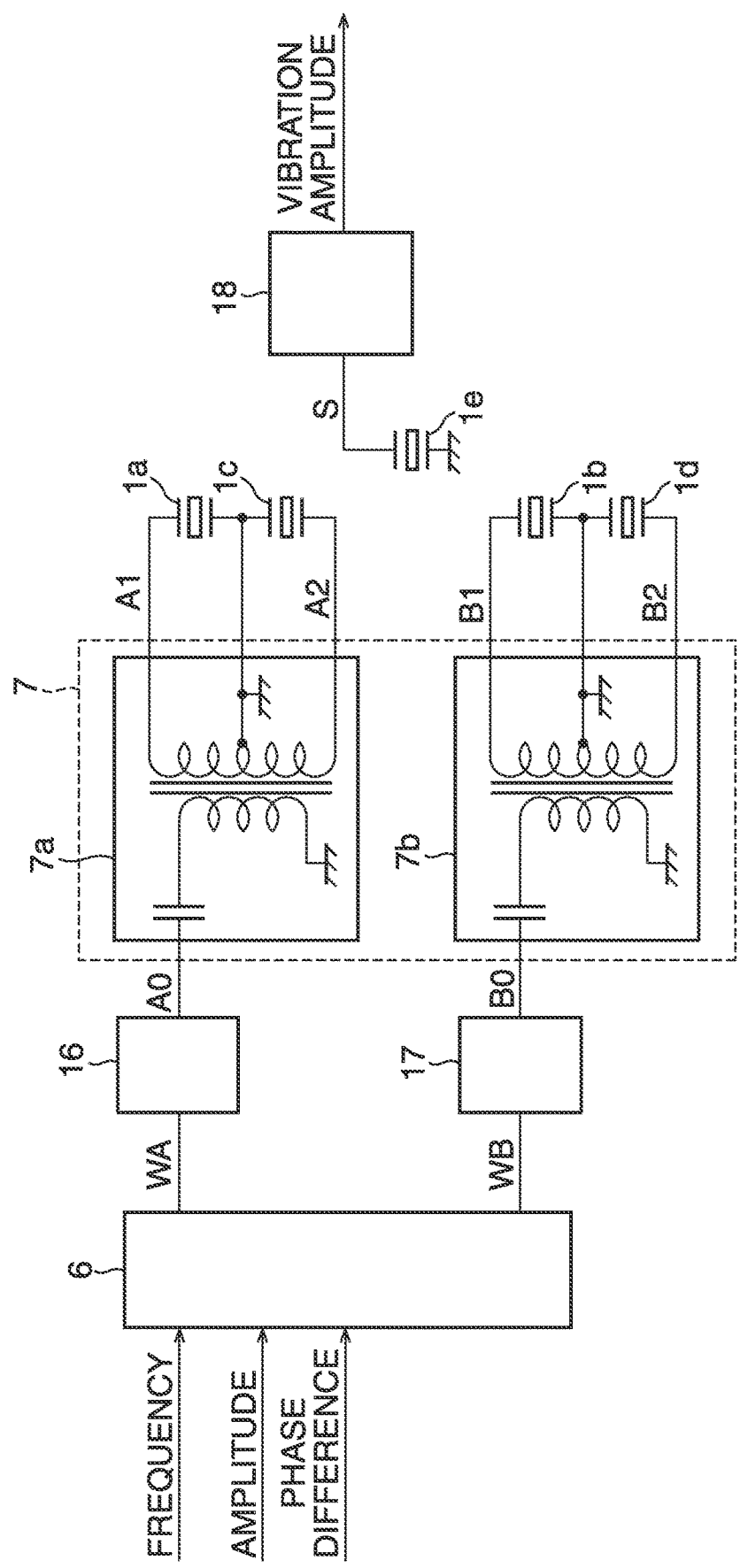
FIG. 10 is a diagram showing part of a circuit configuration of a variation of the controller shown in FIG. 2.
Figure 11:
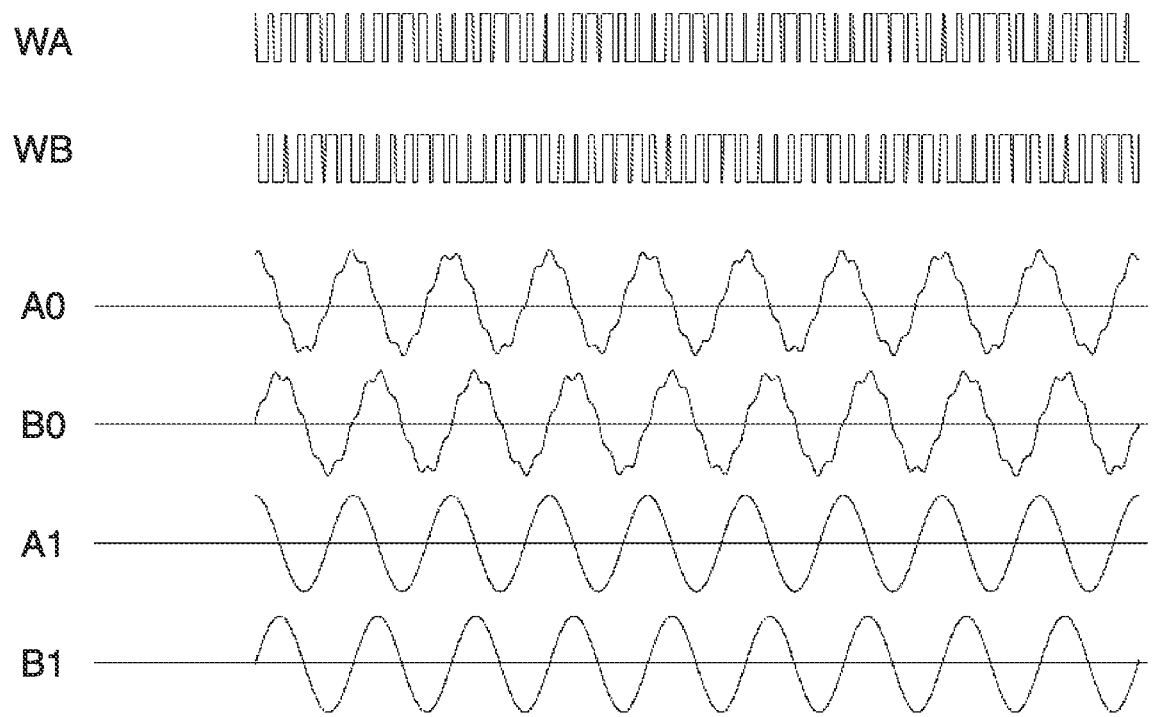
FIG. 11 is a diagram showing waveforms of input and output signals of a waveform generation circuit and an amplifier circuit appearing in FIG. 10.

FIG. 10 is a diagram showing a partial circuit configuration of the variation of the controller 150, including the waveform generation circuit 6, the amplifier circuit 7, and components around them. FIG. 11 is a diagram showing waveforms of input and output signals of the waveform generation circuit 6 and the amplifier circuit 7 shown in FIG. 10.

In general, the vibration actuator is driven at an AC voltage of a frequency not lower than 20 kHz for the purpose of avoiding audible sound. Further, the amplitude of the driving voltage for driving the vibration actuator is set to a wide range from several volts to several hundreds volts according to the form of the piezoelectric element, and a vibration actuator using a laminated piezoelectric element is capable of generating a large exciting force at a low voltage. On the other hand, to cause the piezoelectric element 1 in the form of a single annular plate to generate a desired exciting force as in the case of the vibration actuator 100, a voltage not lower than several tens volts is required. Therefore, in most cases, the vibration actuator is configured to include not only the waveform generation circuit, but also the amplifier circuit.

As shown in FIG. 11, the pulse signals WA and WB at approximately several volts, which are obtained by performing PWM (Pulse Width Modulation) on respective sine waves with a signal of several hundreds KHz, are smoothed by filters 16 and 17, whereby signals A0 and B0 are generated. The signals A0 and B0 are amplified by transformers 7a and 7b provided in the amplifier circuit 7, and are converted to the driving voltages A1 and B1 each having a smooth waveform by the filtering effect of the capacitance of the piezoelectric element 1 and the leakage inductance of an associated one of the transformers. Note that the transformers 7a and 7b each have a secondary intermediate tap connected to the electric ground, and also outputs the driving voltages A2 and B2 which are opposite in phase to the driving voltages A1 and B1, respectively. Thus generated AC driving voltages A1, B1, A2, and B2, which are shifted in phase by 90 degrees from one another, are applied to the electrodes 1a, 1b, 1c, and 1d of the piezoelectric element 1, respectively, whereby it is possible to generate a travelling vibration wave in the annular elastic body 8.

Figure 12:
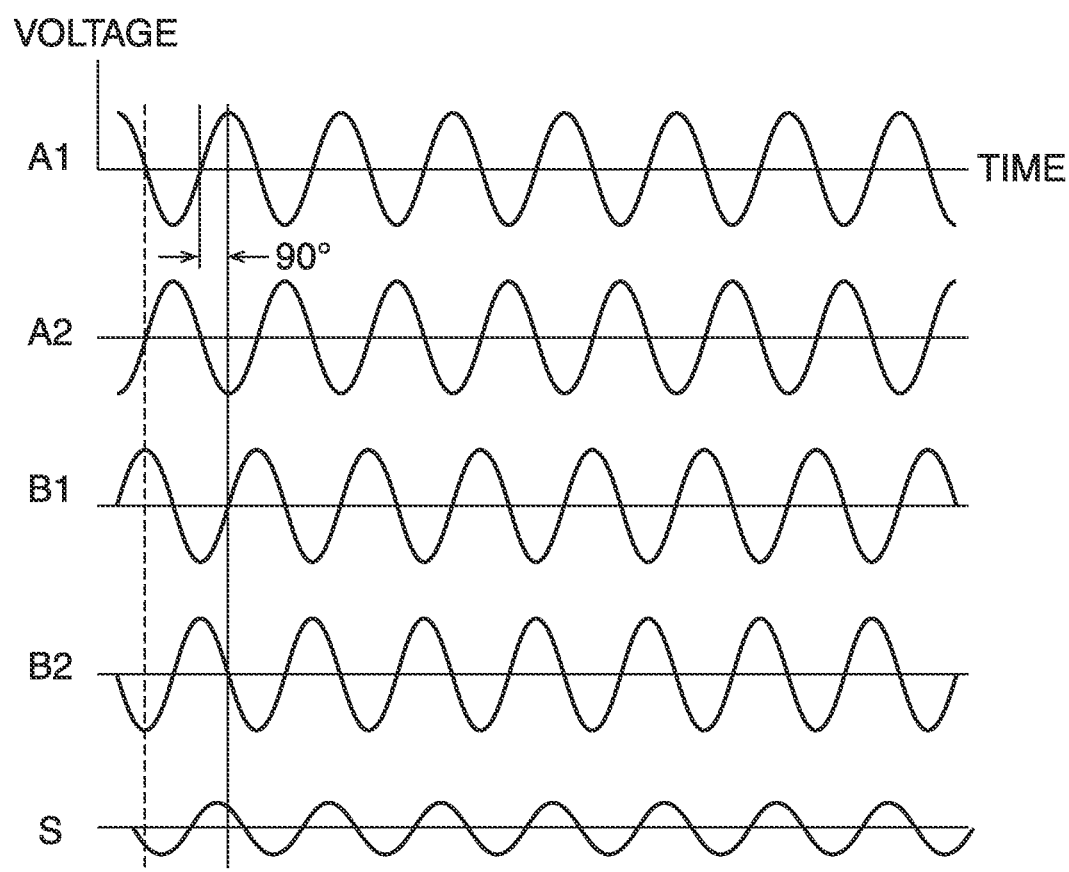
FIG. 12 is a diagram showing driving voltages applied to the piezoelectric element of the vibration actuator shown in FIG. 1 and a signal for detecting vibration, in a comparative manner.

The electrode 1e appearing in FIG. 10, as described with reference to FIG. 4, detects the magnitude (amplitude) of a vibration excited in the elastic body 8, and outputs a signal S of AC. FIG. 12 is a diagram showing the driving voltages A1, B1, A2, and B2, and the signal S, for comparison. The waveforms of the driving voltages A1, B1, A2, and B2, shown in FIG. 12, are the same as those shown in FIG. 3. The signal S is the same in frequency as the driving voltages A1, B1, A2, and B2, but is different in amplitude, and varies in amplitude and phase difference from the driving voltages A1, B1, A2, and B2, according to the frequencies of the driving voltages A1, B1, A2, and B2.

The amplitude of the signal S is detected by an RMS-DC conversion circuit 18. In the timing diagram shown in FIG. 8, the frequency band 1 is switched when a predetermined time period (T1) elapses after the CPU 5 decides to stop driving the vibration actuator 100. Alternatively, an output signal from the RMS-DC conversion circuit 18 may be observed to thereby switch the settings of the frequency band 1 after it is confirmed that the vibration amplitude of the elastic body 8 is equal to or lower than a predetermined amplitude. Further, although not shown, the configuration may be such that the RMS-DC conversion circuit 18 detects the amplitude of the driving voltage A1, and the settings of the frequency band 1 may be switched after it is confirmed that the amplitude of the driving voltage A1 is equal to or lower than a predetermined value.

Next, as a variation of the first embodiment, a description will be given of a case where the rotary encoder 2 outputs analog signals, i.e. a case where the analog signals AA1 and AB1 (see FIGS. 5A to 5D) output from the optical sensor 12 are directly output as the analog signals. In this case, the circuit configuration of the filter 3 is required to be changed.

Figure 13A:
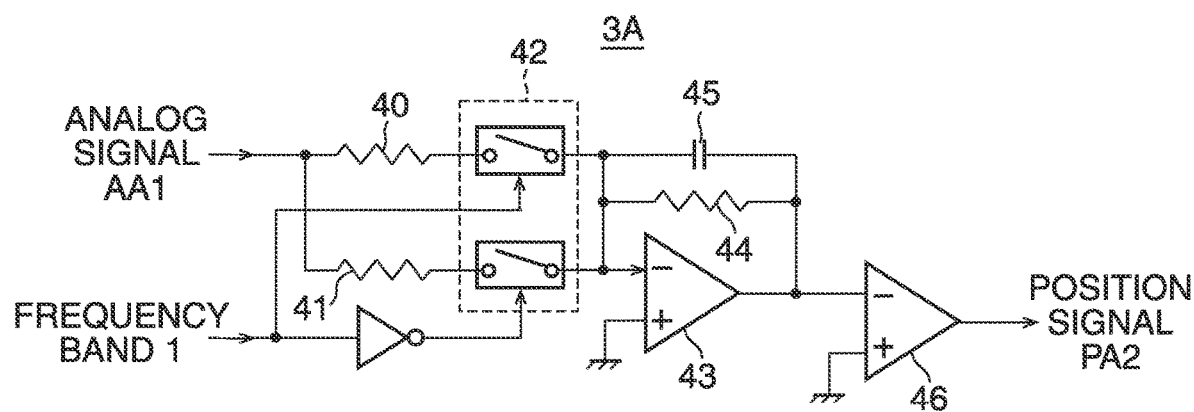
FIG. 13A is a circuit diagram of a first variation of the filter included in the controller shown in FIG. 2.

FIG. 13A is a circuit diagram of a filter 3A according to a first variation of the filter 3. Although FIG. 13A shows a circuit for processing the analog signal AA1, the filter 3A also includes the same circuit as the circuit shown in FIG. 13A as a circuit for processing the analog signal AB1.

The filter 3A is a low-pass filter formed by combining an OP amplifier 43, resistors 40, 41, and 44, and a capacitor 45. In the filter 3A, the resistors 40 and 41 are switched using an analog switch 42 according to the settings of the frequency band 1 to thereby switch the cut-off frequency. The filter 3A eliminates noise from the input analog signal AA1 (see FIGS. 5A to 5D), and converts the resulting signal with a noise-free waveform to a pulse signal using a comparator 46 to thereby output the position signal PA2.

Figure 13B:
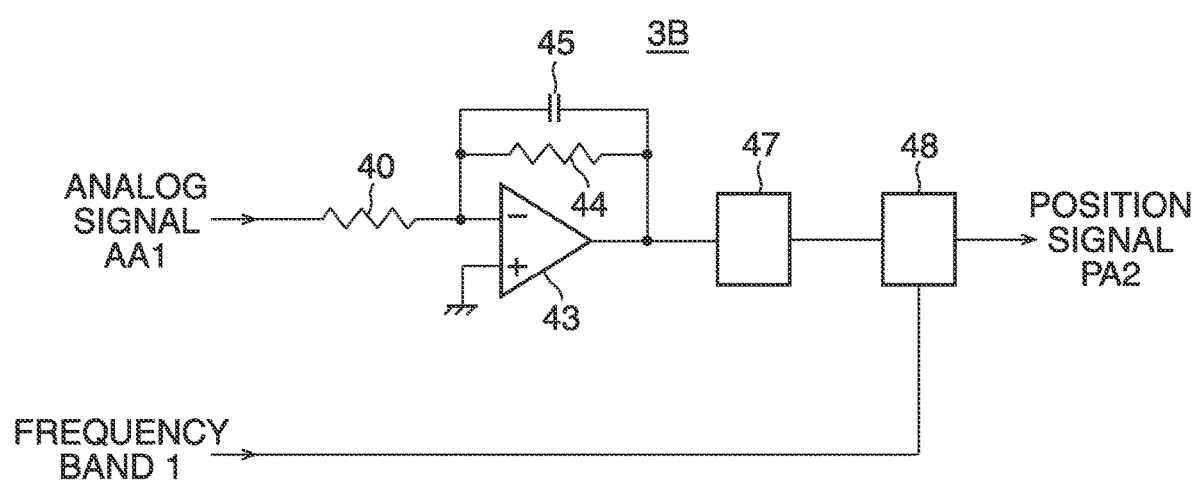
FIG. 13B is a circuit diagram of a second variation of the filter included in the controller shown in FIG. 2.

FIG. 13B is a circuit diagram of a filter 3B according to a second variation of the filter 3. Similar to the filter 3A, although FIG. 13B shows a circuit for processing the analog signal AA1, the filter 3B also includes the same circuit as the circuit shown in FIG. 13B as a circuit for processing the analog signal AB1.

The filter 3B has a circuit configuration in which a low-pass filter having a fixed frequency band, which is formed by combining the OP amplifier 43, the resistors 40 and 44, and the capacitor 45, is disposed upstream of an A/D converter 47. The cut-off frequency of the low-pass filter is set to such a high frequency which does not have adverse influence on the waveform of the analog signal AA1 and is also not higher than ½ of a sampling frequency of the A/D converter 47. Further, the cut-off frequency is changed by a digital filter 48 according to the settings of the frequency band 1 after A/D conversion.

The digital filter 48 may have any configuration insofar as it is a low-pass filter. For example, the digital filter 48 may be configured to convert analog signals to two-phase pulse signals, and then process the pulse signals using a circuit equivalent to the filter 3, or may be implemented by a known FIR filter, an IIR filter, or the like. This digital filter can accurately set a frequency band, and hence even in a case where filters are provided for the two-phase pulse signals, respectively, the filters can be configured to have same filter characteristics applied thereto.

Although in the first embodiment, the rotary encoder 2 is used as the position detection unit, the position detection unit may be a linear encoder. Further, although the optical sensor is used as the rotary encoder 2, even when a magnetic sensor or an electrostatic sensor is used, it has the same influence of noise or vibration on a position signal, and hence a magnetic sensor or an electrostatic sensor can be used in place of the optical sensor.

Further, in the first embodiment, the filter 3 is provided for the position signals PA1 and PB1 detected by using the optical scale 11, to thereby detect the rotation position or the like of the driven element 9. In place of this, by providing a filter for another signal output according to the position of the roller 15, the rotation position of the roller 15 may be detected. For example, a filter having the same characteristics as the filter 3 may be provided for an origin signal which becomes the high level only in a predetermined rotation section (origin position) once per one rotation of the roller 15. The filter generates the same delay with respect to all signals that change according to the rotation position of the roller 15, and hence it is possible to confirm the origin position with high accuracy.

In general, the origin signal is a signal for confirming the origin position which is a single point, and hence is often detected as a very narrow pulse signal. For this reason, there is a fear that the origin signal itself is cut off depending on the settings of the frequency band of the filter. To avoid this problem, it is necessary to increase the width of the frequency band or drive the driven element 9 for rotation at such a low speed at which the noise frequency components can be separated. Further, in a case where it is necessary to accurately detect the origin position in an environment having a lot of electromagnetic noise, it is preferable to confirm the correct position by performing confirmation of the origin position a plurality of times, and it is desirable to confirm the origin signal in a situation having as less electromagnetic noise as possible.

Further, although in the first embodiment, the description has been given of the drive control for the vibration actuator 100, insofar as the actuator is configured such that a driven element is held by a friction force (holding force) when the actuator is stopped, the drive control for the driven element can be performed by the controller 150. For example, an electromagnetic motor or the like which has a gear reduction mechanism has a certain holding force even when the power is switched off, and has a large dead band, and hence by performing the drive control therefor by the controller 150, it is possible to obtain the same advantageous effects as provided by the case where the driving of the vibration actuator 100 is controlled by the controller 150.

On the other hand, even when an actuator having a small force for holding the driven element is used, a merit can be obtained by the drive control performed by the controller 150 insofar as it is possible to obtain the holding force using another holding unit. However, in this case, the holding unit and the actuator are required to be operated in an interlocked manner, and its example will be described with reference to FIG. 14.

Figure 14:
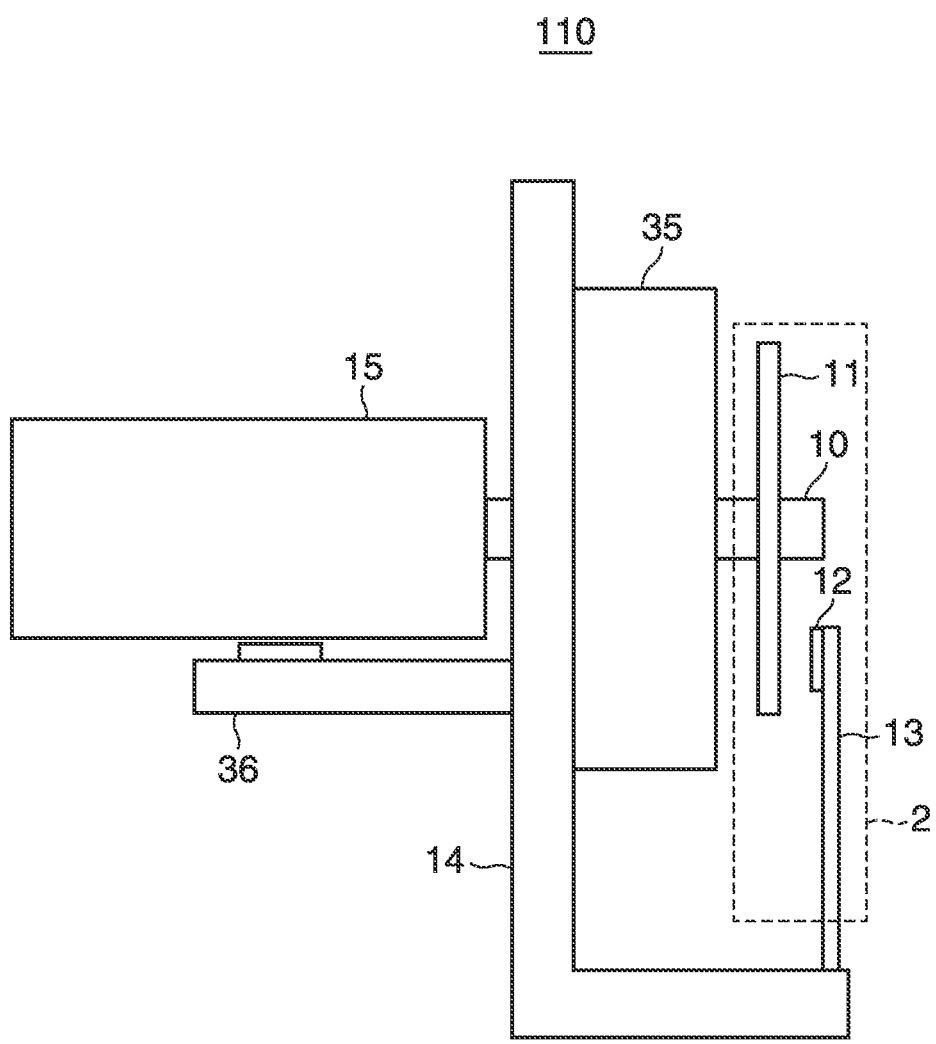
FIG. 14 is a diagram showing an example of an actuator having a brake added to a rotary driving system using a DC motor.

FIG. 14 is a diagram showing an example of an actuator 110 having a brake 36 (holding unit) added to a rotary driving system using a DC motor 35. The same components of the actuator 110 as those of the vibration actuator 100 shown in FIG. 1 are denoted by the same reference numerals, and description thereof is omitted.

In the actuator 110, the DC motor 35 is fixed on the support base 14, the rotary encoder 2 is fixed to one end of the output shaft 10 of the DC motor 35, and the roller 15 is fixed to the other end of the output shaft 10. Further, the brake 36 is fixed to the support base 14. The brake 36 includes a presser portion (brake pad) which can be pressed against an outer peripheral surface of the roller 15 in a radial direction of the roller 15. The brake 36 presses the presser portion against the outer peripheral surface of the roller 15 with a predetermined force according to a command from a controller, not shown, to thereby prevent the roller 15 from being rotated when the DC motor 35 is stopped (during power-off).

The CPU 5 of the controller 150 changes the frequency band 1 set in the filter 3 from the frequency band F11 for during driving to the frequency band F10 for during stopping after instructing the brake 36 to stop rotation of the roller 15 (to press the presser portion against the roller 15). On the other hand, when starting the DC motor 35, the CPU 5 changes the frequency band 1 set to the filter 3 from the frequency band F10 for during stop to the frequency band F11 for during driving before instructing the brake 36 to release the roller 15 from a state pressed by the presser portion. This makes it possible to effectively suppress the influence of external disturbances and noise, similarly to the case where the driving of the vibration actuator 100 is controlled by the controller 150.

Next, a description will be given of a second embodiment of the present invention. In the controller 150 according to the first embodiment, the filter 3 is inserted for the two-phase position signals having a frequency proportional to the rotation speed of the driven element 9. On the other hand, in the second embodiment, a controller configured is such that a filter is inserted for a position signal having a value corresponding to a rotation position.

Figure 15:
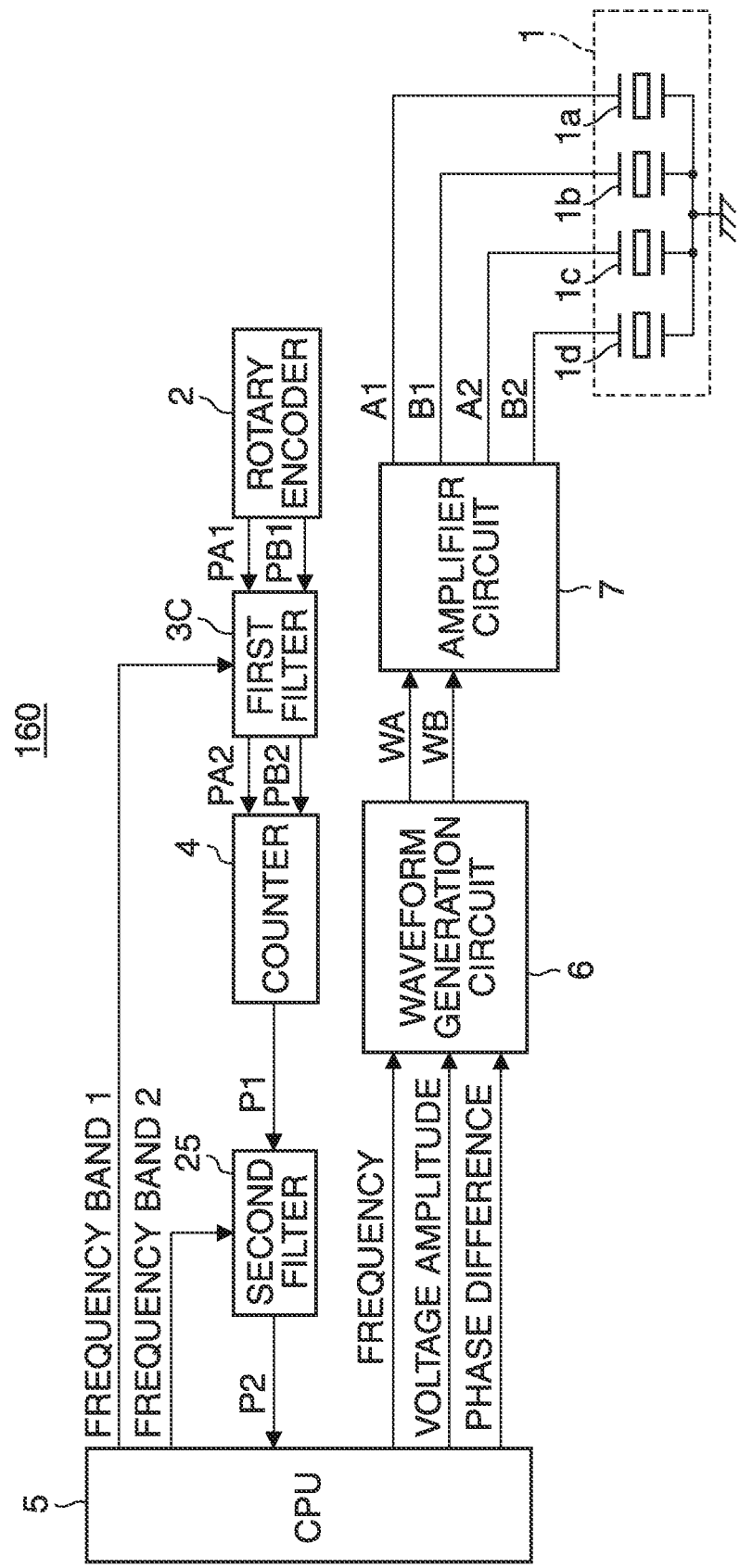
FIG. 15 is a schematic block diagram of a controller according to a second embodiment of the present invention.

FIG. 15 is a schematic block diagram of the controller, denoted by reference numeral 160, according to the second embodiment. In the present embodiment, the description is given assuming that a target of driving control of the controller 160 is the vibration actuator 100 shown in FIG. 1. The controller 160 differs from the controller 150 in that the filter 3 of the controller 150 is replaced by a first filter 3C, and a second filter 25 is provided which converts the position signal P1 input from the counter 4 to a position signal P2 and outputs the position signal P2 to the CPU 5. Therefore, the same components of the controller 160 as those of the controller 150 are denoted by the same reference numerals, and description thereof is omitted.

The first filter 3C included in the controller 160 is substantially the same as the filter 3 included in the controller 150. Therefore, the basic operation of the first filter 3C has already been described in the first embodiment, and hence description thereof is omitted.

The second filter 25 generates a position signal P2 from a position signal P1 based on a frequency band 2 instructed by the CPU 5, and outputs the generated position signal P2 to the CPU 5. The frequency band 1 set in the first filter 3C and the frequency band 2 set in the second filter 25 both include 0 Hz, and the frequency band 2 is set to be narrower than the frequency band 1.

The controller 160 is characterized in that the two filters of the first filter 3C and the second filter 25 are connected in series, whereby the different frequency bands can be set in the first filter 3C and the second filter 25 by the CPU 5, respectively. In this case, although the effect obtained by combining the first filter 3C and the second filter 25 is the same as that provided by the first embodiment, it is possible, by role sharing between them, to improve the performance of cutting off noise caused by electromagnetic noise and mechanical vibration, from the position signals PA1 and PB1. The first filter 3C has a role of cutting off electromagnetic noise, and the second filter 25 has a role of cutting off noise caused by mechanical vibration, with the frequency bands 1 and 2 properly set according to the respective roles.

Figure 16:
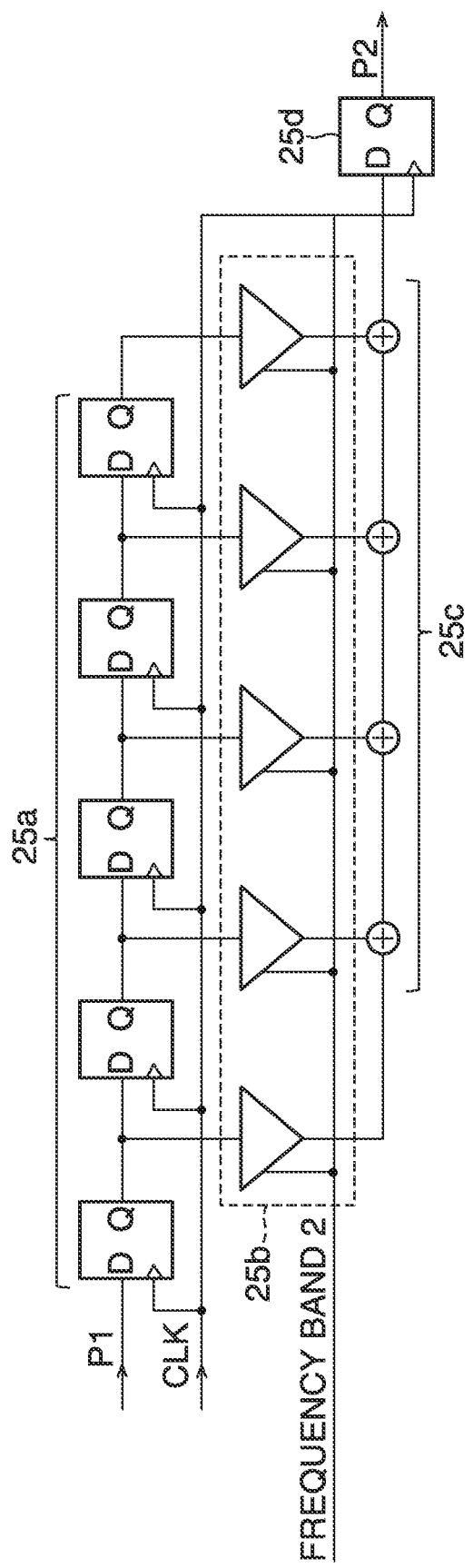
FIG. 16 is a circuit diagram of a second filter as a component of the controller shown in FIG. 15.

FIG. 16 is a circuit diagram of the second filter 25. The second filter 25 is a so-called FIR filter, and has a function as a low-pass filter in the present embodiment. The second filter 25 includes a resistor group 25a, a multiplier 25b, an adder 25c, and a resistor 25d. The resistor group 25a has an arrangement in which five resistors that latch the position signal P1 in synchronism with the CLK signal are connected in series, and the resistors hold respective states of the position signal P1 (e.g. a 16-bit digital signal) obtained at five different times, respectively. The multiplier 25b outputs values obtained by multiplying outputs from the five resistors of the resistor group 25a by a value stored in advance according to the frequency band 2 set from the outside. The adder 25c outputs a result of adding up the five outputs from the multiplier 25b. The resistor 25d latches the output from the adder 25c, and outputs the latched value as a position signal P2.

Figure 17:
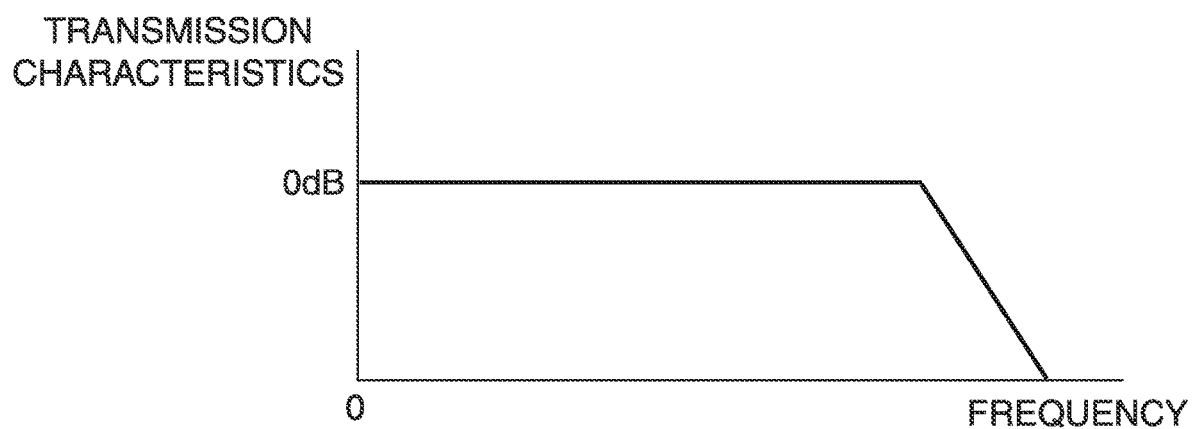
FIG. 17 is a diagram showing an example of frequency characteristics of the second filter shown in FIG. 15.

FIG. 17 is a diagram showing an example of frequency characteristics of the second filter 25. The filter having such characteristics can be implemented by another configuration, and further, the configuration of the second filter 25 is not limited to that shown in FIG. 16. For example, the second filter 25 may be implemented by an IIR filter or a filter using FFT calculation. Although the method used for the case where the origin signal is detected has been described in the first embodiment, the origin signal indicates only a certain single point, and hence the filtering effect cannot be obtained from the second filter 25. Therefore, it is necessary to use only the first filter 3C for the origin signal, similarly to the filter 3 of the controller 150.

Next, the frequency bands 1 and 2 set in the first filter 3C and the second filter 25, respectively, will be described. In the present example, it is assumed that the first filter 3C has the same circuit configuration as that of the filter 3 shown in FIGS. 6A and 6B. In this case, the first filter 3C has a capability of cutting off all pulses narrower than a predetermined pulse width, and hence in a case where the frequency band of the position signal PA1 and the frequency band of noise is close to each other, if the noise is cut off, the position signal PA1 may be cut off together. To avoid this problem, the frequency band 1 set in the first filter 3C is set in a manner having a sufficient margin with respect to the frequency band of the position signal PA1.

As described with reference to FIGS. 5A to 5D, the influences of electromagnetic noise on the position signals PA1 and PB1 have some patterns depending on the magnitude of noise. In a case where the magnitude of noise is small, only one of the position signals PA1 and PB1 undergoes a spike-like change which is quickly restored. If such noise is generated, the position signal shows a change corresponding to movement by one count, but quickly returns to the original state, and hence a position error is not accumulated, and even if the first filter 3C ignores the noise, the noise can be eliminated by the second filter 25 disposed downstream of the first filter 3C.

Therefore, first, the operation of the controller 160 will be described only with respect to a case where the vibration actuator 100 and the controller 160 are used in an environment where relatively small electromagnetic noise is caused, and the noise is superimposed on only one of the position signals PA1 and PB1 within the same time period of the position signals PA1 and PB1.

FIG. 18 is a diagram showing an example of setting patterns of the frequency band, for use in the environment where small electromagnetic noise is caused. The frequency bands Fr1, Fr2, Fr3, and Fr4 are set as different frequency bands as described below, respectively, in the decreasing order of the width of the frequency band of Fr4<Fr3<Fr2<Fr1.

Fr1: frequency band for eliminating spike-like noise having a narrow pulse width Fr2: frequency band of the position signal PA1 for during high-speed driving of the vibration actuator Fr3: frequency band of the position signal PA1 for during low-speed driving of the vibration actuator Fr4: frequency band lower than the natural frequency during the stopping of the vibration actuator Ranges set for the frequency band 1 and the frequency band 2 for during the driving of the vibration actuator 100 and for during the stopping thereof and the total frequency band are determined using these four frequency bands Fr1, Fr2, Fr3, and Fr4.

The example of configuration of the patterns 1 to 4 shown in FIG. 18 is a typical example, and this is not limitative. In the patterns 1 to 4, the frequency band, in total, for during stopping is narrower than the frequency band for during driving, and the reason for this configuration is the same as that in the first embodiment. Further, in FIG. 18, each entry indicated by a hyphen (-) indicates that no frequency band is set and an input signal is directly passed. The patterns 1 to 4 have similar effects, and differences between them will be described hereafter.

Under the condition of an environment where small electromagnetic noise is caused, the noise is not superimposed on both of the position signals PA1 and PB1 during the same time period, and hence an error is not accumulated in the counter 4. Therefore, even when noise is superimposed on the position signal P2 during the driving of the vibration actuator 100, this does not eventually leads to a shift in the position where the driven element 9 is stopped. For this reason, in the patterns 1 and 2, the total frequency band for during the driving of the vibration actuator 100 is set to the frequency band Fr1, and mixing of noise corresponding to the frequency band Fr2 is allowed.

In the patterns 3 and 4, the total frequency band for during the driving of the vibration actuator 100 is set to the frequency band Fr2. In doing this, to prevent the position signal PA1 from being cut off by the first filter 3C during high-speed driving of the vibration actuator 100, the frequency band Fr2 is applied to the frequency band 2 set in the second filter 25. This makes it possible to improve the noise cut-off performance obtained during the driving of the vibration actuator 100, compared with the patterns 1 and 2.

In all of the patterns 1 to 4, the total frequency band for during the stopping of the vibration actuator 100 is set to the frequency band Fr4. This makes it possible to suppress mixing of noise corresponding to the frequency band Fr2 and influence of noise caused by external mechanical vibration, and thereby stably maintain a stopped state of the vibration actuator 100. Further, in the pattern 4, the frequency band 1 is set to the frequency band Fr2. This makes it possible to also cut off all noise corresponding to the frequency band Fr2 during the stopping of the vibration actuator 100, and hence it is possible to further increase stability during stopping.

Figure 19:
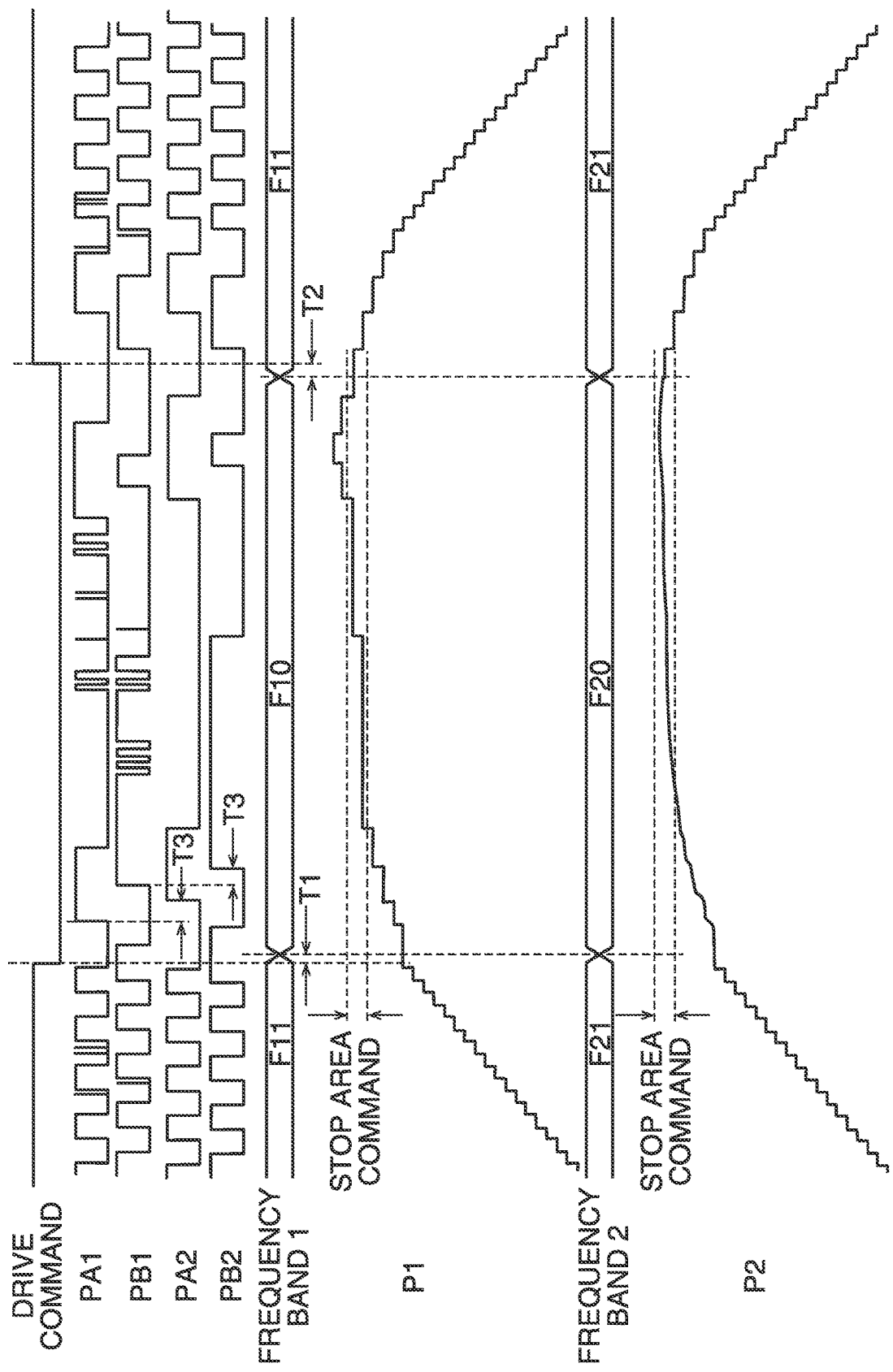
FIG. 19 is an example of a timing diagram useful in explaining the control of driving of the vibration actuator, which is performed by the controller shown in FIG. 15.

FIG. 19 is a timing diagram useful in explaining the control of driving of the vibration actuator 100, which is performed by the controller 160. Similarly to FIG. 8, FIG. 19 shows various signal waveforms observed from when the vibration actuator 100 is being driven, vi a drive stop time period, until after the vibration actuator 100 is restarted.

The vibration actuator 100 is subjected to constant speed control at the minimum speed (Vmin) during driving immediately before the stop of driving, and the frequency band 1 of the first filter 3C is set to the frequency band F11 (=Fr1). Therefore, the first filter 3C cuts off only spike-like noise superimposed on the position signals PA1 and PB1, and outputs the position signals PA2 and PB2. Further, the frequency band 2 of the second filter 25 is set to a frequency band F21 (=no filter). Therefore, the second filter 25 directly outputs the position signal P1 input thereto as the position signal P2. Therefore, the position signal P2 increases at a constant rate in a stepped manner during driving immediately before the stop of driving.

When the position signal P2 comes closer to a predetermined distance from the range of the stop area command, the CPU 5 decides to stop driving of the vibration actuator 100, and sets the drive command to the low level. Further, the CPU 5 outputs a command to the waveform generation circuit 6 for setting the amplitude of the driving voltage to 0 [V]. Although in the first embodiment, waveforms formed by performing PWM (Pulse Width Modulation) on sine waves are used for output signals from the waveform generation circuit 6, in the second embodiment, analog sine waves or simple signals having a fixed pulse width may be used. Note that in a case where the signals having a fixed pulse width are used, the pulse width is set in place of the voltage amplitude, and the pulse width is set to zero (0) when stopping the driving of the vibration actuator 100.

Upon receipt of this command, the waveform generation circuit 6 stops outputting the pulse signals WA and WB. As a result, the amplitude of the driving voltages A1, B1, A2, and B2 becomes equal to 0 [V], and the driving of the vibration actuator 100 is stopped. The CPU 5 switches the frequency band 1 from the frequency band F11 to the frequency band F10 (=Fr2) when a predetermined time period (T1) elapses after setting the drive command to the low level, and switches the frequency band 2 from the frequency band F21 to the frequency band F20 (=Fr4). The frequency band F10 includes the frequency of the position signals PA1 and PB1 immediately before the stop of driving, and hence the first filter 3C does not cut off the position signals PA1 and PB1 in a region where the speed is being reduced after setting the voltage amplitude to 0 [V]. On the other hand, the first filter 3C cuts off not only spike-like noise, but also noise having somewhat wide pulse width. Further, the frequency band F20 is a band lower than the natural frequency of the natural vibration mode of the vibration actuator 100, and hence even when the position signal P1 goes out of the range of the stop position command due to an influence of noise caused by mechanical vibration, the position signal P2 is held within the range of the stop position command.

After a predetermined stop time period elapses, the CPU 5 restarts the vibration actuator 100 based on a position command from the command means, not shown. When the CPU 5 decides to restart the vibration actuator 100, the CPU 5 switches the frequency band 1 from the frequency band F10 to the frequency band F11 a predetermined time period before (T2) the change of the drive command from the low level to the high level, and switches the frequency band 2 from the frequency band F20 to the frequency band F21. Then, the CPU 5 sets the frequency, the voltage amplitude, and the phase difference to predetermined values for the waveform generation circuit 6, and restarts the vibration actuator 100. The operation performed after the restart is the same as that in the first embodiment, and hence description thereof is omitted.

In the timing diagram shown in FIG. 19, the position signal P2 is held within the range of the stop area command during the stopping of the vibration actuator 100. In contrast, the following description will be given of a process performed in a case where the position signal P2 goes out of the range of the stop area command due to an influence of noise caused by mechanical vibration during the stopping of the vibration actuator 100, with reference to FIG. 20.

Figure 20:
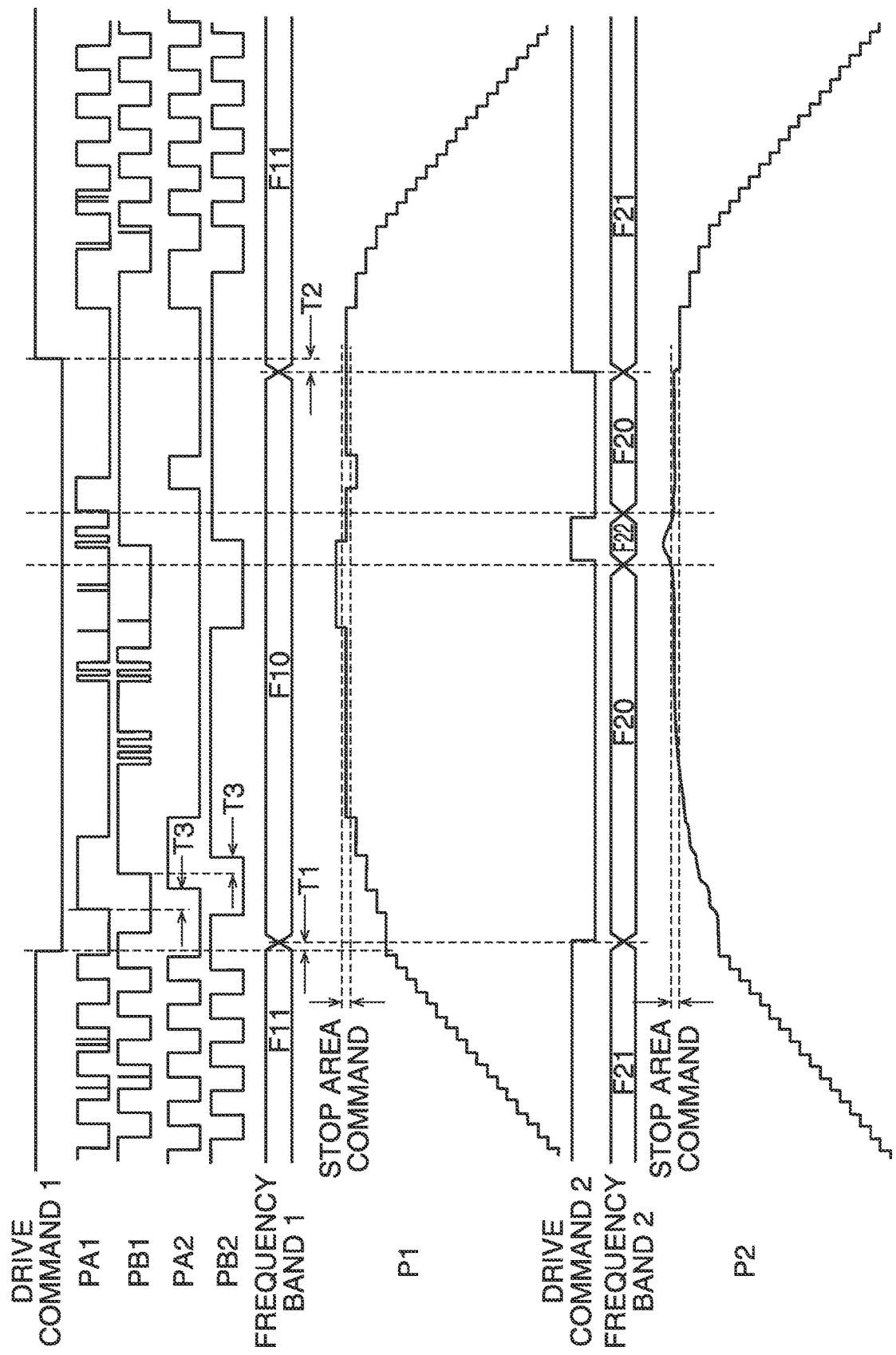
FIG. 20 is another example of the timing diagram useful in explaining the control of driving of the vibration actuator, which is performed by the controller shown in FIG. 15.

FIG. 20 is another example of the timing diagram useful in explaining the control of driving of the vibration actuator 100, which is performed by the controller 160. FIG. 20 shows various signal waveforms observed from when the vibration actuator 100 is being driven, via a drive stop time period, until after the vibration actuator 100 is restarted, similarly to FIG. 8. The frequency band F11, the frequency band F10, the frequency band F21, and the frequency band F20 in FIG. 20 correspond to the frequency band Fr1, the frequency band Fr2, a band without filtering, and the frequency band Fr4, respectively. Further, as a frequency band F22, a band, for example, which satisfies the condition of a frequency band wider than the frequency band Fr4 and narrower than the frequency band Fr2 (Fr4<f<Fr2 (f: frequency)) is used.

The operations performed before the stop and after the restart of the vibration actuator 100 in the timing diagram in FIG. 20 are the same as those described with reference to FIG. 19, and hence the description is given only of the operation performed during the stopping of the vibration actuator 100. When the position signal P2 goes out of the range of the stop area command, the CPU 5 changes the drive command to the high level, sets the frequency, the voltage amplitude, and the phase difference to predetermined values for the waveform generation circuit 6, and restarts the vibration actuator 100. By changing the frequency band 2 from the frequency band F20 to the frequency band F22 while maintaining the frequency band 1 at the frequency band F10, the CPU 5 starts control such that the position signal P2 returns into the range of the stop area command. Then, when the position signal P2 enters the range of the stop area command again, the CPU 5 changes the drive command to the low level, sets the voltage amplitude to 0 [V], and returns the frequency band 2 from the frequency band F22 to the frequency band F20.

The frequency band 2 is set not to the frequency band F21 but to the frequency band F22 when restarting the vibration actuator 100 during the stopping of the vibration actuator 100, as described above, because the response characteristics are different between driving by a minute amount during the stopping of the vibration actuator 100 and normal driving. For this reason, considering a balance of requirements for immediately returning the value of the position signal P2 into the range of the stop area command and suppressing a shock (mechanical vibration) at the start, the frequency band F22 is set to values between the frequency band F21 and the frequency band F20.

In the second embodiment, as described above, the first filter 3C and the second filter 25 shares the role for eliminating noise. With this, noise which cannot be suppressed by the first filter 3C or noise caused by large mechanical vibration can be suppressed by the second filter 25. Further, also in the second embodiment, similar to the first embodiment, the total frequency band by the first filter 3C and the second filter 25 is set to different bands between when driving the vibration actuator 100 and when stopping the vibration actuator 100, and the band for during stopping is set to be narrower. This makes it possible to effectively improve the performance of cutting off noise during stopping without lowering controllability during the driving of the vibration actuator 100.

The above description has been given based on a precondition of a situation where the amplitude of electromagnetic noise is relatively small, and noise is not superimposed on both of the position signals PA1 and PB1 in the same time period. Next, a description will be given of the control performed when the noise level is high, or when noise is not sporadic but is continuously superimposed on the position signals PA1 and PB1.

As described with reference to FIGS. 5A to 5D, in the environment in which large electromagnetic noise is caused, noise is sometimes superimposed on the position signals PA1 and PB1 almost simultaneously. In this case, unless noise is eliminated, a possibility that position errors are accumulated is increased.

In a case where a frequency band of high-level noise corresponds to the frequency band Fr1, by directly applying the circuit configuration of the filter 3 shown in FIGS. 6A and 6B to the first filter 3C, and setting one of the patterns 1, 2, and 3 shown in FIG. 18, it is possible to avoid accumulation of position errors. This is because even when noise is simultaneously superimposed on both of the position signals PA1 and PB1, by performing filtering processing on each signal in the frequency band Fr1, noise can be cut off.

When a frequency band of high-level noise corresponds to the frequency band Fr2, to cut off the noise using the first filter 3C, it is necessary to set the upper limit frequency of the frequency band 1 to be lower than the upper limit frequency of the frequency band Fr2. With this configuration, however, the position signals PA1 and PB1 during high-speed driving of the vibration actuator 100 are cut off. On the other hand, the noise substantially simultaneously superimposed on the position signals PA1 and PB1 may cause position errors to be accumulated, and it is impossible to prevent accumulation of position errors even when the second filter 25 is used.

Therefore, to cut off noise of high level corresponding to the frequency band Fr2 using the first filter 3C, the frequency of the position signals PA1 and PB1 during high-speed driving of the vibration actuator 100 is required to be sufficiently lower than the frequency band of noise. To this end, the circuit configuration of the filter 3 shown in FIGS. 6A and 6B is changed to a circuit configuration shown in FIG. 21, and the resulting circuit configuration is applied to the first filter 3C.

Figure 21:
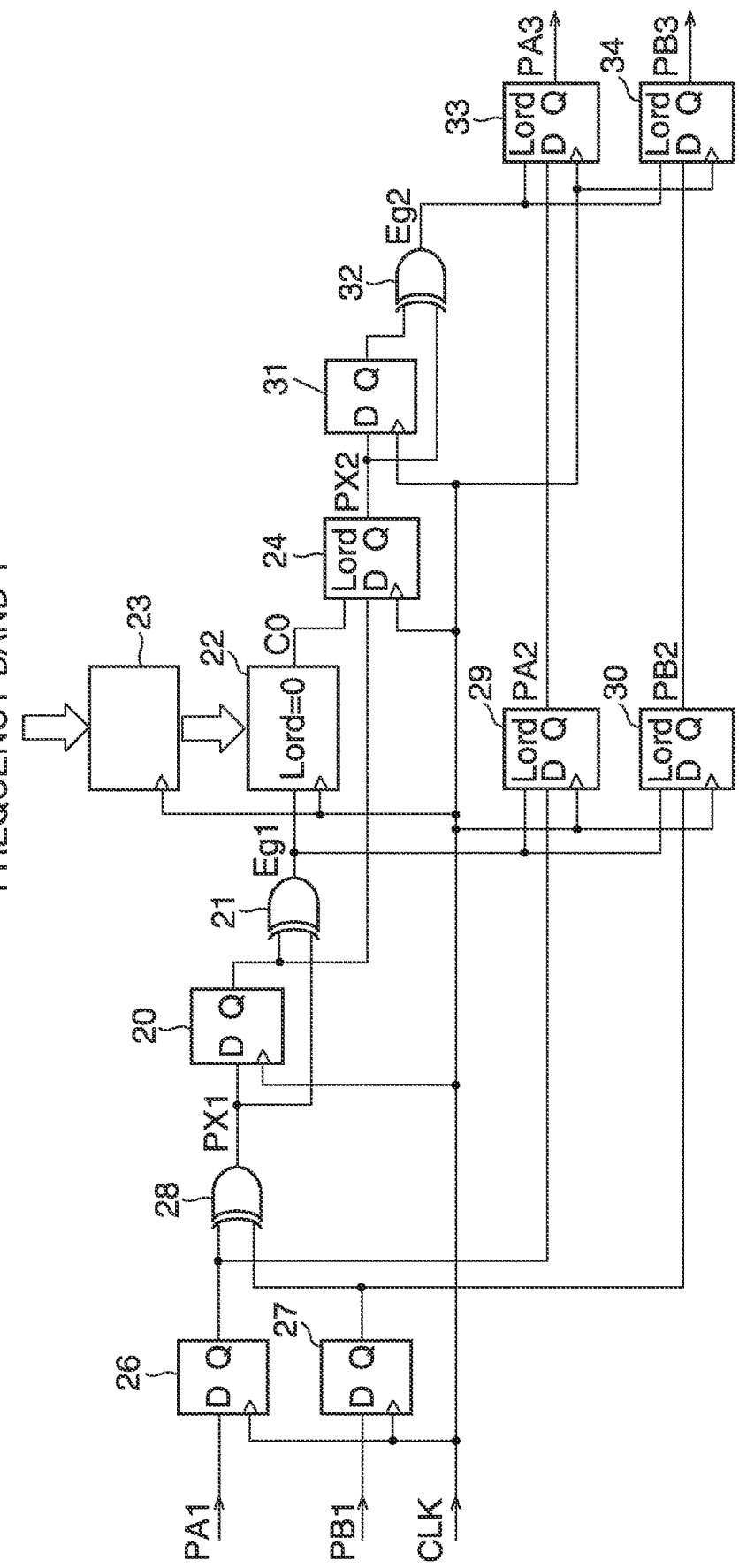
FIG. 21 is a circuit diagram showing an example of circuit configuration of a first filter as a component of the controller shown in FIG. 15.
Figure 22A:
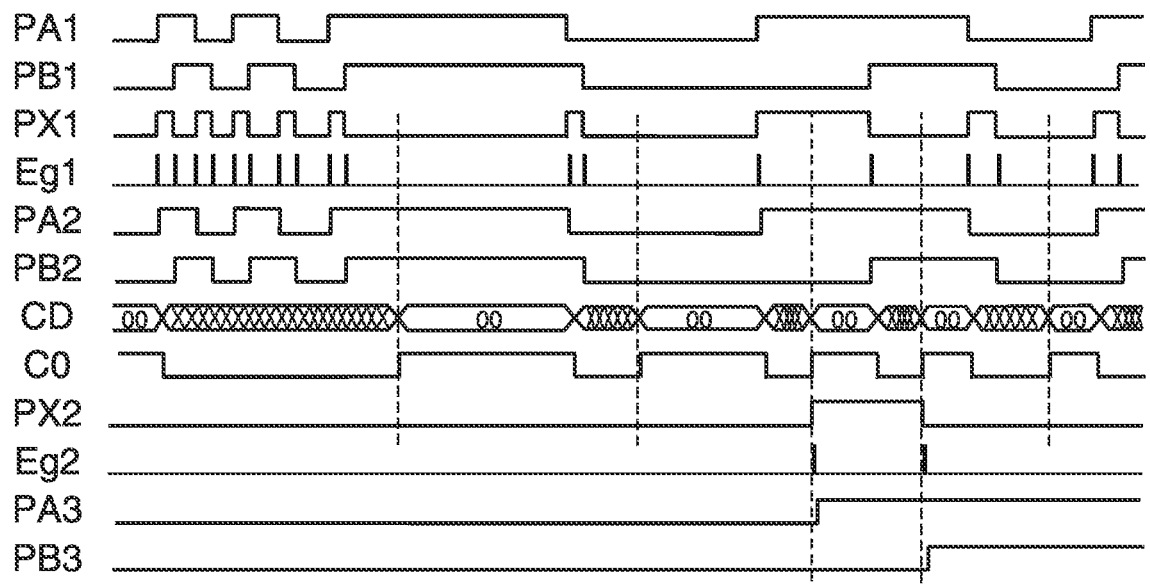
FIGS. 22A and 22B are timing diagrams each showing operation waveforms in the filter circuit shown in FIG. 21.
Figure 22B:
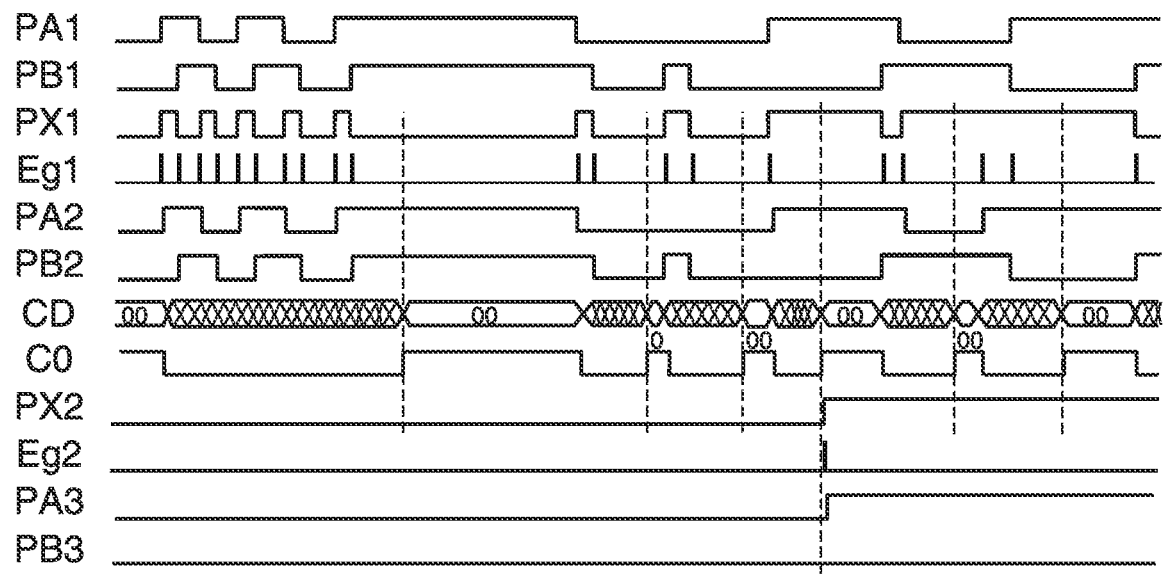

FIG. 21 is a circuit diagram showing an example of the circuit configuration of the first filter 3C (hereinafter referred to as the "filter circuit 3Ca"). The filter circuit 3Ca is designed to cope with the situation in which noise is substantially simultaneously superimposed on both of the position signals PA1 and PA2, and the filter 3 shown in FIGS. 6A and 6B can be replaced by the filter circuit 3Ca. FIGS. 22A and 22B are timing diagrams showing waveforms of signals in the filter circuit 3Ca and each showing a filter operation performed on a different input signal pattern.

The filter circuit shown in FIGS. 6A and 6B acts on a phase-by-phase basis independently, but the filter circuit 3Ca shown in FIG. 21 acts as a filter in a manner coping with changes in two-phase signals. The filter circuit 3Ca measures an interval between two changes of the position signals PA1 and PB1, irrespective of whichever of the position signals PA1 and PB1 each change belongs to, and if the measured interval is shorter than a predetermined time period, the filter circuit 3Ca ignores the changes to thereby operate as a filter. That is, the filter circuit 3Ca functions so as to prevent narrow pulse-like noise caused by two changes in one signal and noise caused by respective substantially simultaneous changes of two signals, from passing as signals.

The filter circuit 3Ca includes the D-type flip flop 20, the exclusive-OR element 21, the counter 22, the register 23, the latch 24, D-type flip flop circuits 26 and 27, an exclusive-OR element 28, and latches 29 and 30. Further, the filter circuit 3Ca includes a D-type flip flop 31, an exclusive-OR element 32, and latches 33 and 34. Note that the same components of the filter circuit 3Ca as those of the filter circuit shown in FIGS. 6A and 6B are denoted by the same reference numerals, and description thereof is omitted.

In the filter circuit 3Ca, the D-type flip flop circuits 26 and 27 latch the position signals PA1 and PB1 in synchronism with the CLK signal, respectively. The exclusive-OR element 28 generates a signal PX1 that is inverted whenever one of the position signals PA1 and PB1, latched by the D-type flip flop circuits 26 and 27, is changed. However, the signal PX1 is not inverted when the position signals PA1 and PB1 are simultaneously changed. That is, the signal PX1 is a signal including all changing points except a changing point at which the position signals PA1 and PB1 are simultaneously changed. An edge detection circuit formed by the D-type flip flop circuit 20 and the exclusive-OR element 21 detects a change in the signal PX1, and generates a narrow pulse-like signal Eg1. The resistor 23 holds settings of the frequency band 1 set by the CPU 5.

The counter 22 reads the settings of the frequency band 1 held by the resistor 23 whenever the signal Eg1 is input. Then, the counter 22 decrements the count CD by one whenever the CLK signal is input, and determines whether or not an interval between two changes of the position signal PA1 or PB1 is longer than an interval dependent on the settings of the frequency band 1. The counter 22 continues counting down until the signal Eg1, which is a pulse-like signal, is input, and when the count CD is reduced to 0, the counter 22 determines that the interval is sufficiently long, and sets the signal C0 to a high level. The counter 22 stops counting down as long as the signal C0 is at the high level. If it is determined that the interval between two changes of the position signal PA1 or PB1 is shorter than the interval dependent on the settings of the frequency band 1, the counter 22 sets the signal C0 to a low level.

A valid edge detection circuit formed by the latch 24, the D-type flip flop circuit 31, and the exclusive-OR element 32 causes, only when the signal C0 is at the high level, a signal formed by delaying the signal PX1 by one CLK signal pulse at the D-type flip flop circuit 20 to pass therein to thereby form a signal PX2, and causes a signal edge of the signal PX2 to be output as a narrow pulse-like signal Eg2. With this, the signal Eg2 becomes a signal indicative of the timing of a valid change of the position signal PA1 or PB1.

On the other hand, whenever the position signals PA1 and PB1 latched by the D-type flip flop circuits 26 and 27 are changed, changed values are stored in the latches 29 and 30, and are output as position signals PA2 and PB2, respectively. Then, the position signals PA2 and PB2 are latched by the latches 33 and 34 whenever the signal Eg2 indicative of a valid changing point is input, and the position signals at the valid changing point are output as position signals PA3 and PB3, respectively.

Therefore, by applying the filter circuit 3Ca to the first filter 3C, even when noise has a wide pulse width, in a case where the position signals PA1 and PB1 are changed substantially simultaneously, it is possible to cut off the noise with the settings of the frequency band for noise having a narrow pulse width.

On the other hand, when not sporadic noise but continuous noise having a high frequency is superimposed on the position signals PA1 and PB1, changes in the position signals PA1 and PB1 are buried in noise, and hence if noise is cut off, the position signals PA1 and PB1 are also cut off together.

In this case, it is necessary to provide a well-known low-pass filter or a notch filter that attenuates a specific frequency at a location upstream of the filter circuit 3Ca irrespective of whether the filter is an analog type or a digital type. After separating the position signals PA1 and PB1 from continuous specific noise using such a filter, the filter having the circuit configuration shown in FIG. 6A, 6B or 21 may be used. In a case where noise and the position signals PA1 and PB1 cannot be separated, to prevent noise from entering, it is further necessary to provide a countermeasure, such as provision of an electromagnetic shield.

Further, also in a case where the position signals PA1 and PB1 are influenced by continuous high-frequency mechanical vibration, the filter circuit shown in FIG. 6A, 6B or 21 cannot be used. This is because similarly to the case of continuous high-frequency noise, if noise caused by continuous high-frequency mechanical vibration is cut off by the filter circuit having the circuit configuration shown in FIG. 6A, 6B or 21, all the changes are cut off.

Although the same method used for continuous high-frequency noise is sometimes effective against noise caused by continuous high-frequency mechanical vibration, but in this case, the following points are required to be noted. That is, in the case of electromagnetic noise, it is considered that noise is simply added to a position signal, but mechanical vibration acts as phase modulation on a position signal, and hence noise caused by mechanical vibration cannot be handled as simple addition. In the case of phase modulation, a signal in a wide frequency range other than the frequency of the mechanical vibration is added to the position signal, and the frequency range extends over a wide range particularly in a case where the vibration amplitude is large, and hence it is difficult to estimate the frequency band.

To cope with this, noise caused by continuous high-frequency mechanical vibration is not eliminated at a location upstream of the first filter 3C, but is eliminated by the second filter 25 after being converted to a movement amount by the counter 4. In doing this, in the first filter 3C, the frequency band 1 is set so as to cut off only noise having higher frequency than the frequency of continuous mechanical vibration, and noise caused by continuous high-frequency mechanical vibration is cut off with the settings of the frequency band 2.

Next, as an example of an application which is influenced by the above-described various noise, a description will be given of the controller 160 of the vibration actuator 100 operating during MRI measurement in a bore of an MRI diagnostic apparatus. Since the vibration actuator 100 does not use a magnetic force, the vibration actuator 100 has less influence on the MRI measurement, and is suitable for an actuator used in the MRI diagnostic apparatus. In the MRI diagnostic apparatus, a minute high-frequency magnetic field is detected, and on the other hand, a very strong static magnetic field and a varying magnetic field (a sporadic high-frequency magnetic field and a gradient magnetic field which have a frequency not lower than 10 MHz) are generated at various timings. For this reason, an electronic device and a controller placed in the MRI bore are required not to disturb a high-frequency magnetic field and a static magnetic field to be detected, and not to erroneously operate in a varying magnetic field generated.

If the rotary encoder 2 is disposed in such an environment where a magnetic field is generated, the following influence is caused: noise superimposed on a signal of an electric circuit of the controller 160 includes relatively small sporadic high-frequency noise, and spike-like noise having a frequency of approximately several kHz caused by an influence of a gradient magnetic field, and the latter spike-like noise has a particularly large influence. More specifically, the spike-like noise has a large amplitude, and hence unless the noise is sufficiently attenuated by a filter, the noise is superimposed on the position signals PA1 and PB1 substantially simultaneously as noise having a wide pulse width, so that position detection errors are accumulated. However, even if a filter is inserted, since the noise has the frequency of several kHz, the frequency of the noise is sometimes overlapped with the frequency of the position signals.

In this case, conventionally, the vibration actuator 100 has been required to reduce the maximum speed of the driven element 9 to thereby separate the frequency band of the position signal from the frequency band of the varying magnetic field. However, by using the filter circuit 3Ca shown in FIG. 21 as the first filter 3C of the controller 160, it is possible to cope with the electromagnetic noise that is superimposed on the two-phase position signals PA1 and PB1 substantially simultaneously. Therefore, by setting a frequency band equivalent to the filter applied to spike-like noise, against noise which is substantially simultaneously superimposed on the position signals PA1 and PB1 with a narrow interval between two changing points, it is possible to cut off the noise without adversely affecting the frequency band of the position signals PA1 and PB1.

Next, as an example of noise caused by continuous mechanical vibration, a description will be given of an example in which the vibration of the vibration actuator 100 is transmitted to the rotary encoder 2. As a light source of the optical sensor 12 which is a component of the rotary encoder 2, for example, a semiconductor laser is used, and the rotary encoder 2 has a high resolution by making use of optical interference. In this rotary encoder 2 having a high resolution, when minute vibration is added to the optical scale 11, the position signals PA1 and PB1 are sometimes largely influenced.

If mechanical vibration is added to the optical scale 11 which is fixed to the output shaft 10 during the driving of the vibration actuator 100, phase modulation caused by mechanical vibration having a frequency not lower than several 10 kHz is generated on the position signals PA1 and PB1. When the optical scale 11 is rotated at a high speed according to the rotation of the output shaft 10, although a slight change in the duty or phase difference of the position signals PA1 and PB1 is caused, pulse-like noise is not caused. However, when the optical scale 11 is rotated at a low speed according to the rotation of the output shaft 10, a signal having a frequency of several 10 kHz appears on the position signals PA1 and PB1 as noise irrespective of the phase speed.

When the vibration actuator 100 is stopped, no vibration of the vibration actuator 100 is transmitted to the optical scale 11, and hence, the position signals PA1 and PB1 are not influenced. However, in a case where a plurality of actuators are used in combination, it is necessary to take into account vibration transmitted from the other actuators. Noise caused by such continuous mechanical vibration can be cut off by using not the first filter 3C, but the second filter 25.

As described above, the controller 160 according to the second embodiment includes two filters (first filter 3C and second filter 25) in each of which a frequency band can be set. Then, one of the two filters is applied to an AC signal having a frequency corresponding to the rotational speed of the driven element 9, and is mainly used to cut off electromagnetic noise. Further, the other is applied to a position signal output from the counter 4, and is mainly used to cut off noise caused by mechanical vibration. This makes it possible to efficiently cut off electromagnetic noise and noise caused by mechanical vibration to thereby perform stable control.

Although in the second embodiment, the method of setting a frequency band in each of two filters for filtering various forms of noise has been described, it is desirable to change the frequency bands of the two filters according to the actual usage environment. However, in a case of an application in which an environment including electromagnetic noise and mechanical vibration variously changes, it is sometimes desirable to change the settings according to a situation. For example, it is very useful if the frequency band set for a filter can be automatically set when the vibration actuator is stopped. Since the detected signal contains no position signal component when the vibration actuator is stopped, it is convenient for analyzing the frequency of electromagnetic noise and mechanical vibration.

For example, when the vibration actuator is stopped, the frequency of mechanical vibration is detected by analyzing frequency components of the position signal P2 using a calculation unit, such as FFT, and the frequency band is set for the filter based on a result of the detection. In doing this, one or both of the frequency bands 1 and 2 is/are set such that a predetermined number of frequency components in a decreasing order of amplitude are made smaller in amplitude than a predetermined amplitude, whereby it is possible to adjust the balance of stability and quick responsiveness during stopping as desired according to a usage environment. Further, the frequency bands 1 and 2 may be set by analyzing the frequency characteristics of the position signals PA1 an PB1, and the position signal P1.

Although in the second embodiment, the description has been given of the configuration in which two filters are connected in series, the configuration may be such that more filters are connected. In this case, a configuration in which the plurality of filters are connected in a manner combining serial connection and parallel connection may be employed insofar as frequency bands can be set in the filters and position signals are output from the filters.

Next, a description will be given of a third embodiment of the present invention. In the first and second embodiments, the rotary encoder 2 for detecting a relative position is used as a position sensor for detecting the rotation position of the driven element 9. In contrast, in the third embodiment, a position sensor for detecting an absolute position of the driven element 9 is used.

Figure 23:
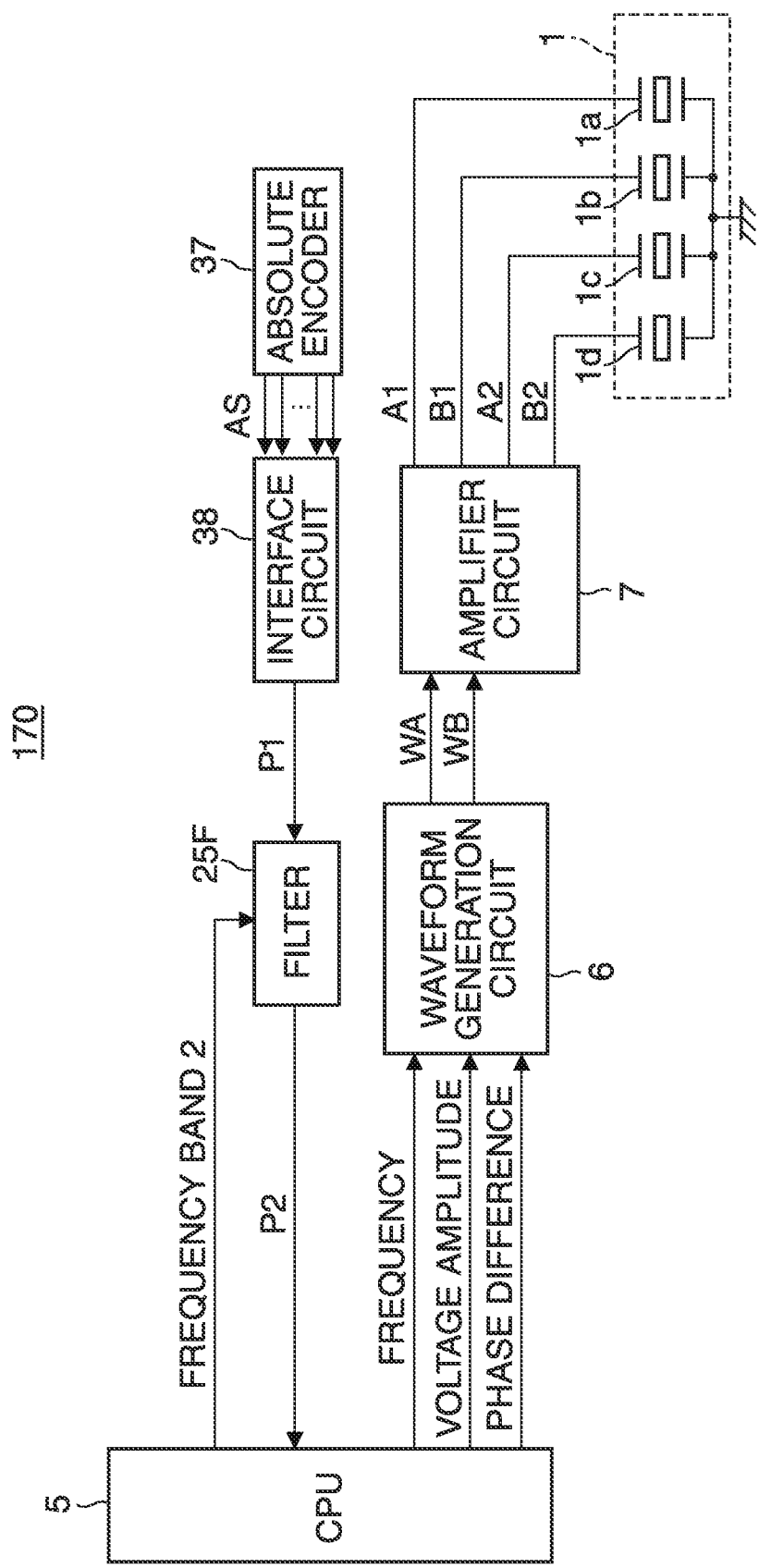
FIG. 23 is a schematic block diagram of a controller according to a third embodiment of the present invention.

FIG. 23 is a schematic block diagram of a controller 170 according to the third embodiment of the present invention. In the present embodiment, it is assumed that a target of driving control of the controller 170 is a vibration actuator having a structure in which the rotary encoder 2 provided in the vibration actuator 100 shown in FIG. 1 is replaced by an absolute encoder 37.

The controller 170 includes the CPU 5, the waveform generation circuit 6, the amplifier circuit 7, a filter 25F, the absolute encoder 37, and an interface circuit 38. The CPU 5, the waveform generation circuit 6, and the amplifier circuit 7 are the same as those included in the controller 150 according to the first embodiment (or the controller 160 according to the second embodiment), and hence description thereof is omitted. Further, the filter 25F is the same as the second filter 25 of the controller 160 according to the second embodiment, and hence description thereof is omitted.

The absolute encoder 37 outputs signals AS formed by multi-channel signals corresponding to an absolute position of the driven element 9. The interface circuit 38 has the signals AS input thereto, and outputs the position signal P1 corresponding to the absolute position.

As the absolute encoder, there are proposed various types based on respective methods. Many of them are configured to output the multi-channel signals AS, and determine an absolute position by using a specific interface circuit to which the signals AS are input, and performing calculation. A time phase relationship between multichannel signals AS is important to determine the absolute position of the driven element 9, and hence calculation for detecting the absolute position of the driven element 9 is often performed by digital calculation having less error.

Although there is a case where the signal AS is an analog signal, when the signal AS is an analog signal, calculation is performed after converting the analog signal to a digital signal using an A/D converter. Further, as a filter used for an analog signal, a filter having a fixed frequency including a cut-off frequency not higher than ½ of the sampling frequency of the A/D converter is additionally used.

Further, examples of the absolute encoder include one that outputs the multi-channel signals AS each having a different frequency band. In this case, if a filter is provided for each of the channels, it is desirable to use a linear phase filter which does not generate a different delay time depending on the frequency. In the filter circuit of the filter 3 shown in FIGS. 6A and 6B, a delay time is not varied insofar as the same settings are applied to each of the signals AS, and hence the filter 3 can be used. Further, it is desirable to once convert the multichannel signals AS to a position signal, and then further suppress the influence of electromagnetic noise or noise caused by mechanical vibration using a known filter.

Incidentally, examples of a sensor for detecting an absolute position include a potentiometer. The potentiometer outputs an analog voltage corresponding to a detected position. Therefore, in a case where the potentiometer is used in place of the absolute encoder, the A/D converter is used as an interface to convert an analog voltage to a digital position signal P1, and the position signal P1 is input to the second filter 25.

When the potentiometer is used, as the frequency band 2 set in the second filter 25, it is preferable to set the frequency band Fr2 so as to eliminate electromagnetic noise during driving as indicated by the pattern 4 in FIG. 18, and use the frequency band Fr4 for coping with noise caused by mechanical vibration during stopping. This makes it possible to obtain quick responsiveness during the driving of the vibration actuator and stability during stopping. Note that in an environment having less electromagnetic noise, as indicated by the pattern 1 in FIG. 18, a signal may be allowed to directly pass without setting the frequency band 2 during driving.

Next, a description will be given of a fourth embodiment of the present invention. In the first to third embodiments, by stopping energization of the piezoelectric element of the vibration actuator, driving of the vibration actuator is stopped. In contrast, in the fourth embodiment, the description is given of a configuration in which the driven element is stopped in a state where the voltage is applied to the piezoelectric element. Note that when the driven element is held in a substantially stopped state, similarly to the case where energization of the piezoelectric element is stopped as in the above-described embodiments, for example, a frequency band narrower than one for during driving is set in the filter 3 as the frequency band 1.

As a first method for stopping the driven element in a state where the voltage is applied to the piezoelectric element, there is a method of reducing a vibration component in a direction of driving the driven element to substantially zero. In many of the vibration actuators, a vibration component in the direction of driving the driven element and a vibration component in a direction orthogonal to the driving direction are simultaneously excited in the vibration element. Here, the vibration element and the driven element are held by a friction force in the vibration actuator, and hence if the driving force is smaller than the friction force, the vibration element and the driven element are prevented from being relatively moved. Therefore, if the magnitude of a force (hereinafter referred to as the "substantial driving force") generated as a result of overcoming the friction force by a total of forces in the driving direction which contribute to driving of the driven element is made equal to zero, it is possible to stop driving of the vibration actuator.

Figure 24A:
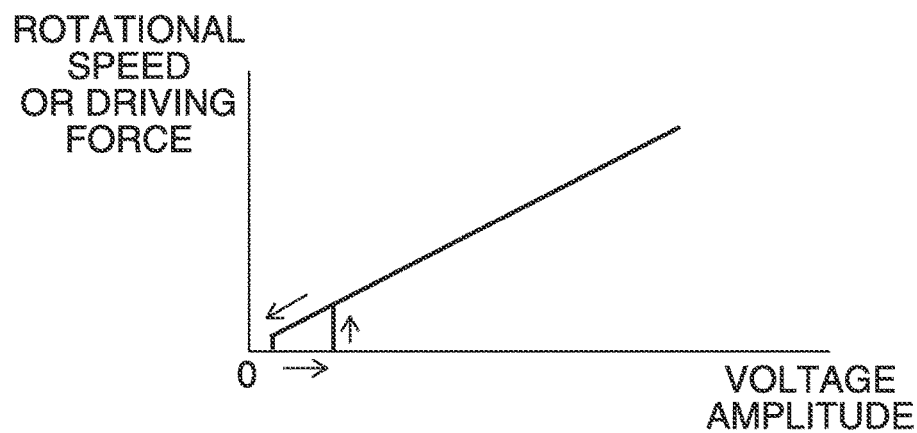
FIGS. 24A to 24C are diagrams showing driving characteristics of the vibration actuator shown in FIG. 1.
Figure 24B:
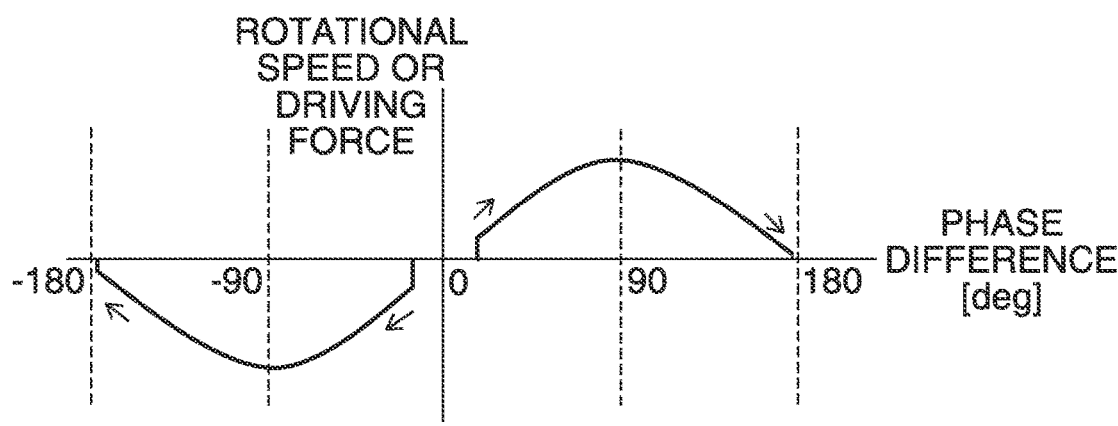
Figure 24C:
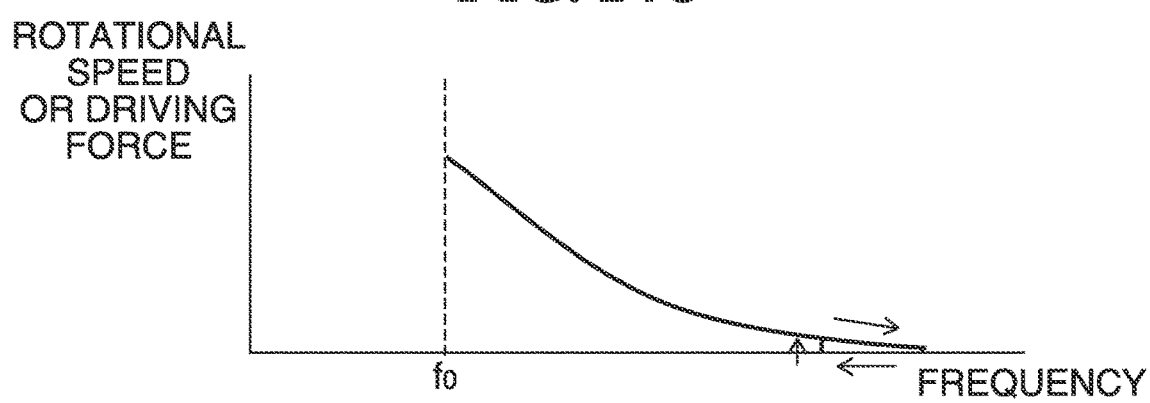

Then, the following description will be given of a method of reducing the substantial driving force to zero by taking the vibration actuator 100 shown in FIG. 1 as an example. FIGS. 24A to 24C are diagrams showing driving characteristics of the vibration actuator 100, in which FIG. 24A shows a relationship between the rotational speed and the substantial driving force of the driven element 9 and the voltage amplitude, FIG. 24B shows a relationship between the rotational speed and the substantial driving force of the driven element 9 and the phase difference, and FIG. 24C shows a relationship between the rotational speed and the substantial driving force of the driven element 9 and the frequency.

The vibration actuator 100 is driven at the four-phase driving voltages A1, B1, A2, and B2 which are shifted by 90 degrees from one another (see FIG. 3). Arrows in FIG. 24A indicate characteristics exhibited when one or both of the voltage amplitude of the driving voltages A1 and A2, and the voltage amplitude of the driving voltages B1 and B2 is/are gradually increased from 0 V and when the same is gradually reduced toward 0 V. A path during driving and a path during stopping are different, and this indicates that the driving voltage characteristics of the vibration actuator 100 have a dead zone and hysteresis.

When the amplitude of the driving voltages A1, B1, A2, and B2 is lower than a predetermined value (different between during stopping and during driving), the rotational speed and the substantial driving force become equal to zero. That is, the substantial driving force can be reduced to zero without making the amplitude of the driving voltage A1, B1, A2, B2 equal to 0 [V]. Note that when one of the amplitude of the driving voltages A1 and A2 and the amplitude of the driving voltages B1 and B2 is made equal to 0 [V], the travelling property of the vibration is lost, and hence this corresponds to reduction of the substantial driving force to zero.

FIG. 24B shows characteristics exhibited in a case where a phase difference between the pulse signals WA and WB (see FIG. 2) is swept from 0 degrees to +180 degrees and in a case where the phase difference is swept from 0 degrees to −180 degrees, respectively. In both the cases, when the phase difference enters a predetermined range having 0 degrees or ±180 degrees as the center, the rotational speed and the substantial driving force become equal to zero. As shown in FIG. 24B, the characteristics during stopping and the characteristics during driving are different, which indicates that the phase difference characteristics also have a dead zone and hysteresis. Therefore, even while applying the driving voltages A1, B1, A2, and B2 to the piezoelectric element 1, it is possible to reduce the substantial driving force to zero by setting the phase difference between the pulse signals WA and WB to 0 degrees or 180 degrees.

FIG. 24C shows the characteristics exhibited when the driving frequency is swept from a frequency higher than a resonance frequency $f_0$ to the resonance frequency $f_0$ and when the frequency is swept from the resonance frequency $f_0$ to the frequency higher than the resonance frequency $f_0$. The frequency sweeping characteristics also have a dead zone and hysteresis, and the rotational speed and the substantial driving force become equal to zero at a frequency not lower than a predetermined frequency.

Not only an actuator having an annular vibration element and a driven element, such as the vibration actuator 100 but also many of vibration actuators which are driven by a plurality of AC voltages and also make use of a resonance phenomenon of the vibration element have at least one of the characteristics shown in FIGS. 24A to 24C.

Figure 25A:
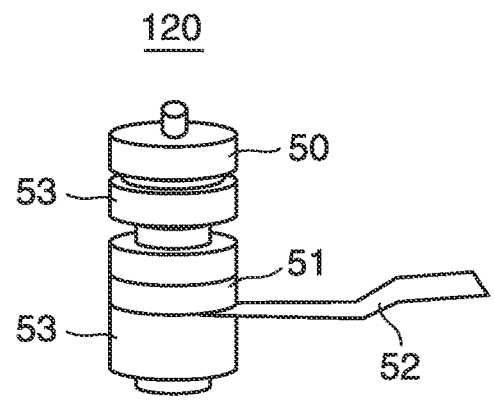
FIG. 25A is a schematic perspective view of another vibration actuator as a target of driving control of a controller according to a fourth embodiment of the present invention.
Figure 25B:
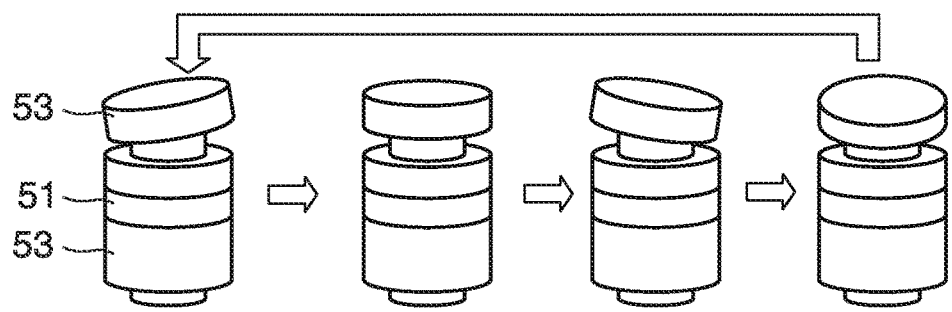
FIG. 25B is a schematic view showing vibration that is generated in an elastic body of the other vibration actuator.
Figure 25C:
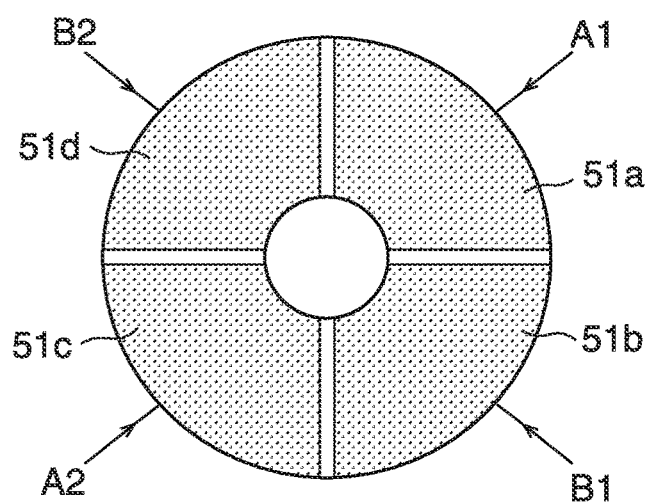
FIG. 25C is a plan view of electrodes of a piezoelectric element as a component of the other vibration actuator.

The first method for stopping the driven element in the state where voltage is applied to the piezoelectric element will be described, by taking another vibration actuator as an example, which is different from the vibration actuator 100, with reference to FIGS. 25A to 25C. FIG. 25A is a schematic perspective view of another vibration actuator 120 as a target of driving control of a controller according to the fourth embodiment. FIG. 25B is a schematic view showing vibration that is generated in an elastic body 53 of the vibration actuator 120. FIG. 25C is a plan view of electrodes of a piezoelectric element 51 as components of the vibration actuator 120.

The vibration actuator 120 includes the piezoelectric element 51, the elastic body 53, and a driven element 50. The piezoelectric element 51 is held in a sandwiched manner by the elastic body 53 composed of two members, and the piezoelectric element 51 and the elastic body 53 form a vibration element. Electric power is supplied to the piezoelectric element 51 via a flexible circuit board 52 held in a sandwiched manner between the piezoelectric element 51 and one member of the elastic body 53. The driven element 50 is frictionally driven for rotation by elliptical vibration formed on an upper surface (surface which is brought into contact with the driven element 50) of the elastic body 53. Note that means for pressing the driven element 50 against the elastic body 53 with a predetermined pressure force and means for rotatably supporting the driven element 50 are not shown.

When an AC voltage is applied to the piezoelectric element 51 via the flexible circuit board 52, two bending vibrations which are orthogonal to each other in a thrust direction of the elastic body 53 are formed. By giving a phase shift of 90 degrees between these two bending vibrations, the elastic body 53 is vibrated in such a manner that an upper portion (portion which is brought into pressure contact with the driven element 50) of the elastic body 53 above a narrow portion whirls. As a result, elliptical vibration is formed at a mass point on the upper surface of the elastic body 53, whereby the driven element 50 which is brought into pressure contact with the upper surface of the elastic body 53 is frictionally driven for rotation.

One of the surfaces of the annular piezoelectric element 51 is provided with the electrodes, denoted by reference numerals 51a, 51b, 51c, and 51d, as four partitioned sections, and driving voltages A1, B1, A2, and B2 are applied to the electrodes 51a, 51b, 51c, and 51d, respectively. The other surface opposite to the surface provided with the electrodes 51a, 51b, 51c, and 51d across the piezoelectric body is formed with one full-surface electrode (common electrode). Further, the piezoelectric element 51 may be driven by any one of the controller 150 shown in FIG. 2, the controller 160 shown in FIG. 15, and the controller 170 shown in FIG. 23.

In the vibration actuator 120, when the driving voltages A1 and A2 or the driving voltages B1 and B2 are set to 0 [V], only bending vibration in one direction is generated, and hence a driving force in the rotational direction is not generated. Similarly, when the phases of the driving voltages A1 and B1 are made coincident with each other, and the phases of the driving voltages A2 and B2 are made coincident with each other, only bending vibration in one direction is generated, and hence a driving force in the rotational direction is not generated.

As a second method of reducing the driving force of the vibration actuator to zero, there is a method of generating a vibration component of a driving force in an opposite direction to the driving direction (vibration shifted in phase by 180 degrees) to thereby cause the driving forces to be offset by each other. In this method, the driving force may be offset between a plurality of contact points of one vibration element, or may be offset between a plurality of vibration actuators.

In the case of the above-described method of stopping the driven element by reducing the substantial driving force to zero without stopping energization of the piezoelectric element as a component of the vibration actuator, since vibration excited in the vibration element is not reduced to zero, power consumption is increased, but an effect of advancing the start time can be expected. Therefore, it is possible to improve the controllability when correcting a minute position shift during stopping. Accordingly, next, a controller for performing a driving method of stopping the driven element by reducing the substantial driving force to zero will be described with reference to FIGS. 26 and 27.

Figure 26:
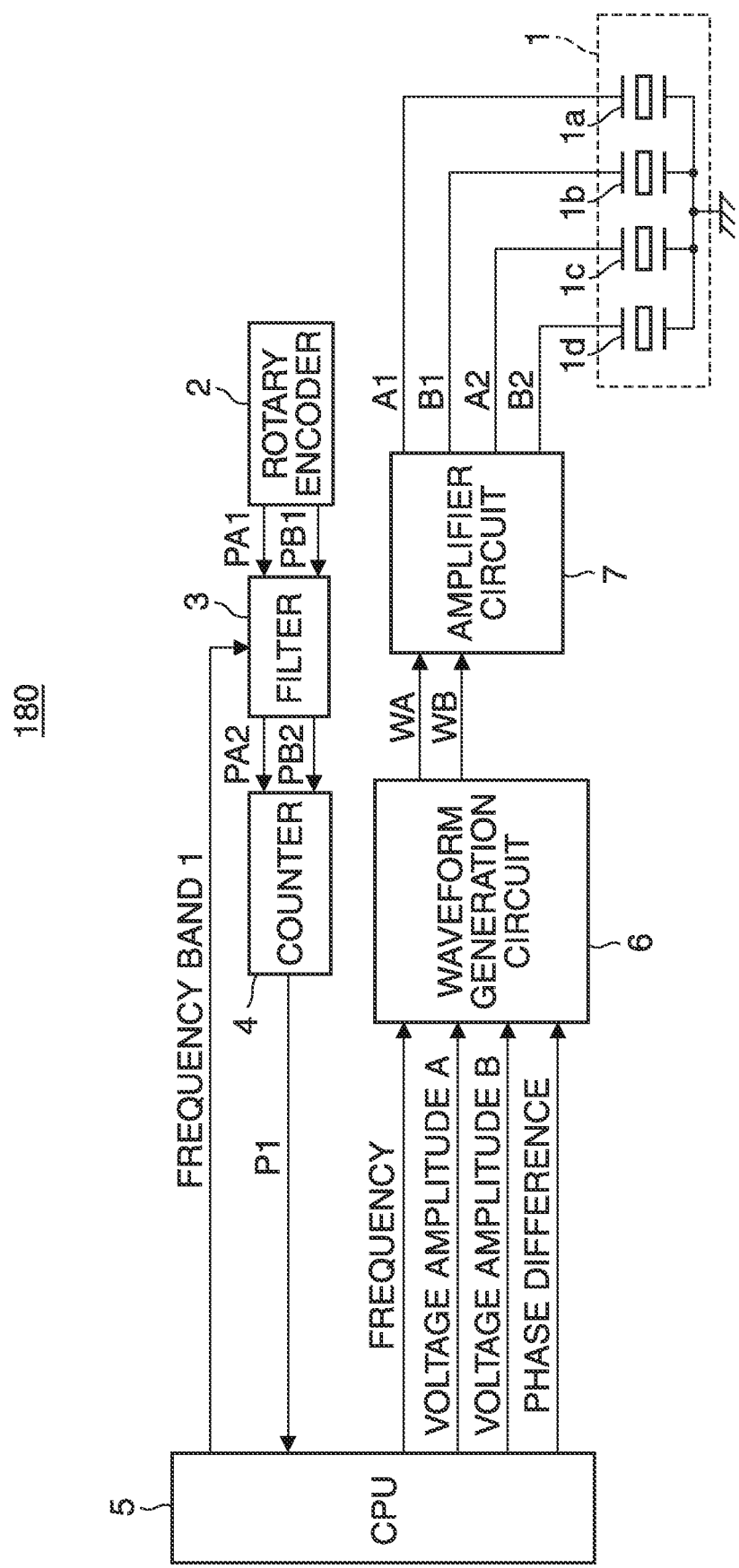
FIG. 26 is a schematic block diagram of the controller according to the fourth embodiment of the present invention.

FIG. 26 is a schematic block diagram of a controller 180 as an example of the controller according to the fourth embodiment. FIG. 26 shows the piezoelectric element 1 of the vibration actuator 100 shown in FIG. 1 as a piezoelectric element as a target of control of the controller 180, but this is not limitative. For example, the target of control of the controller 180 may be the piezoelectric element 51 of the vibration actuator 120 shown in FIG. 16, and further, the actuator is only required to be an actuator driven by the four-phase driving voltages A1, B1, A2, and B2.

The controller 180 differs from the controller 150 shown in FIG. 2 in that the CPU 5 can set amplitudes of the pulse signals WA and WB output from the waveform generation circuit 6, for the waveform generation circuit 6, using independent signals of voltage amplitudes A and B, respectively, but does not differ in the other configuration. Therefore, description redundant to that of the controller 150 is omitted.

In the controller 180, the voltage amplitude of the driving voltages A1 and A2, and the voltage amplitude of the driving voltages B1 and B2 can be independently set, and hence by setting only the amplitude of the driving voltages A1 and A2 or the driving voltages B1 and B2 to be not higher than a predetermined voltage, it is possible to reduce the substantial driving force to zero. Further, in the controller 180, it is also possible to easily set a phase difference between the signals WA and WB in the vicinity of 0 degrees or 180 degrees by setting the phase difference, and separate the frequency of the driving voltage from the resonance frequency of the elastic body 8 using a frequency signal.

Although a timing diagram used in the controller 180 is not shown, the control is performed substantially according to the timing diagram shown in FIG. 8. In stopping the driving of the vibration actuator 100, when the position signal P2 is in a predetermined positional relationship with respect to the stop area command, the CPU 5 decides to stop driving the vibration actuator 100. Then, after changing the drive command to the low level, the CPU 5 reduces the substantial driving force to zero using one of the above-described methods. After the lapse of a predetermined time period (T1 in FIG. 8), the CPU 5 changes the frequency band 1 set in the filter 3 from the frequency band F11 to the frequency band F10.

When starting the vibration actuator 100, the starting process is performed substantially according to a procedure opposite to the above-described procedure for stopping the vibration actuator 100. That is, first, the CPU 5 returns the frequency band 1 from the frequency band F10 to the frequency band F11, sets the drive command to the high level after the lapse of a predetermined time period (T2 in FIG. 8), and sets the driving parameters satisfying the driving conditions in the waveform generation circuit 6.

Figure 27:
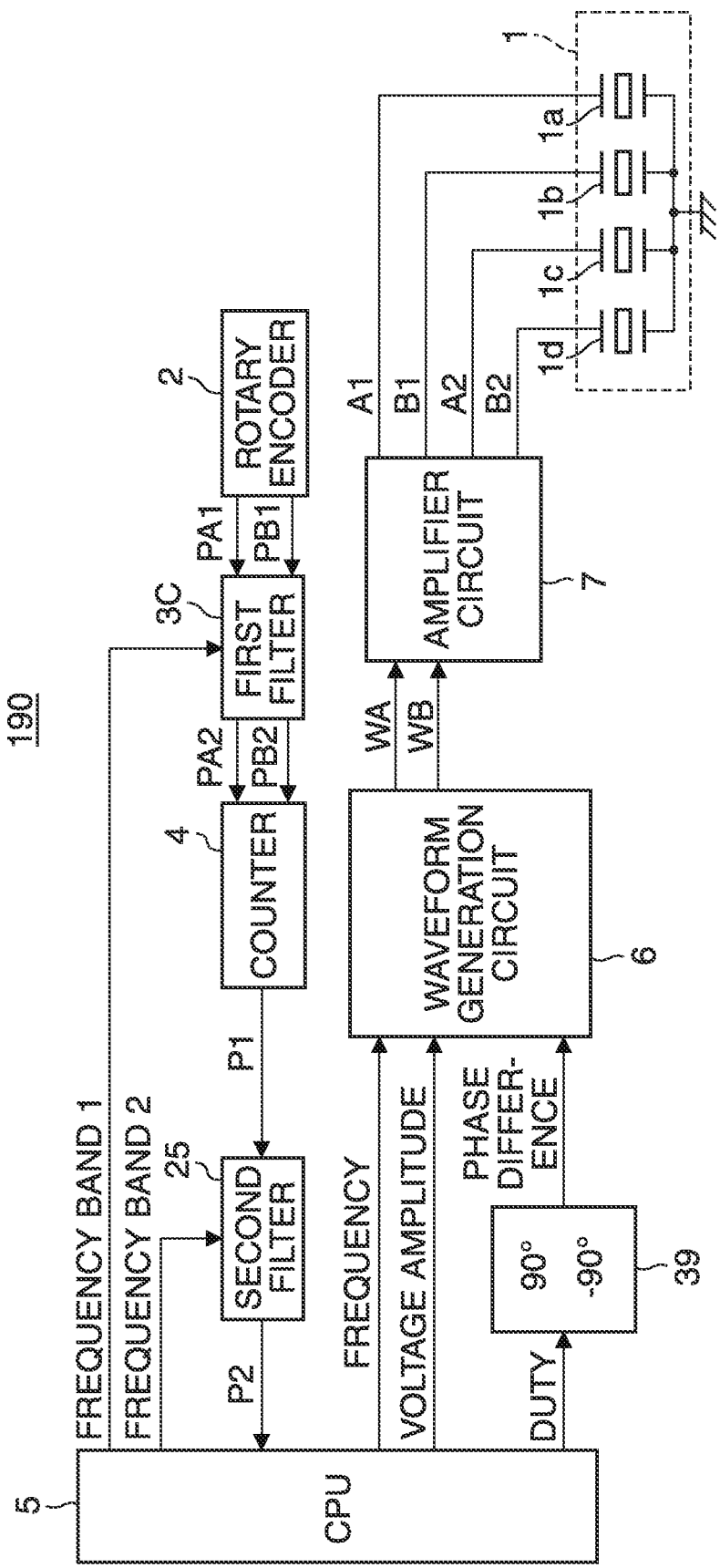
FIG. 27 is a schematic block diagram of a variation of the other controller according to the fourth embodiment of the present invention.

FIG. 27 is a schematic block diagram of a controller 190 as a variation of the controller 180 according to the fourth embodiment. Although FIG. 27 also shows the piezoelectric element 1 of the vibration actuator 100 shown in FIG. 1 as a piezoelectric element as a target of control of the controller 190, this is not limitative. For example, the target of control of the controller 190 may be the piezoelectric element 51 of the vibration actuator 120 shown in FIG. 16, and further, the actuator is only required to be an actuator driven by the four-phase driving voltages A1, B1, A2, and B2.

The controller 190 differs from the controller 160 according to the second embodiment, shown in FIG. 15, in that a phase difference adjustment circuit 39 is provided between the CPU 5 and the waveform generation circuit 6 to further reduce the influence of the dead zone of the vibration actuator 100, but does not differ in the other respects. Therefore, description redundant to that of the controller 160 is omitted.

In the controller 190, by providing the phase difference adjustment circuit 39 for inverting the direction of driving the vibration actuator 100 at a predetermined period, a ratio of use of the driving direction and use of the opposite direction to the driving direction is adjusted using a duty signal delivered from the CPU 5. By setting predetermined period at which the driving direction is reversed to a period corresponding to a frequency not lower than e.g. several hundreds [Hz], and setting the duty to 50%, it is possible to maintain the driven element 9 in a substantially stopped state by inertia effect of the driven element 9 while being accompanied by small vibrations caused by inverting the direction.

In this case, the frequency band 2 set in the second filter 25 during the stopping of the driven element 9 is set so as to cut off noise caused by mechanical vibration generated at the predetermined period at which the driving direction is reversed. This is because, as described in the second embodiment, if noise caused by continuous mechanical vibration is cut off by the first filter 3C, the position signals PA1 and PB1 are also cut off, which prevents the position of the driven element 9 form being detected. For this reason, the frequency band 1 is set in the first filter 3C so as to cut off only high-frequency noise corresponding to electromagnetic noise.

On the other hand, when the driven element 9 is driven, the CPU 5 sets the duty to 0% or 100% to thereby drive the vibration actuator 100 only in one direction. Therefore, mechanical vibration generated during the stopping of the driven element 9 is not generated, and hence it is possible to make the frequency band 2 set in the second filter 25 wider than that set during stopping, which makes it possible to increase both of stability during stopping and quick responsiveness during driving.

Note that the method of periodically switching the driving direction can also be applied to a vibration actuator which is driven by a single-phase driving voltage, insofar as it is a vibration actuator based on a method of switching the driving direction by switching between two driving phases.

Figure 28A:
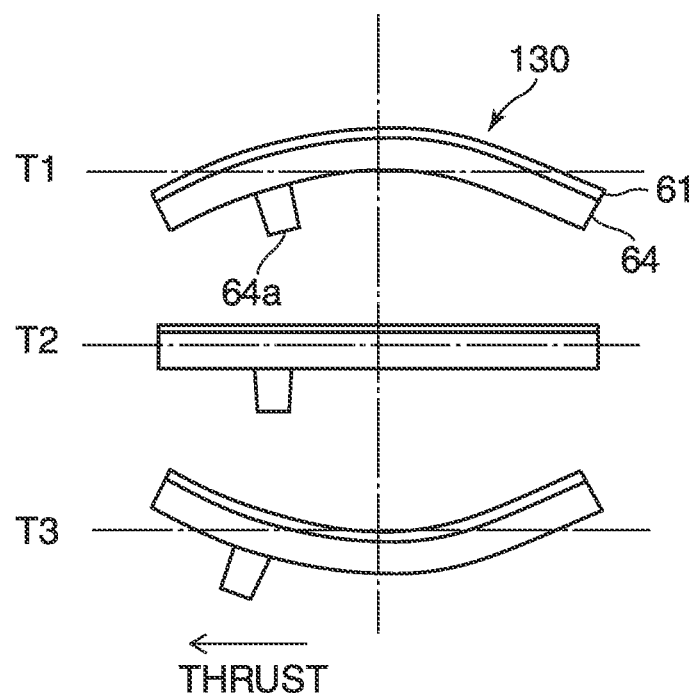
FIG. 28A is a diagram showing a single-phase vibration actuator which can be driven in one direction only, and a vibration form.

FIG. 28A is a diagram useful in explaining the configuration of a single-phase vibration element 130 which can be driven in one direction only, and a manner of vibration. The vibration element 130 has a structure that a piezoelectric element 61 is bonded to an elastic body 64 having a protruding portion 64a. FIG. 28A shows how the elastic body 64 is deformed in accordance with the lapse of time, in the order of time points T1, T2, and T3. The elastic body 64 is vibrated in an out-of-plane primary bending mode, and the protruding portion 64a provided at a location shifted from a position of the antinode of the bending vibration applies a thrust to a driven element, not shown, in a direction indicated by an arrow, whereby the driven element and the vibration element 130 are relatively moved.

Figure 28B:
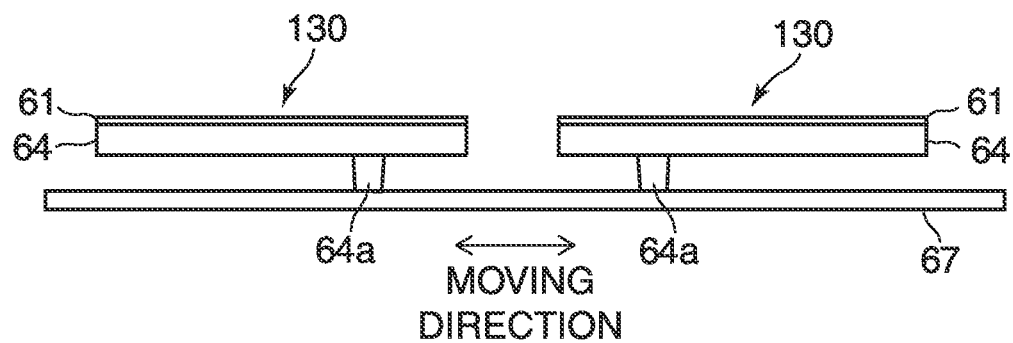
FIG. 28B is a schematic view of a combined actuator formed by combining two vibration actuators.

FIG. 28B is a schematic view of a combined actuator formed by combining the two vibration elements 130. The two vibration elements 130 are disposed such that they generate thrusts in directions opposite to each other for a driven element 67, and are each movable relative to the driven element 67 in a direction of generating an associated one of the thrusts. Further, the protruding portions 64a of the two vibration elements 130 and the driven element 67 are brought into pressure contact with each other by pressure means, not shown.

Figure 29:
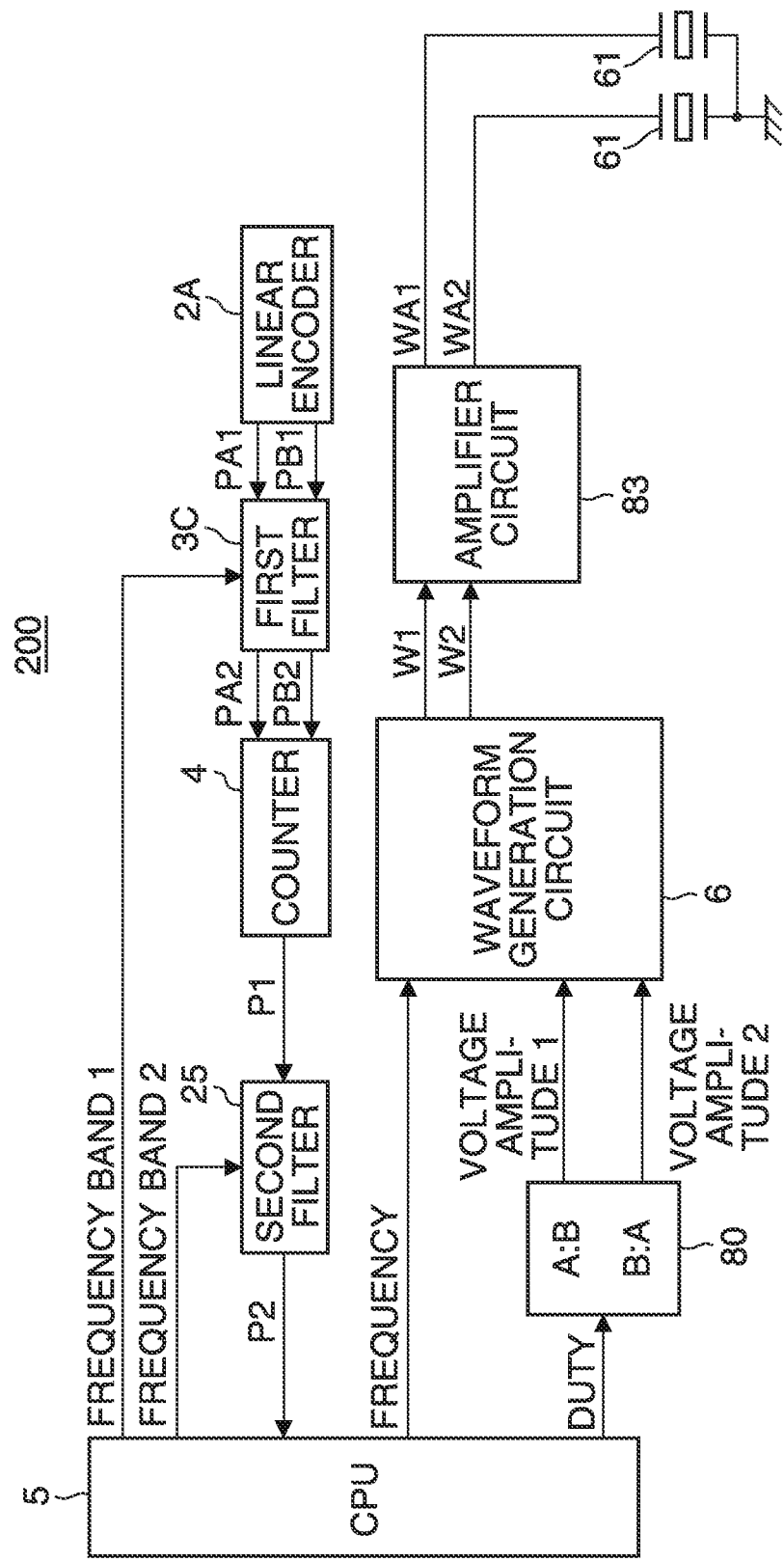
FIG. 29 is a schematic block diagram of a controller according to a fifth embodiment of the present invention, which controls the driving of the combined actuator shown in FIG. 28B.

FIG. 29 is a schematic block diagram of a controller 200 according to a fifth embodiment of the present invention, which performs driving control of the combined actuator shown in FIG. 28B. The controller 200 differs from the controller 160 according to the second embodiment, shown in FIG. 15, in that a linear encoder 2A is provided to detect the driven element 67, and in the process for generating driving voltages WA1 and WA2 applied to the vibration elements 130. A known linear encoder can be used as the linear encoder 2A, and the position detection method used by the linear encoder 2A is the same as that used e.g. by the rotary encoder 2 appearing in FIG. 1. Therefore, description redundant to that of the controller 160 is omitted.

The controller 200 includes a switching circuit 80 for switching the driving voltages applied to the two vibration elements 130 between predetermined two modes of a voltage ratio A:B (voltage amplitude 1) and a voltage ratio B:A (voltage amplitude 2). The switching circuit 80 supplies the voltage amplitude 1 and the voltage amplitude 2 to the waveform generation circuit 6 in a manner alternately temporally switching the mode at a predetermined voltage ratio based on a duty supplied from the CPU 5. Pulse signals W1 and W2 output from the waveform generation circuit 6 are amplified by an amplifier circuit 83 to thereby generate driving voltages WA1 and WA2. The driving voltages WA1 and WA2 are applied to the piezoelectric elements 61 of the two vibration elements 130, respectively. When the driven element 67 is stopped, the two vibration elements 130 alternately apply a thrust in the opposite directions to the driven element 67, and by switching the forces in the opposite directions at a duty of approximately 50% at a predetermined period, it is possible to make the average driving force (substantial driving force) equal to zero. To drive the driven element 67 in one direction, it is only required to set the duty to 0% or 100%. Although the configuration in which the two vibration elements 130 are provided has been described, three or more vibration elements 130 may be provided, and also in this case, to stop the driven element 67, it is only required to perform control such that a sum of thrusts applied to the driven element 67 by the plurality of vibration elements 130 becomes equal to zero.

As described above, in the fourth embodiment, by making the substantial driving force of the vibration actuator equal to zero using the various methods, the driven element is stopped. As a consequence, in an application provided with the vibration actuator, by setting the frequency band of a position signal indicative of a position of the driven element such that it is narrower during stopping than during driving, it is possible to increase quick responsiveness during driving while maintaining stability during stopping. The driving control method for the vibration actuator described as to the present embodiment is not limited to the drive control for the vibration actuator 100, described by way example, but is effective to the actuator driving control that makes it possible to make the substantial driving force equal to zero during stopping.

Figure 30:
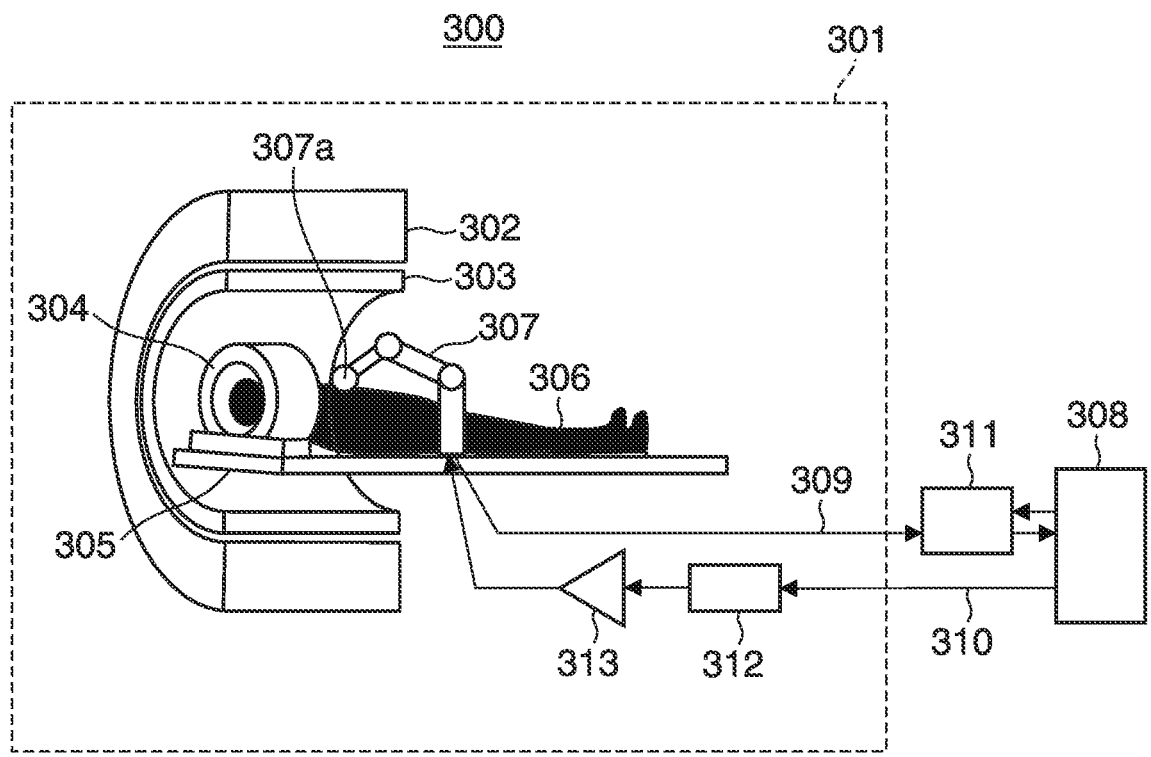
FIG. 30 is a schematic view of an MRI diagnostic apparatus to which the controller according to the embodiments of the present invention is applied.

Next, a description will be given of an example in which one of the controllers according to the above-described first to fifth embodiments is applied to an MRI diagnostic apparatus which is an example of a medical system. FIG. 30 is a schematic view of an MRI diagnostic apparatus 300. In the MRI diagnostic apparatus 300, it is possible to perform fMRI (functional Magnetic Resonance Imaging) measurement for visualizing changes in blood flow caused by activity of a brain or a vertebrae, and by moving a robot arm as a driven mechanism using the vibration actuator, a contact stimulus applied to a subject is varied on a time-series basis, and changes in blood flow according to the changed contact stimulus are measured. In doing this, for movement of the robot arm within an MRI bore, reduction of electromagnetic noise caused by a driving source using a magnetic shield, non-magnetization of each member, and so forth are performed.

As the stimulus applied to a subject, not only one associated with the sense of touch, but also one associated with the sense of sight, the sense of hearing, or the like is considered. The robot arm can also be used to apply a predetermined stimulus associated the sense of sight, the sense of hearing, or the like.

The MRI diagnostic apparatus 300 includes a measurement unit provided within a magnetic shield chamber 301 and a controller 308 provided outside the magnetic shield chamber 301. The MRI diagnostic apparatus 300 is particularly sensitive to electromagnetic noise caused in the vicinity of a frequency referred to as the Larmor frequency which is determined according to magnetic field intensity specific to the apparatus. The Larmor frequency is a frequency of procession of magnetic dipole moment of the atomic nucleus within a brain of a subject 306.

The Larmor frequency is within a range of 8.5 MHz to 128 MHz at the magnetic field intensity within a range of 0.2 T to 3 T of the MRI diagnostic apparatus 300 which is generally used for real clinical use, and a device operating in the magnetic shield chamber 301 is required to minimize occurrence of electromagnetic noise in this frequency band. However, in general, the controller 308 including a signal calculation unit, such as a CPU or a FPGA, operates according to an external clock at approximately 10 MHz to 50 MHz, and hence the frequency of electromagnetic noise caused by clock signals is widely overlapped with a region of the Larmor frequency if harmonics of the electromagnetic noise are included. For this reason, the measurement unit that measures a minute change in the magnetic field, occurring in the brain, is installed within the magnetic shield chamber 301 in which the influence of external noise is cut off.

The measurement unit of the MRI diagnostic apparatus 300 includes a superconductive magnet 302, a gradient magnetic field generating coil 303, an RF coil 304, a bed 305, and a robot arm 307. The superconductive magnet 302 generates a static magnetic field. The gradient magnetic field generating coil 303 generates a gradient magnetic field to identify a three-dimensional position. The RF coil 304 irradiates the subject 306 lying on the bed 305 with electromagnetic waves, and receives the reflected electromagnetic waves. The superconductive magnet 302 and the gradient magnetic field generating coil 303 each have a hollow cylindrical shape, but are shown in a state cut into half in FIG. 30. The RF coil 304 is made specific to MRI measurement in a brain, and is formed into a hollow cylindrical shape to cover a head part of the subject 306 lying on the bed 305.

The measurement unit of the MRI diagnostic apparatus 300 performs various sequences of generation of a gradient magnetic field and irradiation of electromagnetic waves, according to a control signal delivered from an external controller, not shown, provided outside the magnetic shield chamber 301. Then, the external controller acquires various information in the brain using received signals obtained from the RF coil 304. Note that the external controller may be included in the controller 308.

The robot arm 307 is fixed on the bed 305. The robot arm 307 has a structure capable of performing the three-degree-freedom motions of rotations of two joint parts which are movable parts and turning of a base part, and is capable of applying a stimulus to the subject 306 on a time-series basis by bringing a contact ball 307a disposed at an extremity of the arm into contact with a desired position of the subject 306 with a desired contact force. Each joint part and the turning base part of the robot arm 307 are each provided with the vibration actuator 100 shown in FIG. 1 or the vibration actuator 120 shown in FIGS. 25A to 25C, a rotation sensor, a force sensor, neither of which is shown, etc. Detection signals output from the rotation sensor and the force sensor are converted to optical signals, and the optical signals are transmitted to an optical signal reception section 311 having the filter function, provided outside the magnetic shield chamber 301, through an optical fiber 309.

The cut-off frequency of the filter of the optical signal reception section 311 is set by the controller 308, and is changed according to the operating condition of the vibration actuators provided in the robot arm 307. The controller 308 and the filter of the optical signal reception section 311 correspond to the CPU 5 and the filter 3, described in the first embodiment, respectively.

Here, the cut-off frequency setting will be described. The robot arm 307 applies a force to the subject 306 on a timely basis during MRI imaging (during photographing of an image of MRI). The contact ball 307a is in contact with the subject 306 while measuring changes in blood flow in the brain, and hence the robot arm 307 is not largely moved. Therefore, the controller 308 sets the cut-off frequency of the optical signal reception section 311 to allow passage of a frequency range higher than 0 Hz and not higher than a desired frequency (band corresponding to the motion of the subject 306) to thereby reduce electromagnetic noise caused by MRI imaging. In doing this, since the robot arm 307 is hardly moved, even when the cut-off frequency of the optical signal reception section 311 is set to a low frequency, the rotation position is not erroneously detected because the frequency band of the output signal from the rotation sensor is very low. On the other hand, when largely moving the robot arm 307 after stopping MRI imaging, the controller 308 sets the cut-off frequency of the optical signal reception section 311 to a sufficiently high frequency. By setting the cut-off frequency of the optical signal reception section 311 so as to allow passage of a frequency sufficiently higher than the frequency band of the output signals from the rotation sensor according to the moving speed of the robot arm 307, it is possible to prevent erroneous detection of the rotation position.

The vibration actuators provided at the respective joints of the robot arm 307 are configured to directly drive the respective joints. For this reason, the whole robot arm 307 has high rigidity, and the movement of the robot arm 307 is capable of applying various stimuli in a wide frequency band. The main structure of the robot arm 307 is made of non-magnetic material including the vibration actuator, and is designed to cause as little disturbance as possible in a static magnetic field generated by the superconductive magnet 302.

When photographing an image of MRI, the subject 306 holds the front end of the robot arm 307 by hand, and does not move his/her arms as much as possible. Then, the robot arm 307 is driven to measure changes in blood flow in the brain of the subject 306 in a manner changing the pattern of the magnitude, direction of the force, and the like, on a time-series basis. At this time, it is necessary to cause the robot arm 307 to continuously generate the force, and the robot arm 307 is continuously driven, but the position (posture) of the robot arm 307 is in a substantially stopped state. Therefore, a relatively low frequency can be set in the optical signal reception section 311 as the cut-off frequency. For example, a lower limit of the electromagnetic noise band during MRI imaging is in a range of approximately several hundreds Hz to 1 kHz, and hence the cut-off frequency is set to 100 Hz, whereby a frequency not lower than 100 Hz is cut off.

The controller 308 outputs a drive signal (drive waveform) for driving the vibration actuators within the robot arm 307 according to a result of comparison between a time-series signal for applying a stimulus to the subject 306 along a preset track and with a preset pressure force, and information obtained from the rotation sensor and the force sensor. The drive signal is a pulse signal generated by PWM (Pulse Width Modulation) of a sine wave, and this pulse width-modulated pulse signal is converted to an optical signal within the controller 308, and is transmitted to the inside of the magnetic shield chamber 301 through an optical fiber 310.

An optical signal reception section 312 having the filter function is provided in the magnetic shield chamber 301. The optical signal reception section 312 converts an optical signal output from the controller 308 to an electric signal, cuts off a higher harmonic component of the pulse width-modulated pulse signal at a predetermined cut-off frequency, and outputs a smooth sine wave signal to a linear amplifier 313. The linear amplifier 313 linearly amplifies the sine wave signal output from the optical signal reception section 312, and applies the amplified signal to the vibration actuators. Thus, the vibration actuators are driven to thereby drive the robot arm 307.

Although in the illustrated example, the articulated rotation mechanism, such as the robot arm, has been described, a linear drive-type vibration actuator may be used. Further, although the example in which the present system is applied to medical inspection has been described, it is obvious that the present system may be provided to assist some treatment.

Although the example in which the present invention is applied to the MRI diagnostic apparatus 300 has been described, the present invention is not limited to this, but for example, the present invention can be applied to e.g. an adjustment mechanism for a shock absorber that is driven near a generator having large electromagnetic noise or an electric motor of an electric car. In this case, the cut-off frequency of a low-pass filter applied to a sensor signal is switched between when stopping and driving the generator or the electric motor, which is an electromagnetic noise source. For example, the cut-off frequency is set to a frequency higher than 0 Hz and lower than the lower limit of the frequency band of the electromagnetic noise during operation of e.g. the electric motor, and is set to a sufficiently high frequency (high-frequency side) during stopping.

Out of various types of noise superimposed on a sensor signal of the vibration actuator, one causing a problem is spike-like noise, and the main component of spike-like noise has a relatively high frequency. On the other hand, the frequency of the electric motor of an electric car or the generator at the time of starting thereof is very low, and hence the cut-off frequency to be applied from the start of the apparatus until the high rotational speed thereof is reached may be set based on a result of confirming the influence of noise in advance.

The present invention can also be applied to a device using a plurality of actuators, in which a vibration actuator is used as part of the actuators, such as a copy machine. Particularly, the present invention is effective in a case where the device includes an electromagnetic clutch or an electric motor, which causes large electromagnetic noise in the vicinity of a position sensor of the vibration actuator during the stopping of a unit driven by the vibration actuator. In this case, a low-pass filter having a low cut-off frequency is applied to a signal output from a position sensor during the stopping of the vibration actuator, and application of the low-pass filter is canceled during the driving of the vibration actuator, whereby it is possible to realize high-accuracy position control.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

For example, the vibration actuator 100 described in the first embodiment is configured such that the piezoelectric element 1 in the form of a single annular plate, which is bonded to the annular elastic body 8, functions as an excitation source of the elastic body 8, and the vibration element and the driven element 9 are relatively moved by vibration excited in the elastic body 8. This is not limitative, but examples of the vibration actuator include one that directly drives the driven element with vibration of the piezoelectric element, and one that drives the driven element using shocking excitation. Further, vibration used for frictional driving has various forms, and although the vibration actuator 100 uses bending vibration of the elastic body 8, this is not limitative, but there are vibration actuators using various vibrations, such as vibration in an extension/contraction direction, a surface wave traveling on a surface of the elastic body, and shear vibration in a thickness direction. However, the vibration actuators using any of these systems are common in that a force is transmitted between the vibration element and the driven element via a friction force, and a merit that a holding force acts when vibration is stopped can be obtained, but on the other hand, a relatively large dead zone exists. Therefore, the controller according to the embodiments of the present invention can be applied to the drive control for various vibration actuators regardless of the mechanical configuration of the vibration actuator and the type of vibration used for frictional driving.

This application claims the benefit of Japanese Patent Application No. 2015-095595 filed May 8, 2015, which is hereby incorporated by reference herein in its entirety.

What is claimed is:

1. A controller that controls driving of an actuator, wherein a contact element and the actuator are relatively moved by a driving force of the actuator, and a relative positional relationship between the actuator and the contact element is held in a state in which driving the actuator is stopped, the controller comprising:
 a position detection unit configured to output a first position signal which is an AC signal having a frequency corresponding to a relative moving speed between the actuator and the contact element;
 a filter configured to output a second position signal which is a signal indicative of an amount of relative movement between the actuator and the contact element generated based on the first position signal, the second position signal being generated by said filter attenuating signal components having frequencies except a specific frequency band;
 a control unit configured to control driving and stopping of the actuator according to the second position signal; and
 a setting unit configured to set in said filter, as the specific frequency band, a first frequency band in a case in which said control unit drives the actuator, and a second frequency band in a case in which said control unit stops the actuator,
 wherein the first frequency band and the second frequency band both include 0 Hz, and the second frequency band is narrower than the first frequency band, and
 wherein said filter includes:

a changing unit configured to change a frequency band of the first position signal based on the specific frequency band set by said setting unit, and
a conversion unit configured to convert the first position signal of which the frequency band is changed by said changing unit to the second position signal.

2. The controller according to claim 1, wherein in the case in which said control unit drives the actuator, said control unit generates a driving voltage for moving the actuator and the contact element relative to each other, and in the case in which said control unit stops the actuator, said control unit stops energization of the actuator or generates a driving voltage for generating a driving force smaller than a force for holding the relative positional relationship between the contact element and the actuator.

3. The controller according to claim 1, wherein the first position signal is a digital signal having a binary state, and
wherein said changing unit outputs the first position signal to said conversion unit in a case in which the first position signal holds the same value for a predetermined or longer time period.

4. The controller according to claim 1, wherein the first position signal is a digital signal having a binary state, and
wherein when a time interval between two changes sequentially occurring in the first position signal is shorter than a predetermined time period, said filter ignores the two changes, and when the time interval is longer than the predetermined time period, said filter outputs the first position signal.

5. The controller according to claim 1,
wherein said filter further includes:
a second changing unit configured to change a frequency band of the second position signal converted by said conversion unit, and
wherein said setting unit sets different frequency bands in said changing unit and said second changing unit, respectively, as the specific frequency band set in said filter.

6. The controller according to claim 5, wherein said setting unit sets the frequency band set in said second changing unit to a band that is narrower than the frequency band set in said changing unit, and includes 0 Hz.

7. The controller according to claim 5, wherein the first position signal is a digital signal having a binary state, and
wherein said changing unit outputs the first position signal to said conversion unit in a case in which the first position signal holds the same value for a predetermined or longer time period.

8. The controller according to claim 5, wherein the first position signal is a digital signal having a binary state, and
wherein when a time interval between two changes sequentially occurring in the first position signal is shorter than a predetermined time period, said changing unit ignores the two changes, and when the time interval is longer than the predetermined time period, said changing unit outputs the first position signal.

9. A vibration type actuator apparatus comprising:
a vibration actuator; and
a controller configured to control driving of said vibration actuator,
said vibration actuator comprising:
a vibration element including an electromechanical energy conversion element, and an elastic body that is bonded to said electromechanical energy conversion element; and
a contact element in pressure contact with said vibration element,
wherein said vibration element and said contact element are moved relative to each other by vibration excited in said elastic body by applying a driving voltage to said electromechanical energy conversion element by said controller,
said controller comprising:
a position detection unit configured to output a first position signal corresponding to an amount of relative movement between said vibration element and said contact element;
a filter configured to have the first position signal input thereto, and output a second position signal generated by attenuating signal components having frequencies except a specific frequency band;
a control unit configured to control driving and stopping of said vibration element according to the second position signal; and
a setting unit configured to set in said filter, as the specific frequency band, a first frequency band in a case in which said vibration element and said contact element are moved relative to each other, and a second frequency band in a case in which a relative positional relationship between said vibration element and said contact element is held,
wherein the first frequency band and the second frequency band both include 0 Hz, and the second frequency band is narrower than the first frequency band.

10. The vibration type actuator apparatus according to claim 9, wherein when said vibration element and said contact element are moved relative to each other, said control unit generates, as the driving voltage, an AC voltage for generating a driving force larger than a holding force for holding the relative positional relationship between said vibration element and said contact element, and when the relative positional relationship between said vibration element and said contact element is held, said control unit stops application of the driving voltage to said electromechanical energy conversion element, or generates an AC voltage for generating a driving force smaller than the holding force for holding the relative positional relationship between said vibration element and said contact element.

11. The vibration type actuator apparatus according to claim 9, wherein said control unit applies, as the driving voltage, a plurality of AC voltages having a phase difference from each other, to said electromechanical energy conversion element, and
wherein when an amplitude or a pulse width of at least one of the plurality of AC voltages is set to zero or a value not larger than a predetermined value, said setting unit sets the second frequency band in said filter.

12. The vibration type actuator apparatus according to claim 9, further comprising a detection unit configured to detect an amplitude of a voltage applied to said electromechanical energy conversion element or an amplitude of vibration excited in said vibration element, and
wherein when the amplitude of the voltage detected by said detection unit becomes not higher than a predetermined value, or the amplitude of the vibration detected by said detection unit becomes not higher than a predetermined value, said setting unit sets the second frequency band in said filter.

13. The vibration type actuator apparatus according to claim 9, wherein said control unit applies, as the driving voltage, a plurality of AC voltages having a phase difference from each other, to said electromechanical energy conversion element, and wherein when the phase difference between the plurality of AC voltages is set in a predetermined range having 0 degrees or ±180 degrees as a center thereof, said setting unit sets the second frequency band in said filter.

14. The vibration type actuator apparatus according to claim 9, wherein said vibration actuator includes a plurality of vibration elements as the vibration element and a single contact element as the contact element, and
wherein when said vibration element and said contact element are moved relative to each other, said control unit generates, as the driving voltage, an AC voltage for exciting vibration that causes the plurality of vibration elements to apply thrusts to said contact element in the same direction, and when the relative positional relationship between said vibration element and said contact element is held, said control unit generates, as the driving voltage, an AC voltage for exciting vibration that makes a sum of the thrusts applied to said contact element by the plurality of vibration elements equal to zero.

15. The vibration type actuator apparatus according to claim 9, wherein the first position signal is an AC signal having a frequency corresponding to a relative moving speed between said vibration element and said contact element, and the second signal is a signal indicative of an amount of relative movement between said vibration element and said contact element,
wherein said filter includes:
a changing unit configured to change the frequency band of the first position signal based on the specific frequency band set by said setting unit, and
a conversion unit configured to convert the first position signal of which the frequency band is changed by said changing unit to the second position signal.

16. The vibration type actuator apparatus according to claim 15, wherein the first position signal is a digital signal having a binary state, and
wherein said changing unit outputs the first position signal to said conversion unit in a case in which the first position signal holds the same value for a predetermined or longer time period.

17. The vibration type actuator apparatus according to claim 15, wherein the first position signal is a digital signal having a binary state, and
wherein when a time interval between two changes sequentially occurring in the first position signal is shorter than a predetermined time period, said filter ignores the two changes, and when the time interval is longer than the predetermined time period, said filter outputs the first position signal.

18. The vibration type actuator apparatus according to claim 9, wherein the first position signal is an AC signal having a frequency corresponding to a relative moving speed between said vibration element and said contact element, and the second signal is a signal indicative of an amount of relative movement between said vibration element and said contact element,
wherein said filter includes:
a first changing unit configured to change a frequency band of the first position signal,
a conversion unit configured to convert the first position signal of which the frequency band is changed by said first changing unit to the second position signal, and
a second changing unit configured to change a frequency band of the second position signal converted by said conversion unit, and wherein said setting unit sets different frequency bands in said first changing unit and said second changing unit, respectively, as the specific frequency band set in said filter.

19. The vibration type actuator apparatus according to claim 18, wherein said setting unit sets the frequency band set in said second changing unit to a band which is narrower than the frequency band set in said first changing unit, and includes 0 Hz.

20. The vibration type actuator apparatus according to claim 18, wherein the first position signal is a digital signal having a binary state, and
wherein in a case in which the first position signal holds the same value for a predetermined or longer time period, said first changing unit outputs the first position signal to said conversion unit.

21. The vibration type actuator apparatus according to claim 18, wherein the first position signal is a digital signal having a binary state, and
wherein when a time interval between two changes sequentially occurring in the first position signal is shorter than a predetermined time period, said first changing unit ignores the two changes, and when the time interval is longer than the predetermined time period, said first changing unit outputs the first position signal.

22. The vibration type actuator apparatus according to claim 9, wherein said control unit includes:
a waveform generation unit configured to generate a signal having a predetermined waveform for exciting vibration in said vibration element, and
an amplification unit configured to amplify the signal generated by said waveform generation unit to thereby generate the driving voltage.

23. The vibration type actuator apparatus according to claim 9, wherein said setting unit sets a frequency range of the first frequency band according to a relative moving speed between said vibration element and said contact element.

24. The vibration type actuator apparatus according to claim 23, wherein said setting unit sets an upper limit frequency of the first frequency band to be higher than a frequency of the first position signal corresponding to a maximum speed of the relative moving speed between said vibration element and said contact element.

25. The vibration type actuator apparatus according to claim 23, wherein said setting unit sets the upper limit frequency of the second frequency band to be higher than a frequency of the first position signal corresponding to a minimum speed of the relative moving speed between said vibration element and said contact element.

26. The vibration type actuator apparatus according to claim 9, wherein said setting unit sets an upper limit frequency of the second frequency band to be lower than a natural frequency of a lowest-order natural vibration mode of said vibration actuator.

27. The vibration type actuator apparatus according to claim 9, further comprising an analysis unit configured to analyze frequency components of the first position signal and the second position signal when stopping relative movement between said vibration element and said contact element, and
wherein said setting unit sets the second frequency band based on a result of analysis by said analysis unit.

28. The vibration type actuator apparatus according to claim 9, wherein said setting unit sets the first frequency band in said filter a predetermined time period before a time at which said control unit starts driving of said vibration element in a stopped state.

29. The vibration type actuator apparatus according to claim 9, wherein said setting unit sets the second frequency band in said filter a predetermined time period after a time at which said control unit starts an operation for stopping said vibration element in a driven state.

30. A medical system comprising:
a vibration type actuator apparatus; and
a driven mechanism for assisting predetermined medical inspection or treatment performed on a subject,
wherein said vibration type actuator apparatus comprises:
at least one vibration actuator; and
a controller configured to control driving of said at least one vibration actuator, said at least one vibration actuator comprising:
a vibration element including an electromechanical energy conversion element, and an elastic body bonded to said electromechanical energy conversion element; and
a contact element in pressure contact with said vibration element,
wherein said vibration element and said contact element are moved relative to each other by vibration excited in said elastic body by applying a driving voltage to said electromechanical energy conversion element by said controller,
said controller comprising:
a position detection unit configured to output a first position signal corresponding to an amount of relative movement between said vibration element and said contact element;
a filter configured to have the first position signal input thereto, and output a second position signal generated by attenuating signal components having frequencies except a specific frequency band;
a control unit configured to control driving and stopping of said vibration element according to the second position signal; and
a setting unit configured to set in said filter, as the specific frequency band, a first frequency band in a case in which said vibration element and said contact element are moved relative to each other, and a second frequency band in a case in which a relative positional relationship between said vibration element and said contact element is held,
wherein the first frequency band and the second frequency band both include 0 Hz, and the second frequency band is narrower than the first frequency band,
wherein said driven mechanism includes a plurality of movable portions, and
wherein said vibration actuator is integrated in each movable portion of said driven mechanism, and said vibration actuator effects motion of the movable portion.

31. The medical system according to claim 30, further comprising a magnetic field generation unit configured to generate a magnetic field, and
wherein said driven mechanism is arranged within or in the vicinity of a magnetic field generated by said magnetic field generation unit.

* * * * *